United States Patent [19]
Iliff

[11] Patent Number: 5,910,107
[45] Date of Patent: Jun. 8, 1999

[54] COMPUTERIZED MEDICAL DIAGNOSTIC AND TREATMENT ADVICE METHOD

[75] Inventor: Edwin C. Iliff, La Jolla, Calif.

[73] Assignee: First Opinion Corporation, La Jolla, Calif.

[21] Appl. No.: 08/866,881

[22] Filed: May 30, 1997

Related U.S. Application Data

[62] Division of application No. 08/176,041, Dec. 29, 1993, Pat. No. 5,660,176.

[51] Int. Cl.$^6$ .............................. G06F 15/42; A61B 5/02
[52] U.S. Cl. ........................................................ 600/300
[58] Field of Search ........................... 600/300; 128/898, 128/897, 903, 904, 920–925

[56] References Cited

U.S. PATENT DOCUMENTS

| 5,517,405 | 5/1996 | McAndrew et al. | 364/401 |
| 5,553,609 | 9/1996 | Chen et al. | 128/904 X |
| 5,572,421 | 11/1996 | Altman et al. | 395/203 |
| 5,619,991 | 4/1997 | Sloane . | |
| 5,633,910 | 5/1997 | Cohen | 379/38 |

FOREIGN PATENT DOCUMENTS 0 531 889
  A2/A3  3/1993  European Pat. Off. .
WO 93/23819  11/1993  WIPO .

Primary Examiner—John P. Lacyk
Assistant Examiner—Samuel Gilbert
Attorney, Agent, or Firm—Knobbe, Martens, Olson & Bear, LLP

[57] ABSTRACT

A system and method for providing computerized, knowledge-based medical diagnostic and treatment advice. The medical advice is provided to the general public over a telephone network. Two new authoring languages, interactive voice response and speech recognition are used to enable expert and general practitioner knowledge to be encoded for access by the public. "Meta" functions for time-density analysis of a number of factors regarding the number of medical complaints per unit of time are an integral part of the system. A semantic discrepancy evaluator routine along with a mental status examination are used to detect the consciousness level of a user of the system. A re-enter feature monitors the user's changing condition over time. A symptom severity analysis helps to respond to the changing conditions. System sensitivity factors may be changed at a global level or other levels to adjust the system advice as necessary.

25 Claims, 40 Drawing Sheets

Node Block

```
Node = 2200
Parent = 101
Type = Link
Digits = 0
Help list      → <empty list>
Play list      → 2200
Next list      → If Real = True the 2201 else 2205
Work list      → Problem = CCHP
```
218

Symbol Table

```
Age = 45
Sex = Male
Real = True
Problem = CCHP
```
220

*Fig.5d*

Node Block

```
Node = 2201
Parent = 2200
Type = Link
Digits = 0
Help list      → <empty list>
Play list      → <empty>
Next list      → 1=2205
Work list      → Write Meta
```
222

Symbol Table

```
Age = 45
Sex = Male
Real = True
Problem = CCHP
```
224

*Fig.5e*

Node Block

```
Node    = 2205
Parent  = 2200
Type    = YesNo
Digits  = 1
Help list   → <empty list>
Play list   → 2205
Next list   → 1=2206, 2=2210
Work list   → <empty list>
```
226

Symbol Table

```
Age     = 45
Sex     = Male
Real    = True
Problem = CCHP
```
228

*Fig.5f*

Node Block

```
Node    = 2210
Parent  = 2205
Type    = YesNo
Digits  = 1
Help list   → <empty list>
Play list   → 2210
Next list   → 1=2211, 2=2215
Work list   → <empty list>
```
230

Symbol Table

```
Age     = 45
Sex     = Male
Real    = True
Problem = CCHP
```
232

*Fig.5g*

COMPUTERIZED MEDICAL DIAGNOSTIC AND TREATMENT ADVICE METHOD

This application is a divisional of U.S. patent application Ser. No. 08/176,041, filed Dec. 29, 1993, U.S. Pat. No. 5,660,176.

MICROFICHE APPENDIX

A Microfiche Appendix containing computer source code is attached. The Microfiche Appendix comprises 9 sheets of microfiche having 454 frames, including one title frame.

The Microfiche Appendix contains material which is subject to copyright protection. The copyright owner has no objection to the reproduction of such material, as it appears in the files of the Patent and Trademark Office, but otherwise reserves all copyright rights whatsoever.

BACKGROUND OF THE INVENTION

1. Field of the Invention

The present invention relates to medical knowledge systems and, more particularly, to systems for giving medical advice to the general public over a telephone network.

2. Description of the Related Technology

Health care costs currently represent 14% of the United States Gross National Product and are rising faster than any other component of the Consumer Price Index. Moreover, usually because of an inability to pay for medical services, many people are deprived of access to even the most basic medical care and information.

Many people delay in obtaining, or are prevented from seeking, medical attention because of cost, time constraints, or inconvenience. If the public had universal, unrestricted and easy access to medical information, many diseases could be prevented. Likewise, the early detection and treatment of numerous diseases could keep many patients from reaching the advanced stages of illness, the treatment of which is a significant part of the financial burden attributed to our nation's health care system. It is obvious that the United States is facing health-related issues of enormous proportions and that present solutions are not robust.

One prior attempt at a solution to the health care problem is called Ask-A-Nurse, wherein a group of nurses provide health information by telephone around-the-clock. A person with a medical problem calls an 800 number and describes the problem to the nurse. The nurse uses a computer for general or diagnostic information on the ailment or complaint mentioned by the caller. The nurse may then refer the caller to a doctor from a computerized referral list for a contracting hospital or group of hospitals. Client hospitals contract with Ask-A-Nurse to provide patient referrals. A managed care option called Personal Health Advisor is similar and adds the capability for the caller to hear prerecorded messages on health topics 24 hours a day. Several problems exist with these prior medical advice systems. First, these systems have high costs associated with having a nurse answer each telephone call. Second, the caller may have to belong to a participating health plan to utilize the service. Third, if for some reason all nurses on a particular shift happen to be busy and the caller has an emergency condition (that is not known by the caller to be an emergency), precious time in getting emergency services may be lost during the delay.

Another prior health system was developed by InterPractice Systems which provides a computerized service that answers health care questions and advises people in their homes. A health maintenance organization (HMO) may provide this service to its members in a particular geographic area. To get advice at home, an HMO member connects a toaster-sized box to a telephone and calls a toll-free 800 number. Using a keyboard that is part of the box, the user answers questions displayed on a screen of the box relating to the user's symptoms. Depending on the answers, the user might be told to try a home remedy, be called by a nurse or doctor, or be given an appointment to be examined. A limitation of this system is the additional expense of the electronics box, which could either be purchased by the user for approximately $300 or purchased by the health organization with the expense to be passed on to the users. Another limitation is that this service is directed to members of a particular contracting health organization, such as an HMO. What is desired is a system that does not require additional hardware for the basic service, but that utilizes the existing communication network. The desired system should be available for use by any person, not just members of a certain organization.

A prior attempt at a health care solution for a limited set of conditions is described in U.S. Pat. No. 4,712,562. A patient's blood pressure and heart rate are measured and the measurements are sent via telephone to a remote central computer for storage and analysis. Reports are generated for submission to a physician or the patient. U.S. Pat. No. 4,531,527 describes a similar system, wherein the receiving office unit automatically communicates with the physician under predetermined emergency circumstances.

U.S. Pat. No. 4,838,275 discloses a device for a patient to lay on or sit in having electronics to measure multiple parameters related to a patient's health. These parameters are electronically transmitted to a central surveillance and control office where a highly trained observer interacts with the patient. The observer conducts routine diagnostic sessions except when an emergency is noted or from a patient-initiated communication. The observer determines if a nonroutine therapeutic response is required, and if so facilitates such a response. As previously mentioned, highly trained people are needed by this system along with the special measurement apparatus (embedded in a bed or chair).

Other prior attempts at a health care solution are typified by U.S. Pat. No. 5,012,411 which describes a portable self-contained apparatus for measuring, storing and transmitting detected physiological information to a remote location over a communication system. The information is evaluated by a physician or other health professional. As before, highly trained people are necessary to utilize such an apparatus.

Several services to provide medical or pharmaceutical advice are now available via "1-900" telephone numbers, e.g., "Doctors by Phone." These services are available 24 hours a day and 7 days a week. A group of doctors, including some specialties, is available to answer questions about health care or medical conditions for people anywhere in the United States who call the "1-900" telephone of one of the services. A group of registered pharmacists answers questions about medications for the "1-900" pharmaceutical service.

SUMMARY OF THE INVENTION

The present solution to the health care problem is a computerized medical diagnostic and treatment advice (MDATA) system that is a medical knowledge-based system designed to give medical advice to the general public over the telephone network. The goal of the MDATA system is to provide everyone with equal access to high quality, 100%-consistent medical advice at a reasonable cost. The MDATA system provides callers with extremely fast and virtually unlimited access to health care information, twenty-four hours a day, from any location around the world. Health care advice is made available to an entire spectrum of users, from elderly patients confined to their homes to travelers in a foreign country with telephones in their cars.

The central ideas leading to the development of the MDATA system are based on the following assumptions:

Nearly 90% of all patient complaints are confined to approximately 100 medical problems.

Almost all primary care decisions involved in these 100 problems can be made based upon information learned solely by obtaining a detailed medical history. The results of the physical examination, laboratory, and imaging studies only tend to confirm a diagnosis.

The minimal amount of information that many doctors believe can only be obtained from the physical examination can actually be directly acquired from the patient when given appropriate instructions.

In most cases, a face-to-face interaction between the doctor and patient is not necessary. A detailed and well-constructed history, along with physical findings elicited from the patient, can be obtained over the telephone.

Medicine is basically diagnosis and treatment. Although treatment recommendations change frequently, the fundamental principles of making the diagnosis do not.

There is a significant delay between the time a new therapy is recognized as safe and effective and the time physicians are able to provide it to their patients.

These central ideas are utilized in the implementation of the MDATA system.

A goal of the MDATA system is to give better medical advice than a family practitioner who is unfamiliar with a patient, e.g., an on-call physician. A person seeking medical advice frequently will not be able to see or speak with his or her personal physician in a timely manner. The MDATA system provides medical advice whenever desired by the caller—seven days a week/24 hours a day.

All previous medical algorithms, including those used in the military, are designed for face-to-face interactions. Self-help books generally do not consider age and sex in their algorithms. Furthermore, a book cannot take into account how many times a person has consulted the same algorithm within a short period of time for the same problem. The medical algorithms used by the MDATA system are designed for use in a telecommunications setting and overcome the deficiencies of self-help books.

Previous medical advice systems do not do a time-density analysis for a number of factors with regard to the number of complaints per unit of time. The MDATA system uses "meta" functions to perform these analyses.

Previous medical advice algorithms do not have a way of detecting the consciousness level of the person seeking consultation. The MDATA system invokes a "mental status examination" whenever a complaint or problem has the possibility of an altered level of consciousness. In addition, the MDATA system uses "semantic discrepancy evaluator loops" which allow the system to invoke the mental status exam if there are differences in answers to the parallel threads of thought that are woven or embedded into the system.

Other medical advice systems do not have a "re-enter" feature to monitor a patient's progress or worsening over time. The MDATA system checks for and responds to changing conditions over time.

Prior medical advice systems suffer from the inability to be nearly instantly up-dated as new medical information is made available. The MDATA system regularly and frequently updates the treatment aspect of the system.

The computerized medical diagnostic and treatment advice (MDATA) system is a medical knowledge-based system designed to give medical advice to the general public over the telephone network. Using a new authoring language, interactive voice response and speech recognition technology, the MDATA system encodes a highly useful core of expert and general practitioner diagnostic and treatment knowledge into a computerized system for access by non-medically trained personnel.

The MDATA system does not provide advice for every medical problem, nor does it make an exhaustive study of one vertical cross-section of medicine. Instead, the MDATA system provides up-to-date medical advice for approximately one hundred of the most commonly encountered problems in general practice and emergency medicine. It also provides valuable information to the public on any number of other medical topics.

As another embodiment of the MDATA system, a person desiring medical advice and having access to a personal computer (PC) loads a program into the PC to produce a stand-alone medical diagnostic and treatment advice (SA-MDATA) system. Rather than listening to questions and responding via touch tone keypresses or via voice, the user responds to questions and directions displayed on the computer screen via a computer input device, such as a keyboard or mouse. The diagnosis and/or treatment recommendations provided by the MDATA system are the same as that provided by the SA-MDATA system. The user of the SA-MDATA system can procure updates by contacting the MDATA system sponsor/administrator to obtain the most current treatment table information for a particular diagnosis.

One aspect of the present invention includes, in a computer system, a method of automating medical diagnosis and treatment advice, comprising the steps of providing a representation of connected nodes corresponding to a set of diagnostic steps for a selected medical problem, providing a set of action lists associated with each node, providing a script for each one of selected nodes, each script requesting information or providing medical advice, translating the node representation into a node table and a plurality of list files, processing the list files and a plurality of records in the node table to generate patient questions, and generating medical advice based on answers to the patient questions and the diagnostic steps for a selected medical problem.

Another aspect of the present invention includes, in a medical diagnostic and treatment advice system, comprising an algorithm processor executing in a computer, a method of providing medical information to any one of a plurality of patients, comprising the steps of providing a representation corresponding to a set of steps directed to diagnosing a selected medical problem, translating the representation into a medical complaint algorithm, selectively executing one of a plurality of medical complaint algorithms, determining medical advice particular to a medical condition through communication with the computer, and providing the medical advice particular to the medical condition to an output of the computer.

Yet another aspect of the present invention includes, in a medical diagnostic and treatment advice system, comprising an algorithm processor executing in a computer, wherein an input and an output device connect to the computer, a method of providing medical information to a patient, comprising the steps of providing a representation of connected nodes corresponding to a set of diagnostic steps for a selected medical problem, translating the node representation into a node table and a plurality of list files thereby generating a medical complaint algorithm, processing the list files and a plurality of records in the node table on the algorithm processor to generate patient questions, transmitting medical information via the output device, receiving medical information via the input device, scoring at least a portion of the received medical information, repeating the transmitting, receiving and scoring steps a plurality of times, combining each of the scores obtained from the scoring steps to create a combined score, comparing the combined score with a threshold, and diagnosing the medical condition associated with the executed medical complaint algorithm if the combined score exceeds the threshold.

BRIEF DESCRIPTION OF THE DRAWINGS

FIGS. 5b–5g are an exemplary sequence of data structures of the system shown in FIG. 1 at run time;

FIGS. 8a and 8b are a flow diagram of the patient login process 250 defined in FIG. 7a;

FIGS. 9a and 9b are a flow diagram of the patient registration process 252 defined in FIG. 7a;

DETAILED DESCRIPTION OF THE PREFERRED EMBODIMENT

The following detailed description of the preferred embodiments presents a description of certain specific embodiments to assist in understanding the claims. However, the present invention can be embodied in a multitude of different ways as defined and covered by the claims.

For convenience, the following description will be outlined into the following 22 principal sections: Introduction, System Overview, Operating Features of the MDATA System, Authoring Language, Run-Time Operation, Software Structure, Top-Level Flow, Login Process, Registration Process, Evaluation Process, The Meta Function, Mental Status Examination, Semantic Discrepancy Evaluator Routine, Past Medical History Routine, Physical Self Examination, Symptom Severity Analysis, Treatment Table, The MDATA System Paradigm, Video Imaging, Benefits of the MDATA System, Optional System Configuration, and Summary of Advantages of the Present Invention.

I. Introduction

A consultation for a person seeking medical advice begins with a telephone call to the medical diagnostic and treatment advice (MDATA) system of the present invention. The MDATA system asks the caller specific questions and then analyzes each response.

Voice recognition and interactive voice response technology allow callers to respond to yes/no and multiple choice questions either by speaking directly into the telephone or by using the touch tone pad of their telephone.

Easy access to the information in the MDATA system is made possible by a natural user interface. The computer-driven dialogue consists of simple yes/no and multiple choice questions. The questions and treatment recommendations are very simply worded yet skillfully designed to reflect the accumulated experience of many physicians in conducting patient interviews.

Although all the MDATA system's questions are designed to be easily understood, unforeseen situations will inevitably arise. For this reason, hierarchical staffing is implemented. As an example, for every 10 telephone lines, one operator fully trained in triage and the MDATA system will be available. For every 10 operators there will be one registered nurse in attendance; and for every 10 registered nurses, there will be one physician in attendance. Staffing requirements are adjusted as the system is refined toward optimal efficiency. The MDATA system does not require the operator or the registered nurse to make any medical decisions.

II. System Overview

Figure 1:
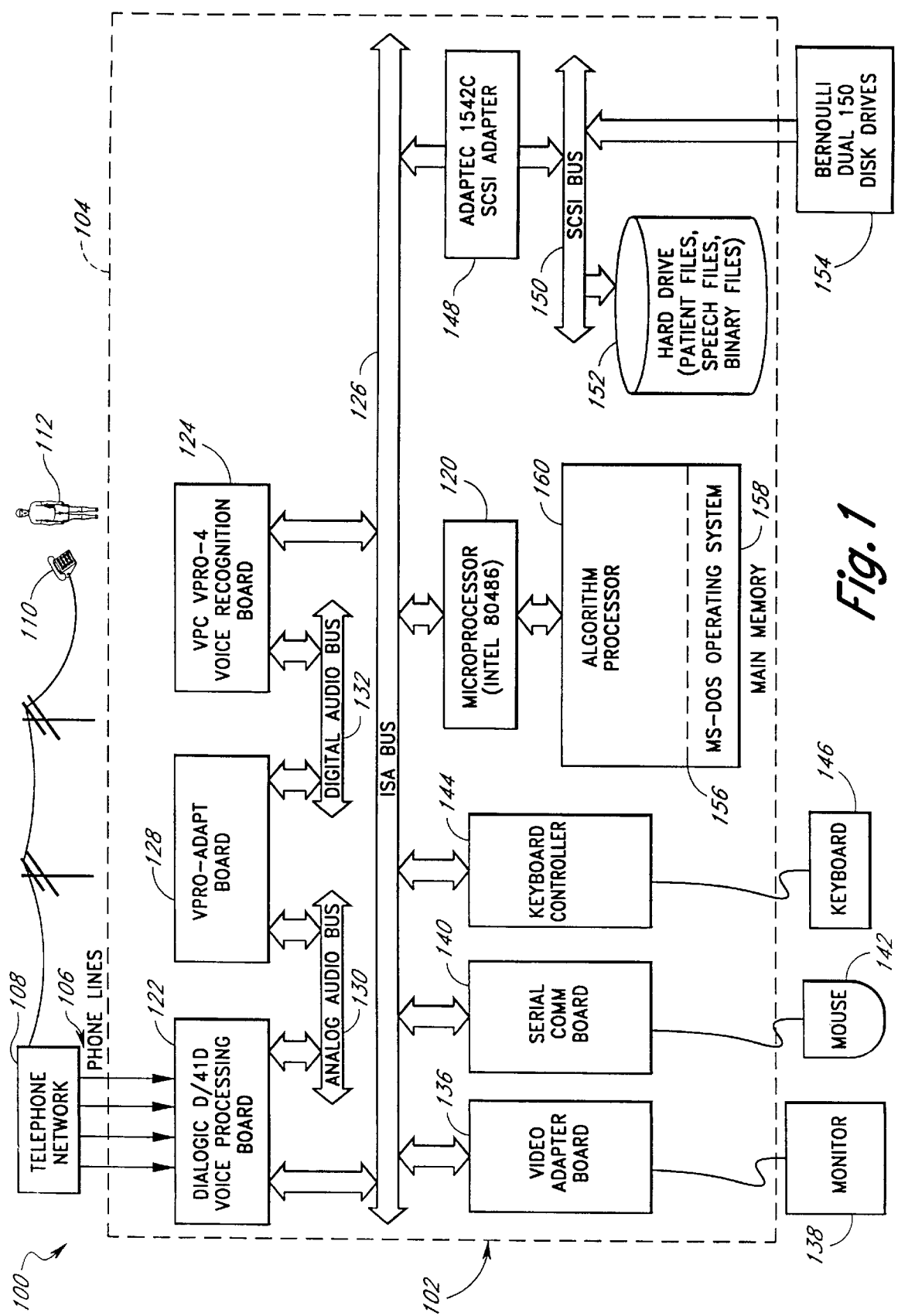
FIG. 1 is a block diagram illustrating the components of a presently preferred embodiment of the computerized medical diagnostic and treatment advice (MDATA) system of the present invention.

Referring to FIG. 1, the components of a presently preferred embodiment of the computerized medical diagnostic and treatment advice (MDATA) system 100 of the present invention are shown. A personal computer (PC) 102 includes a plurality of components within an enclosure 104. A plurality of telephone lines 106 interface the public telephone network 108 to the computer 102. As an example, one of telephone lines 106 is shown to be switched via network 108 to connect with a telephone 110 that is used by a person desiring medical advice (user) 112. Throughout this document, the words user, caller and patient are used interchangeably. However, it will be understood that the caller may be acting as a proxy for the patient. If this is the case, the caller will be registered as an assistant for the patient.

The hardware and system software were assembled with two basic concepts in mind: portability to other operating systems and the use of industry standard components. In this way, the system can be more flexible and will allow free market competition to continuously improve the product, while, at the same time, decrease costs. While specific hardware and software will be referenced, it will be understood that a panoply of different components could be used in the present system.

The system currently runs on the PC 102 with an Intel 80486 microprocessor. "Telephony" functions use Dialogic Corporation's D/41D voice processing board 122 based on a digital signal processor (DSP). The voice processing (VP) board 122 performs several functions including interfacing the telephone lines, decoding touch tone signals, speech recording and speech playback. Touch tone signals are also known as "dual tone multiple frequency" (DTMF) signals. A group of one to four telephone lines 106 connect to the VP board 122. The computer 102 may include a plurality of VP boards 122 based on how many phone line connections are desired for the system 100. Speech recognition is achieved using Voice Processing Corporation's speech recognition VPRO-4 board 124 (also DSP based). The voice recognition (VR) board 124 performs several functions including recognizing utterances and returning an index number of a recognition confidence level. The VR board 124 and the VP board 122 both connect to an industry standard architecture (ISA) bus 126. The ISA bus 126 interconnects the microprocessor 120 with a plurality of peripherals through controller circuits (chips or boards).

The VP board 122 also connects to a VPRO-Adapt board 128 via an analog audio bus 130 that is called Analog Extension Bus. Four simultaneous channels provide a 96 kbit/second data transfer rate. Each channel corresponds to a telephone line connected to the VP board 122 and is associated with a current patient consultation. The Adapt board 128 further connects to a digital audio bus 132. The VR board 124 also connects to the digital audio bus 132. The Adapt board 128 performs analog to digital signal conversion to a VPC-proprietary digital pulse code modulation (PCM) format. The digital bus 132 can accommodate 32 channels and has a data transfer rate of 2.048 Mbits/second.

The computer ISA bus 126 has a plurality of peripherals connected to it through adapters or controllers. A video adapter board 136, preferably at VGA or better resolution, interconnects to a video monitor 138. A serial communication circuit 140 interfaces a pointing device, such as a mouse 142. A parallel communication circuit may be used in place of circuit 140 in another embodiment. A keyboard controller circuit 144 interfaces a keyboard 146. A small computer systems interface (SCSI) adapter, such as model 1542C made by Adaptec, provides a SCSI bus 150 to which a 500 Mb or greater hard disk drive 152 and dual Bernoulli 150 Mb disk drives are preferably attached. The hard drive 152 stores database files such as the patient files, speech files, and binary support files.

A main memory 156 connects to the microprocessor 120. In the presently preferred embodiment, the MDATA system 100 operates under DOS version 5.0 operating system 158. The system software is written in Microsoft C\C++ version 7.0 using structured programming techniques. An algorithm processor 160 includes a parser and supporting functions that manipulate a memory variable symbol table and a run time stack, which will be described hereinbelow. Sequiter Software Inc. Codebase 5.0 allows access to X-base compatible database records stored on the hard drive 152. The MDATA system 100 also includes two new authoring languages (one each is used in two embodiments of the system), which will be discussed hereinbelow.

The system software includes the following code modules for which source code is included in the attached Microfiche Appendix:

A. main.c—a collection of functions that mostly deal with telephony functions, such as answering the phone line, speech file playback, and DTMF tone collection. Global data structures are defined here.

B. base.c—functions that invoke the CodeBase revision 5.0 library to perform xbase file manipulation.

C. pars.c—the parse function, and supporting functions that manipulate the memory variable symbol table and run time stack.

D. regi.c—an on-line patient registration module.

E. resp.c—gets the caller's responses, either DTMF or voice, and figures out what to do next by obeying a command (e.g., "repeat" or "backup"), or traversing through the algorithm node map.

F. term.c—a useful collection of text phrases for Dialogic and VPC board termination events and error codes.

G. user.c—"non-diagnostic" portions of the caller session: initial screening questions, caller login, and the next node playback initiator.

H. util.c—a collection of general purpose functions shared by a run time executable, a node editor and ASCII translator tools.

I. view.c—a module that controls the graphics system display.

J. x10.c—an X-10 computer interface routine for fault recovery.

K. xlat.c—a module linked with pars.c and util.c object modules to build xlat.exe, a stand-alone translation executable for offline ASCII text file translation.

The application is compiled with the Microsoft graphics, Dialogic board, VPC board and CodeBase database libraries.

The Voice Processing Corporation (VPC) VPro-4 VR board has eight voice recognition channels, which by default are associated one-to-one with the Dialogic D/41D channels. VPC's pioneering work in the voice processing field is in the area of continuous speech. This allows a person to speak a multiple digit number in a natural manner, without pausing after each digit. VPC supplies two continuous speech vocabularies: one vocabulary contains the digits 1 through 9, plus "zero" and "oh", and the other contains just the two words "yes" and "no". The vendor-supplied digits continuous speech vocabulary is used by the system 100. In the presently preferred embodiment, if the score is 75% or better, the response is unconditionally accepted. If the score is between 20% and 74%, the digits recognized are read back, and the caller is asked to accept or reject the digits. In another embodiment of the system 100, the above score thresholds are implemented as tunable parameters. The scoring parameters are stored in a configuration file that is manipulated off-line by a utility program and is read by the run-time system at initialization.

VPC also provides a few discrete vocabularies. Discrete vocabularies contain one or two word utterances. The vendorsupplied discrete speech vocabulary of the months of the year is used in the on-line patient registration process. A speaker-independent discrete speech vocabulary consisting of the words "yes", "no", "backup", "continue", "help", "operator", "pause", "quit" and "repeat" has been developed using a very powerful set of utilities supplied by VPC, Scripter and Trainer. These utilities are for collecting samples and training the vocabulary.

The VR board 124 has the minimum of two MB memory installed. The default memory configuration has a partition for both continuous vocabularies and a partition for one discrete vocabulary. Additional discrete vocabularies may be is downloaded if the on-board memory is reconfigured.

The VR board 124 has four digital signal processors (DSP's) from which VPC derived eight voice recognition channels. Each of these eight recognition resources is referred to as a VPro Speech Processor (VSP). Discrete vocabulary recognition requires one VSP; continuous vocabulary recognition requires two adjacent VSP's. The MDATA system 100 has a VSP resource manager in the resp.c software module. This resource manager allocates VSP's in a dynamic manner to VP board 122 channels on a demand basis. As soon as the system receives a response, voice or DTMF, it releases the VSP's associated with the caller's VP board 122 channel.

The MDATA system 100 uses VPC's application programming interface (API) for the C programming language. This makes the application vendor specific to VPC, but also allows the system 100 to utilize all the powerful API features, e.g., on-line creation of discrete speaker dependent vocabularies used for voice pattern matching or voice printing.

The VPC API supports both continuous speech vocabulary (CSV) and discrete speech vocabulary (DSV) recognition.

The voice processing (VP) board 122 supports speech recording and playback, as well as touch tone (DTMF) signal detection and decoding. A device driver, associated with the VP board 122, is loaded into system memory during load operations. The device driver supports communications between the VP board 122 and the application code at run time (e.g., when a person is seeking medical advice). Through a shared memory segment, the device driver sends event and status data to the application code in real-time as events occur on the associated telephone line. These events include the ring of an incoming call, touch tone key pressed by the caller, and the hang-up signal. The VP board 122 plays back speech messages that are stored on the hard drive 152. The algorithm processor 160 sends a selected speech file having an encoded speech message that is retrieved from the hard drive 152 to the VP board 122 at the appropriate time for speech message playback. A speech message can be of variable length with a typical message about one to two minutes in length. Several speech messages may be chained together to produce an extended spoken message, e.g., giving instructions to the patient. During speech file playback, the VP board 122 is monitoring touch tone response from the caller. The VP board 122 may be configured to interrupt speech file playback when a touch tone signal is detected.

System Operating Contexts The system has an activity flag in the port status block for each patient currently using the system to keep track of which state the associated VP board channel is in:

a. Idle Mode—an idle channel waiting for a telephone call;

b. Login Mode—a condition where a patient is in the login process;

c. Registration Mode—a condition where a patient is in the registration process;

d. Real Mode—a condition where a patient is consulting for an actual medical problem;

e. Info (Information) Mode—a condition where a patient is consulting for information or a hypothetical situation;

f. Pause Mode—a patient-initiated pause condition;

g. Pending Mode—similar to Real mode except that new medical information gathered for a patient is not automatically added to the patient's medical record, but rather written to a "Pending" file where it will be verified off-line by a staff person.

Voice Keywords and DTMF Command Keys The system is responsive to the following voice keywords and DTMF keys when it is in a prompting state, i.e., not in response to a menu message:

| Voice | DTMF | |
|---|---|---|
| yes | 1 | Useful for answering yes/no questions. |
| no | 2 | |
| backup | # | Causes the system to back up to the "predecessor" message (see below), then resume playback. |
| help | * | Plays helpful information: either the node's help message list, or the DTMF command explanation message. |
| operator | 0 | Causes the system to transfer the caller to a live person. |
| pause | 7 | Transitions to pause mode. The system default pause period is 30 seconds. |
| quit | 9 | Quits the current algorithm, and takes the caller to node 110, which asks the caller if (s)he wishes to select another algorithm. |
| repeat | 3 | Repeats the current node's play message list. If this command is given in the middle of a long play list, then playback restarts with the first message in the list. |
| Pause Mode Commands | | |
| yes | 1 | Extends the pause period by one default pause interval (30 seconds). |
| continue | 2 | Ends pause mode. If this occurs at a Yes/No node, the system will repeat the question. If this occurs at a Link node, the system will resume playback with the "current" message. The system resolves the DTMF digit "2" ambiguity, "no" versus "continue", by examining the pause mode flag. |

Figure 2:
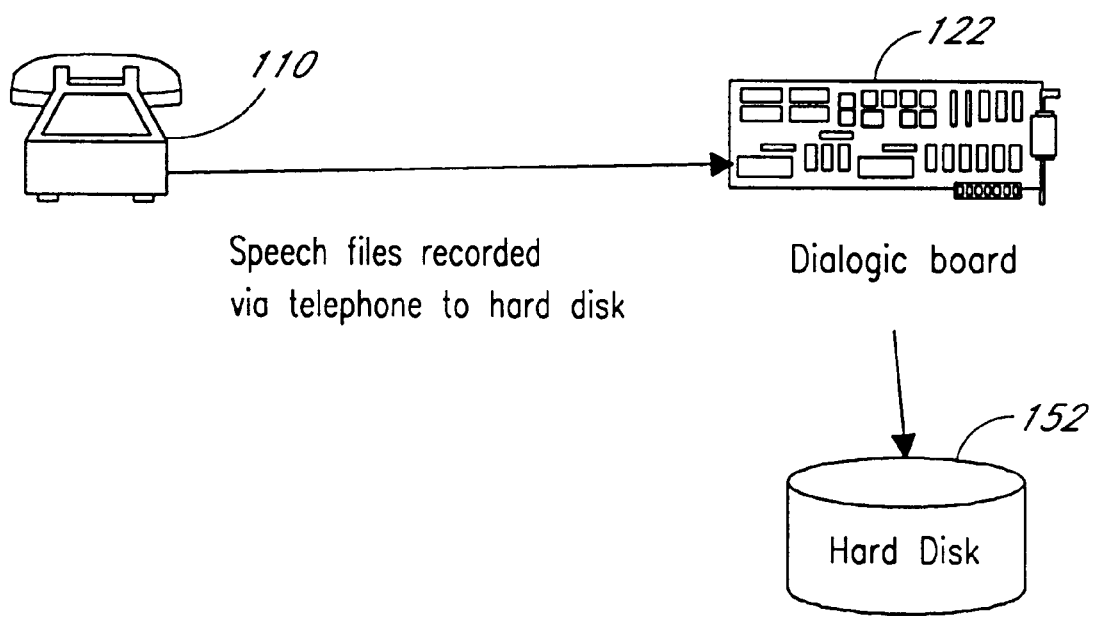
FIG. 2 is a diagram of the off-line process used in producing the speech files shown in FIG. 1.

FIG. 2 illustrates how speech files are created. A person programming medical algorithms uses speech messages to communicate with the person seeking medical advice. As previously mentioned, these speech messages are of variable length. The programmer typically writes a script for the speech message. Then using the handset of the telephone 110, a speakerphone feature, or other voice-input device, e.g., a microphone, the programmer reads the script into the voice-input device which is connected to the VP board 122. The VP board converts the speech into a digital format and records the digitized speech to a file that is stored on the hard drive 152. In the presently preferred embodiment, a subdirectory named vox contains the system speech files, and subdirectories for each medical algorithm. System speech files are of the form sysxxx, where xxx is some arbitrarily assigned number. The system messages are used by the "fixed" parts of the system, e.g., greeting, login process, registration process. There are a few speech files of the form msgxxx. These are the past medical history questionnaire messages, and response acknowledgements. There are additional speech files of the form msgxxxx in each of algorithm subdirectories, where xxxx generally matches the node number, which will be explained hereinbelow. Node messages include information, question, menu and help messages.

III. Operating Features of the MDATA System

One of the MDATA system's main objectives is to bring together highly-qualified medical experts, encode their knowledge in a central location, and make it available to everyone. A new and unique authoring language is used by the MDATA system to help accomplish this objective.

Each day, specialists perform the same tasks over and over. They enact the same diagnostic ritual of solving a familiar problem. At the same time, however, primary care physicians attempt to find the best path through the diagnostic maze of an unfamiliar problem. This process is inefficient and fraught with error.

In medicine, there is generally one best way to do things. Instead of physicians spending valuable time duplicating tasks, the MDATA system utilizes medical experts from each medical specialty who write detailed algorithms for the treatment of the 100 or so most commonly encountered complaints in family practice and emergency medicine. These algorithms are carefully and specifically designed to elicit historical data and physical findings over the telephone, rather than in face-to-face interactions.

Several experts could work together to thoroughly research one particular complaint as well as to anticipate the full spectrum of possible problems and patient responses. These experts could also provide and maintain the MDATA system treatment table as well as the imaging modality of choice and laboratory test of choice tables. These concepts will be described hereinbelow.

Carefully crafted questions, used in the taking of a medical history, are the main tools that the MDATA system uses to assess the problems of patients. The key to getting a good history is to ask the right questions. In a sense, in the diagnostic process questions are like tests. It is important to note that the right questions are basically always right; they don't change. Although they may be refined over time, in general, once excellent and well-crafted questions are developed they are good for a very long time. Of course, as new diseases are discovered, e.g., toxic shock syndrome and AIDS, new sets of diagnostic questions are developed that are disease specific.

The questions used by an earlier generation of physicians, who did not have any of the latest imaging modalities (types or methods), are far more sensitive and precise in diagnosing a patient's problem than the questions used by doctors today. The MDATA system makes use of fine nuances of language to diagnose patients as well as to determine when certain tests or imaging studies are necessary.

The MDATA system's statistic generating capabilities enable the system to analyze the effectiveness of the questions used in the diagnostic process. As a result, physicians benefit from the immense amount of statistical information that is gathered regarding the wording of questions asked in taking medical histories. For example, exactly what percentage of patients who answer "yes" to the question, "Is this the worst headache of your life?" actually have a subarachnoid hemorrhage? Although this is a classic description of this problem, the exact probability of having this kind of brain hemorrhage after answering "yes" to this question is not presently known.

Currently, doctors can only estimate the probability of certain conditions based on history. By applying the statistical information that is generated, the MDATA system not only provides the patient with advice that is continually improving, but it will also be able to pass along these probabilities to the entire medical community.

To function optimally, the MDATA system tries to gain as much medical information about its patients as possible. Although a first-time caller is given excellent advice, more specific advice can be given if the system has more information. Therefore, the MDATA system asks patients for their complete medical history. The MDATA system can either obtain the patient's medical record over the telephone or it can mail or fax a detailed questionnaire to each patient. The patient can then gather the necessary information at their convenience. The MDATA system will always be available by telephone to clarify any questions the patient may have.

The MDATA system uses the "International Classification of Diseases" (ICD■9■CM) codes to help summarize the information it has about a patient. This world standard is a comprehensive numerical system used to classify the entire spectrum of medical diseases. ICD■9■CM codes are also used to classify specific procedures performed (e.g., appendectomy) as well as the morphology of neoplasm (i.e., tissue diagnosis of a cancer).

In addition, the MDATA system 100 uses ICD■9■CM "E-Codes" to classify environmental events, circumstances, and conditions as the cause of injury, poisoning, and other adverse effects. These codes are particularly helpful for storing information about what drugs the patient has taken or is currently taking, as well as the context (e.g., therapeutic use, accident, poisoning, suicide attempt) in which they were or are being taken. For example, E942.1 is the code for the therapeutic use of digoxin. Medications are also cross-categorized according to the classification done by the American Hospital Formulary Service List (AHFS) Numbers. The MDATA system 100 also uses "V-Codes" to classify other types of circumstances or events such as vaccinations, potential health hazards related to personal and family history, and exposure to toxic chemicals.

It is estimated that the alphanumeric component of a patient's medical history will not exceed 1,000 atoms or pieces of information. An atom is considered herein to be a separate identifiable data item or point. With this assumption, the medical records of every person on the planet could currently be stored on approximately 1,000 optical disks.

While a patient interacts with the MDATA system, the system is constantly determining what questions to ask, based upon the information it has about the patient. Just as a physician gathers relevant pieces of information from his or her dialogue with a patient, the MDATA system flags and later stores all pertinent pieces of information that it learns from each interaction with its patient. Therefore, certain questions, because their answers remain the same, need not be repeated. For example, if the MDATA system learns that a patient's mother has suffered from migraine headaches, it will never have to ask for this information again.

Again, the more information the MDATA system has about a patient, the more specific is its advice. It is not uncommon for the MDATA system to give different advice to different patients calling for the same complaint. In other words, the advice given is patient-specific. Not only can the MDATA system's advice be different for different patients, but there are times when the advice given to the same patient (calling for the same complaint but at different times) is different. For example, one of a group of functions called "meta" keeps track of the number of times the MDATA system has been consulted for the same problem. Once a threshold is reached, the MDATA system advises the patient that the number of consultations alone, for the same complaint, may signify a problem. The system then makes an appropriate recommendation.

Before the MDATA system stores any information, the system verifies its accuracy. To accomplish this task, "confirmation loops" are used. Any piece of information that will become a part of the patient's medical record is sent through a confirmation loop where the system asks the patient to verify the accuracy of the information that the system has collected. The confirmation loop enables the system to verify new patient information and make corrections before it enters this information into the patient's medical record.

IV. Authoring Language

The MDATA system uses a new authoring language that is specifically designed to allow medical knowledge to be encoded into a usable computer program. The presently preferred voice response or telephony version of the MDATA system is written in object-oriented Microsoft C\C++ version 7.0. This allows the MDATA system to easily interface with industry-standard database programs, including those that are SQL-based, as well as to be portable to other operating systems. The operating system is transparent to the user.

Before the development of the MDATA system's authoring language, there was no practical way for medical experts to encode their knowledge into a meaningful, useful, and accessible structure. Although other computer languages have been used to build medical expert systems, they have almost always required a knowledge engineer and a programmer to be involved. Quite often, the knowledge encoded in these systems could only be accessed and fully understood by physicians. Typically, the programmer would try to translate the doctor's diagnostic skills and treatment rules into computer code. This separation of the physician's knowledge from the encoded treatment recommendations often engendered anxiety in the physician and has, at times, led to inaccurate treatment recommendations.

The MDATA system's authoring language, however, is designed to allow physicians to transfer their knowledge into a computer program that can be directly accessed by non-medically trained personnel. Recursive and iterative techniques are used to acquire the knowledge from the expert and assemble it in a way that allows it to be immediately transposed into the MDATA system's algorithms. Because of the simple interface of the language, and because a formula for writing the algorithms has already been developed, physicians who are not computer literate can encode their knowledge as well as understand exactly how that process takes place.

The MDATA system's authoring language allows flat information to be restructured into a hierarchical or layered format in which the arrangement of the knowledge conveys meaning. Thus, a textbook description of a disease can be transposed into a form that allows useful treatment recommendations to be made.

The new language also allows the formation of a structure in which multiple overlays of screening questions, combined with the application of recursive techniques, sequentially exclude some diagnoses while at the same time reaching treatment recommendations. The MDATA system's simplicity and elegance would not be possible without the new language.

The MDATA system's authoring language allows an algorithm programmer to retrieve information from a patient's medical record, request additional information from the patient, and guide the flow of algorithm execution based on medical history and the patient's responses. The language allows the programmer to implement an algorithm in a natural scripted style.

The course of an algorithm is determined by caller responses to questions that the MDATA system asks. For simple "yes/no" questions, the flow of interaction can be described by a binary tree. Multiple-choice questions (e.g., menus) provide multiple branches in the tree. Each question can be considered a node, and the acceptable responses to this question are branches leading to the next question (node). Using this abstraction of an algorithm, one can draw a directed graph (also known as a node map) of the nodes and branches of an algorithm, beginning with the initial question, and ending with all possible terminal points.

The node table is built in this manner:
1. An author develops an algorithm.
2. The algorithm is broken up into separate nodes.
3. A directed graph is drawn up, which is a flow chart of the algorithm's operation.
4. Each node's definition is entered into the MDATA system, either by:
   a. using an ednode utility to write each node's definition into the system's machine readable node table, or
   b. using an xlat utility to translate an ASCII file of human-readable node definitions into the system's machine readable node table.

Several example node maps are included in the attached Microfiche Appendix.

Figure 3:
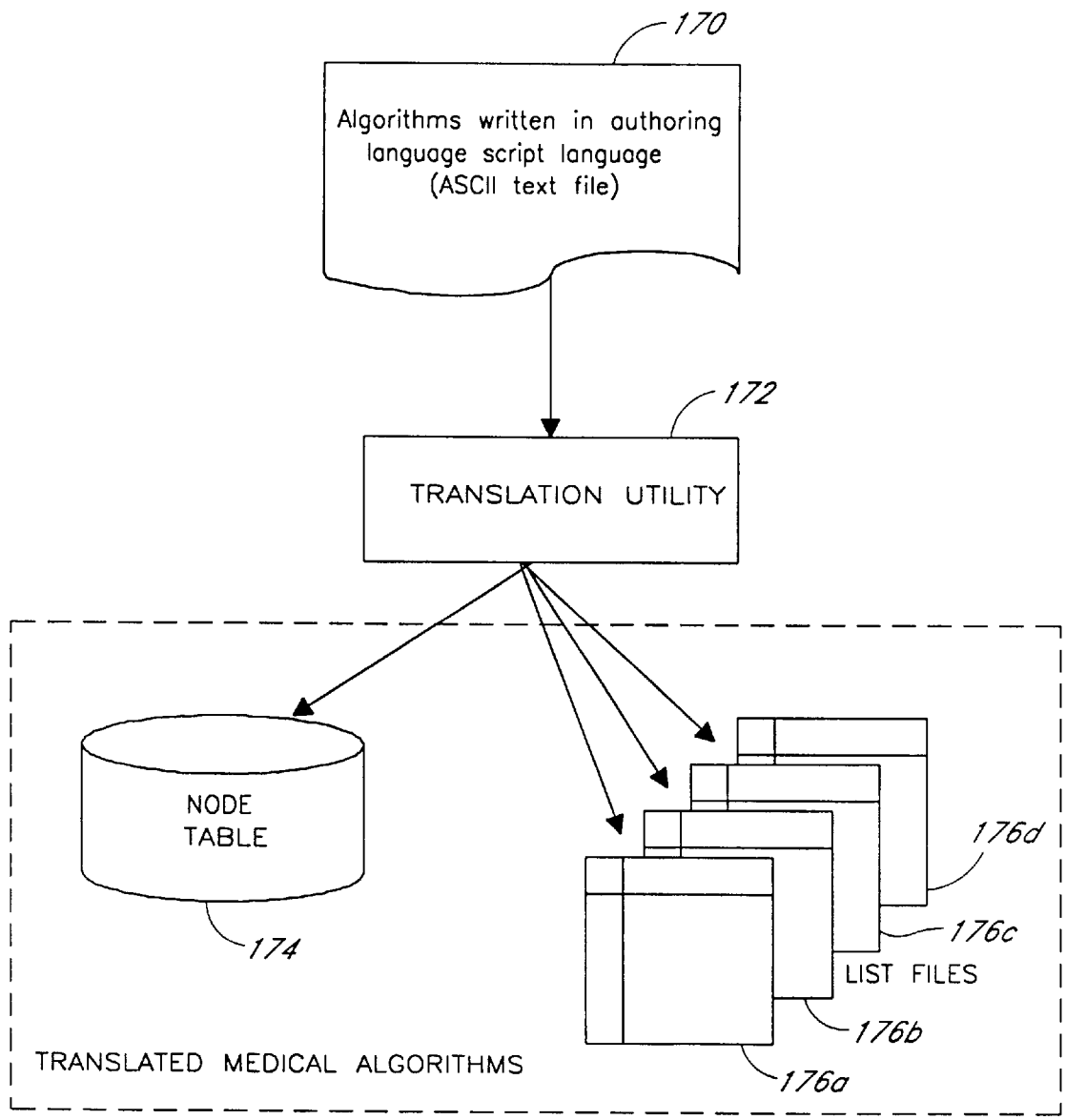
FIG. 3 is a diagram of the Node Translation process used in creating files for use by the system of FIG. 1.

Referring to FIG. 3, a process for translating a medical algorithm written in the authoring language will be described. FIG. 3 illustrates an ASCII (American Standard Code for Information Interchange) format text file 170 as an input to a translation utility 172. An ASCII file can be created by use of a text editor or a word processing program (may need to export to the ASCII format). The ASCII file 170 contains node definitions conforming to the syntax briefly described hereinbelow and more thoroughly described in the attached Microfiche Appendix. An example node definition text file 170 for Headache is included in the Microfiche Appendix.

The purpose of the ASCII node definition translator utility 172 (xlat.exe, along with functions in pars.c and util.c) is to convert a human-readable document into a machine readable format that the MDATA system reads at run time to process an algorithm. This utility 172 may be considered to be a preprocessor; the translation must be accomplished prior to run time. The translation utility 172 is listed in the Microfiche Appendix.

The output of the utility 172 is a set of binary (NOD_BLK) records written to a node table 174 (filename of node.fos), and a set of binary list files 176 (in a subdirectory \list\listxx\xxyy, where xx is the first two digits of the node number, and yy are the last two digits). Four list files 176a–176d are shown as an example. Each "list" file, e.g., 176a, contains a "next" table (i.e., the 'next node after this one'), a message play list for this node, and a "work" list (i.e., one or more "things to do" at this node before beginning speech playback). The binary record written to the node table 174 (node.fos) has fields containing the node number (which is redundant; the record's position in this file also indicates the node number), the node's "type" attribute (Menu, Link, Prompt, Yes/No, Return, Hangup) and a parent node number.

The node table 174 is a table of 10,000 NOD_BLK records. This table 174 is indexed by a node number, e.g., the fiftieth record corresponds to node 50. The contents of the individual node records may be viewed by selecting "Display Node" while running the ednode utility. The node records are modified by either using the ednode utility, or when translating node definitions from ASCII to the node file with the xlat utility.

One of the following keywords is necessary as the first item on each line, but only one keyword is accepted per line; any excess information will be discarded.

Node The Node keyword denotes the beginning of a new node and defines the node number.

Parent The Parent keyword defines the parent of the node being defined.

Type The Type keyword defines the class of the node being defined. Acceptable type names are:

Menu This node presents a multiple choice question.

YesNo This node presents a simple Yes/No type question.

Link No caller response is required at this node, algorithm processing will continue at a predetermined node.

Prompt This node requests some numeric information from the caller. The information is placed in a DTMF buffer which is then stored in the next node.

Return Returns from a subroutine call (e.g., after configuring a past medical history object).

Hangup The system will release this caller after it finishes speech file playback, or if the caller interrupts playback with a DTMF key press.

Wait nn This node will play the message list, then pause for the specified nonzero number of seconds before continuing.

@ The @ keyword defines the action to be taken for a response to either a Menu or YesNo type node.

Digits The Digits keyword is used in conjunction with Type Prompt to indicate the maximum number of DTMF digits to collect from the caller.

Play The Play keyword defines a play list of one or more messages to be played at this node.

Help The Help keyword defines a play list of one or more messages containing useful hints for interacting with the system. These messages provide helpful instructions for a new or confused caller.

Next The Next keyword defines the next node to jump to after the node being defined. It is used in conjunction with node types Link and Prompt.

Work The Work keyword indicates a sequence of one or more operations to perform when arriving at the node being defined. This processing occurs before speech playback begins.

A select set of math functions, relational operators, and nested if-then-else statements are supported. A pound sign ('#') or a hyphen ('–') in the first position on a new line will cause the translator to skip over the rest of the line. This is useful for inserting comments, or delimiting between individual node definitions. The translator also disregards blank lines.

In order for a node to be properly defined, a minimum number of keywords must be present for each node, and other keywords must be included depending on the node type. The minimum keyword set for a properly defined node is:

Node, Parent, Type, and Play.

Dependency rules:

(1) The Menu type requires at least an @1 line and an @2 line.
(2) The YesNo type requires an @1 and an @2 line (@3, etc. are ignored).
(3) The Link type requires a Next line.
(4) The Prompt type requires a Digits line and a Next line.

The first keyword in a node definition must be Node. The other keywords may be given in any order. The next occurrence of the Node keyword will invoke a completeness test. If the completeness test is successful, then the node definition is saved in machine readable (binary) format, and translation continues with the new Node line. A set of reserved language keywords is listed in Table 1.

TABLE 1

Reserved language keywords (case insensitive):

| @ | link | return |
|---|------|--------|
| and | menu | test |
| digbuf | meta | then |
| digits | next | type |
| else | node | wait |
| essf | parent | write |
| flush | play | work |
| hangup | pop | xor |
| help | prompt | yesno |
| if | push | |
| keep | reenter | |

V. Run-Time Operation

Figure 4:
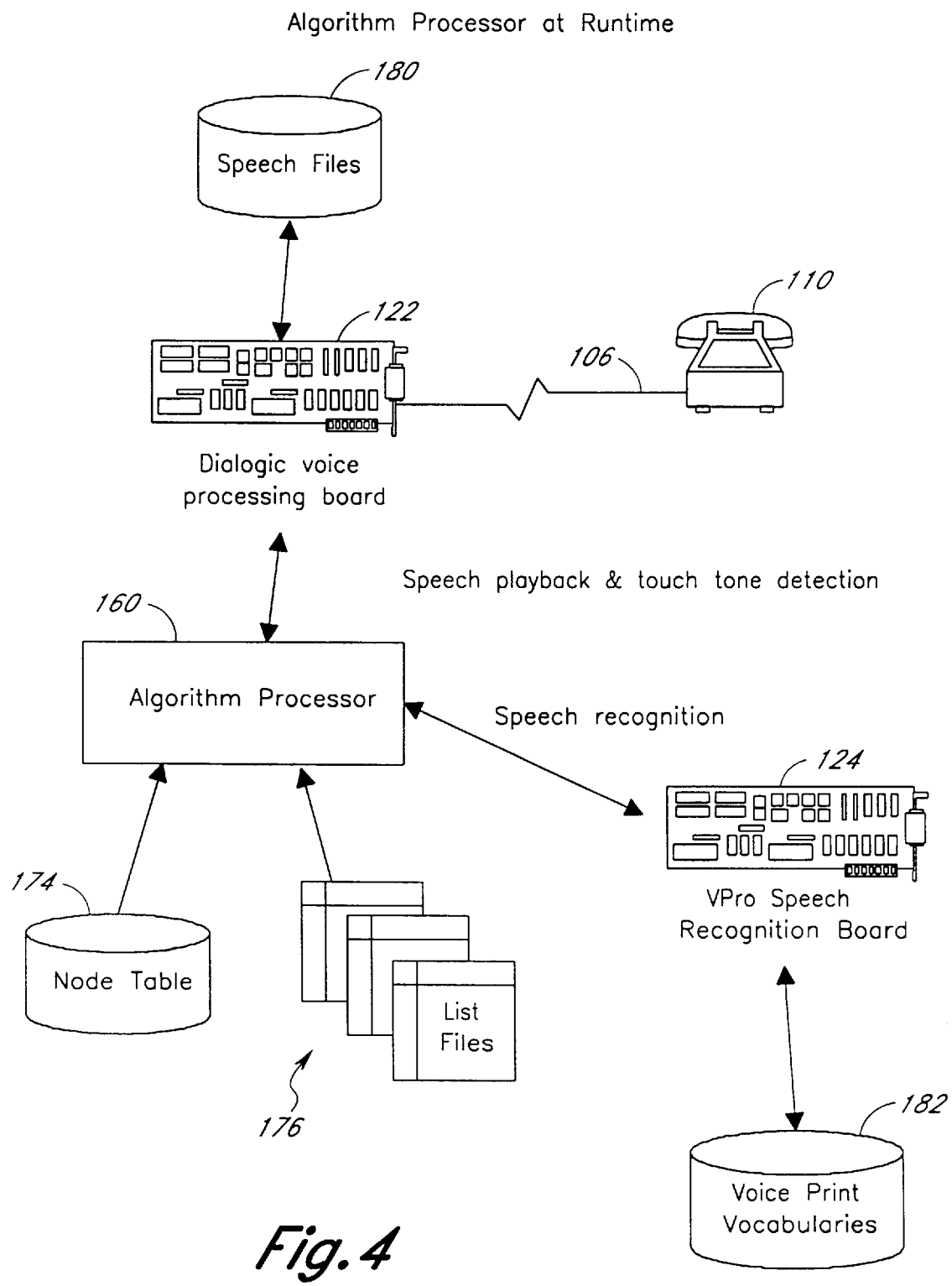
FIG. 4 is a diagram of some of the files and components of FIGS. 1 and 3 that are utilized at run time.

Referring to FIG. 4, the run time interaction among the hardware and software components of the MDATA system 100 will be described. As previously mentioned, algorithm processor 160 includes the parser and supporting functions that manipulate the memory variable symbol table and the run time stack. For a selected medical algorithm, a node record is read from the node table 174 and a list file is read from the plurality of list files 176. The algorithm processor also interacts with the Vpro voice recognition (VR) board 124 for speech recognition and with the Dialogic voice processing (VP) board 122 for speech playback and DTMF detection. The VP board 122 further is interconnected with a set of speech files 180 that are stored on a portion of hard disk 152 and with one of the telephone lines 106 that connects via the telephone network 108 (FIG. 1) to the patient's telephone 110. The VR board 124 further connects with the voice print vocabularies 182, previously described, also stored on a portion of hard disk 152. The algorithm processor 160 utilizes the speech recognition, speech playback, and DTMF detection resources as directed by the medical algorithm that is retrieved from the node table 174 and the list files 176.

Figure 5A:
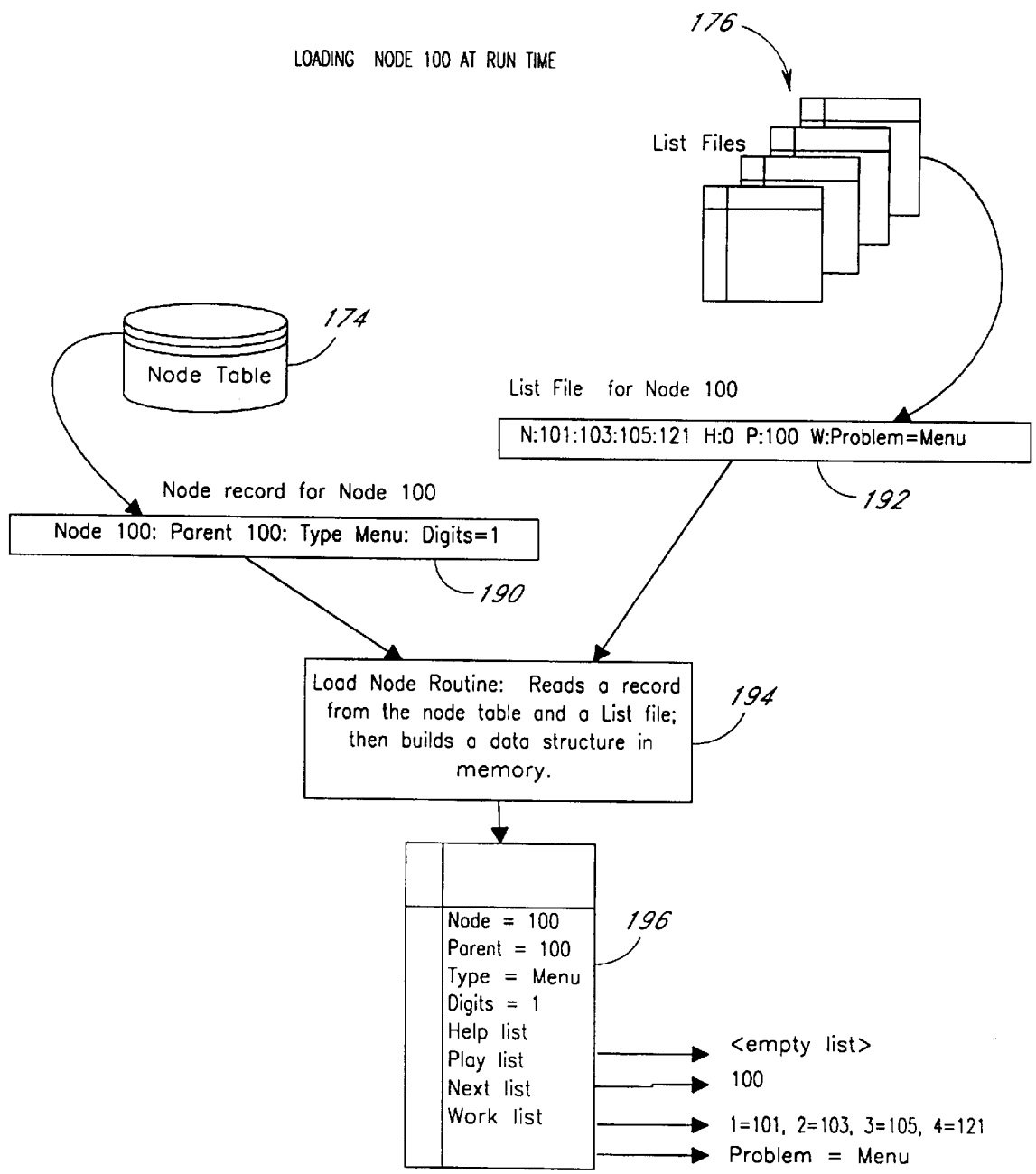
FIG. 5a is a diagram of the utilization of the files shown in FIG. 3 at run time.
Figure 5B:
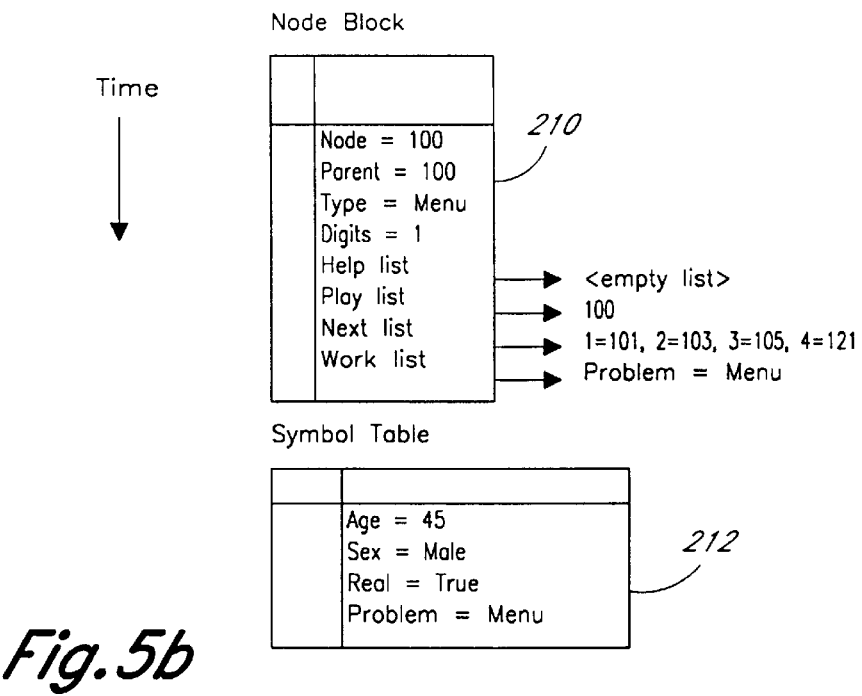

Referring to FIGS. 4, 5a and 5b, several data structures are utilized at run time. These data structures are described as follows:

A. Port Status Block (PSB). A port status block is created at run time for each VP board 122 channel. The PSB contains flags, buffers and tables that hold the state information of the channel, retain responses from the caller, and keep track of where to transfer control in response to voice recognition and telephony events. The PSB keeps track of whether the caller prefers to use spoken or touch tone responses, the caller's last response, the number of consecutive errors the caller has made, and other context sensitive parameters.

B. Node Block. This structure 196 contains the node number, the type attribute (link, menu, yes/no, hangup, prompt, wait, return) and pointers to:

a. Help list—a Play list of help information;
b. Play or Message list—a list of one or more messages or speech files to play in sequence at each node;
c. Next table or list—contains entries for each possible response to a yes/no or menu node that are evaluated at run time to determine the next node to branch to; and
d. Work list—things to do before message playback starts.

The load_node( ) routine 194 in util.c builds the node block structure 196 in memory by first reading in a node record 190 from the node table 174. Then linked lists are attached to the pointers help, play, next and work. These lists come from the list files 176, in subdirectory path \list\listxx\xxyy, where xxyy is the node number, wherein each list file 192 is associated with a unique node.

C. Symbol Table. Each patient has their own associated symbol table. A portion of a symbol table 212 is shown in FIG. 5b. The symbol table is loaded at run time with memory variables that hold patient specific data (age, sex, and items from medical history) and algorithm specific data. The items in the symbol table can be flagged for storage to the patient's medical history.

D. Run Time Stack (RTS). Each Dialogic VP board 122 channel has a RTS associated with it. The RTS is used by the parser. The algorithm programmer can push to and pop from the RTS, e.g. to temporarily store a value of a variable.

The work list has the non-playback tasks that are performed at each node. There is one work list for each node, and it is identified with the work keyword in the ASCII node definition file. The work list may be empty. Each time the system transits to a new node, it will execute the work list. If the patient repeats a node, the system will not execute the work list again; it will simply replay the message(s). If the patient requests the system 100 to back up the node map, the system will execute the work list of the node it backs up to. Typical tasks in the work list involve manipulating objects on the run time stack or in the symbol table, testing for the presence of memory variables, configuring past medical history or current medical condition objects, or writing database records. An example of a complex work list follows:

"Test OBJECT2; Phone=DIGBUF; Push Age" This example tests for the presence of a patient record object labelled "OBJECT2", loads the contents of the digit buffer into memory variable Phone, and pushes the value of memory variable Age onto the run time stack.

Each node has the "next" table or list. The next list indices range from 1 to 9, inclusive. The next list contains either a single node number, or an if expression. For all node types, except the Hangup node, there will be at least one next list:

Link and Prompt nodes: the next node is stored at table index 1.
Yes/No node: the next node for the Yes response is stored at table index 1, and the No response is stored at index 2. This corresponds to the prompt, "if the answer is yes, press 1; if no, press 2."
Menu node: the response number and the table index are the same. Even though the actual data structure has a '0' index in the C programming language, this index is not used in the next table because a '0' response is reserved for operator assistance.

Following is an example of a next list:
"If Male and Age>55 then 100 else 200" is interpreted as: If the patient is both male and over 55 years old then go to node 100 else go to node 200.

Speech files 180 may be of an arbitrary length. A message may be informational, a list of menu options, or a yes/no question. A "two paragraph" or "under one minute" limit has been adopted as a style convention for the presently preferred embodiment. Typically, a node is programmed as a sequence of Yes/No nodes, with "informational" Link nodes interspersed as needed. When there is a lengthy discussion, the speech is recorded in multiple files. To simplify algorithm programming and enhance readability (viz., eliminate long chains of link nodes), the Link node's play list may contain up to ten message numbers.

Upon arrival at a Link node, the system positions a "current message" pointer at the beginning of the play list (trivial case: single message play list; interesting case: multiple message play list). As playback proceeds, the current message pointer moves down the play list. After the system plays the last message on the list, it moves on to the next node.

If the caller issues a "backup" command, the system will move the current message pointer back one message, and resume playback. If the pointer was at the beginning of the list (e.g., trivial case), the system backs up to the previous node and places the current message pointer at the beginning of the play list. If there is more than one message in the list, the system cues the pointer to the last message in the list. The system then resumes playback. In the "pause" mode, when the caller issues the "continue" command, the system will resume playback at the current message.

The MDATA system 100 uses three basic operating modes:

A. Real Mode—involves an actual medical problem. In this mode the system 100 loads the past medical history, saves new past medical history objects, and writes a meta record for each algorithm consulted. The medical algorithm programmer is responsible for providing code to jump past meta analysis in Information mode.

B. Information Mode—involves a "what if" scenario. In the Information mode the system 100 disregards past medical history, does not save newly configured past medical history objects, does not write a meta record for each algorithm consulted, and does not perform meta analysis. The patient has an option in Information mode to change the age and sex parameters to emulate a hypothetical patient.

C. Pending Mode—handles the situation when a patient's voice sample does not match the patient's reference sample. Pending mode is utilized also when an assistant is interacting with the MDATA system 100 on behalf of a patient and both the assistant's and the patient's voice samples fail the voice printing test. In the case where the assistant's voice sample fails the voice printing test but the patient's voice sample passes the test, Pending mode is not utilized. In Pending mode, the MDATA system 100 considers the patient's medical history and performs meta analysis during this consultation. However, a meta record is not written for this consultation and any new medical information gathered on this patient will not be written to the patient's medical record. The new medical information is written to a "Pending" file. The Pending file is verified off-line by a system administrator or staff person, and then is added to the patient's medical record only if the information can be verified.

One of the drawbacks of the traditional doctor-patient relationship is the short amount of time that physicians are able to spend with patients. The MDATA system 100, however, allows patients as much time as they wish to learn about their problem as well as to obtain information on any number of other medical topics.

Through the "Information mode" feature of the MDATA system 100, callers can learn about a disease process, an illness or the latest treatment for any disease, without adding any information to their personal medical record. Although the system 100 keeps track of the interaction, it is labeled as an "Information mode session." The record of the caller's path through the system is not used as the basis for any future advice, nor is it considered in generating system statistics.

The Information mode is not limited to complaints for which the MDATA system 100 offers medical advice. Information about early detection and treatment of many other diseases as well as the latest advances in medicine can be made available through the Information mode.

Referring to FIGS. 5b through 5g, as an example, a run time sequence of steps of how a patient may traverse a main menu node map several steps into a chest pain algorithm node map will be described. A portion of the main menu node map with associated script, and of the chest pain algorithm node map with associated script is included in the Microfiche Appendix. Six nodes with a portion of an associated symbol table will be discussed.

At FIG. 5b, the algorithm processor 160 loads the first node #100, represented by node block 210. The variables for Age, Sex, and Real mode were loaded into the symbol table 212 during the login process (which will be described hereinbelow). Throughout this example, the help list is empty, i.e., no help information is played for the patient. The work list sets the Problem variable of the symbol table 212 to be Menu. Then the system 100 begins playback of message #100. This message gives the patient a menu of choices to choose from. The Digits entry equal to one means that a one digit response is expected from the patient. The patient may respond by pressing a touch tone (DTMF) key on the telephone or speak the choice response into the telephone handset microphone. In this example, the patient selects menu option "1". The parser evaluates the Next list based on the patient selection and branches to node #101.

Figure 5C:
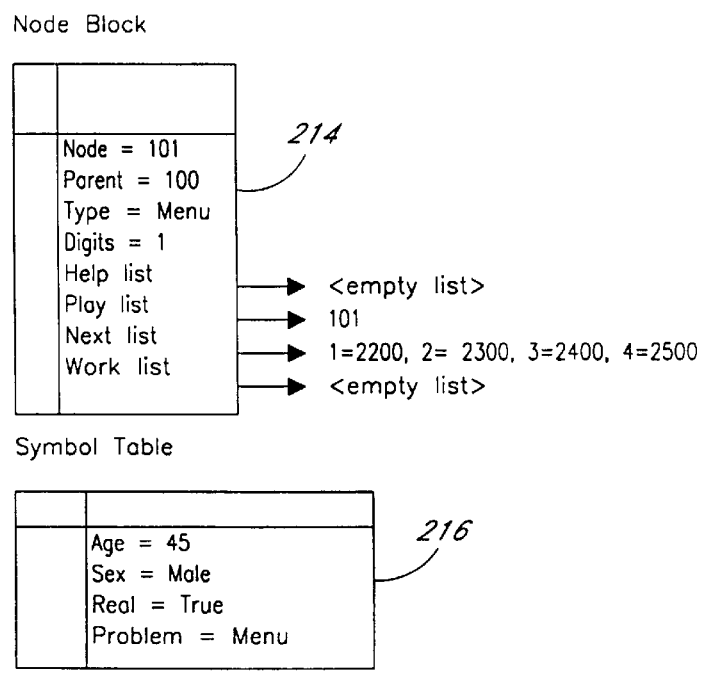

At FIG. 5c, the algorithm processor 160 loads node #101, represented by node block 214. The work list is empty, so the system 100 goes right to playing back message#101 which presents another menu of choices to the user. The Next list has four nodes for possible branch points. In this example, the patient selects menu option "1" for a chest pain complaint. The parser evaluates the Next list based on the patient selection and branches to node #2200.

At FIG. 5d, the algorithm processor 160 loads node #2200, represented by node block 218. The work list command is to update the value of Problem in symbol table 220 to CCHP (chest pain). Then the system 100 begins playback of message#2200. No response is required from the patient for a Link type node. The Next list has two nodes for possible branch points depending on the value of symbol table variable Real. The parser evaluates the If expression in the Next list for the value of Real and, in this example, branches to node #2201.

At FIG. 5e, the algorithm processor 160 loads node #2201, represented by node block 222. The work list command is to write a Meta consultation record for future use by a Meta function. The play list is empty so no message is played. No response is required from the patient for a Link type node. The main purpose of this node is to write the Meta consultation record (because the system is currently in Real mode for this patient). The Next list has only one node so no decisions are necessary by the parser which, in this example, branches to node #2205.

At FIG. 5f, the algorithm processor 160 loads node #2205, represented by node block 226. The work list is empty in this node so the system 100 goes right to playing back message #2205 which presents a yes/no type of question to the user. The Next list has two nodes for possible branch points depending on the response of the patient. In this example, the patient responds "no", and the parser evaluates the Next list based on the patient selection and branches to node #2210.

At FIG. 5g, the algorithm processor 160 loads node #2210, represented by node block 230. The work list is empty in this node so the system 100 goes right to playing back message#2210 which presents a yes/no type of question to the user. The Next list has two nodes for possible branch points depending on the response of the patient. If the patient answers "yes" to the question, the parser branches to node #2211, but if the patient answers "no" to the question, the parser branches to node #2215.

VI. Software Structure

Figure 6:
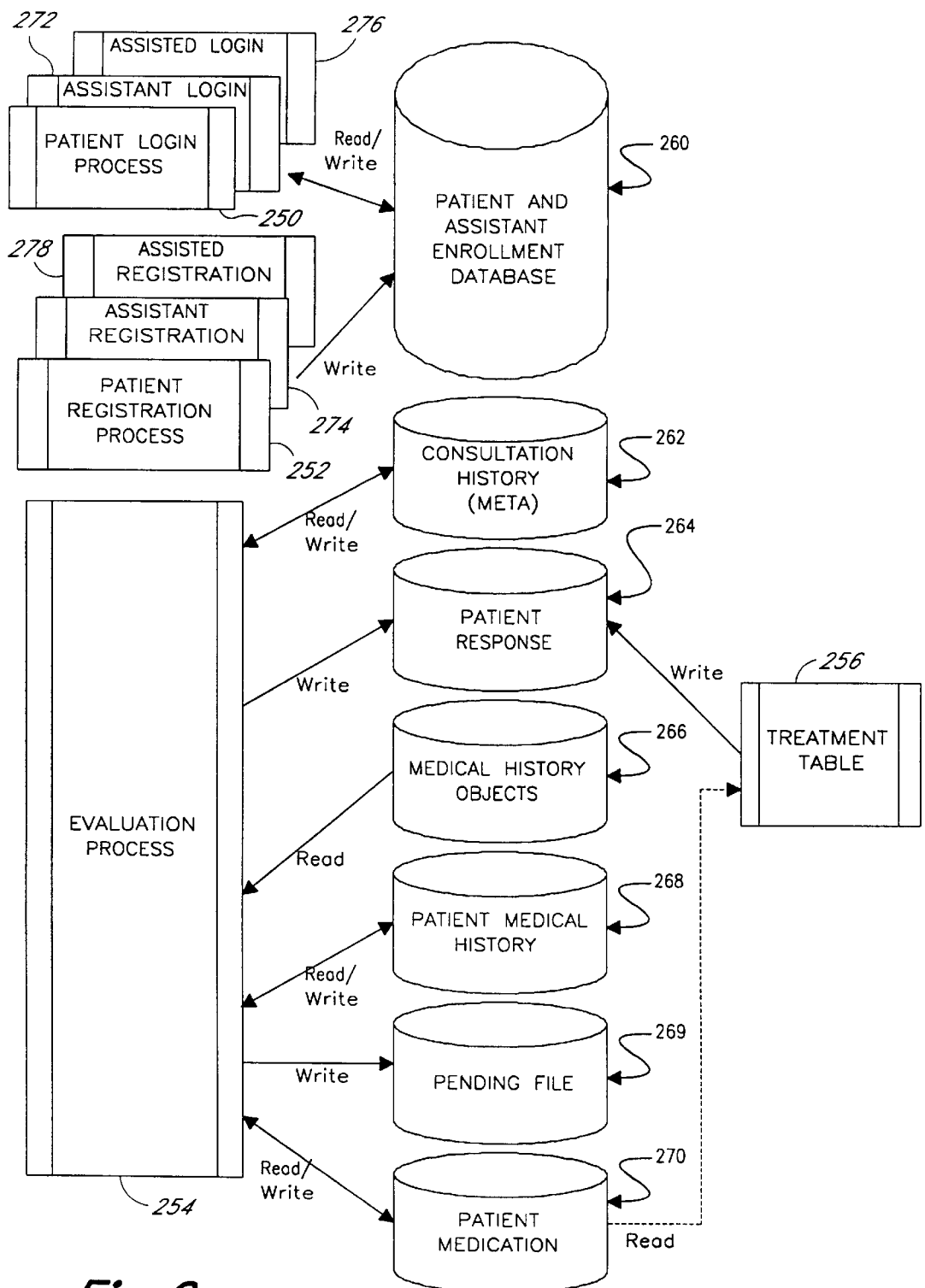
FIG. 6 is a block diagram illustrating a conceptual view of the database files and processes of the system of FIG. 1.

Referring to FIG. 6, the system utilizes eight principal, separate processes and seven related databases. A patient login process 250 is used by the system 100 to identify a patient who has previously registered into the system by prompting for a patient identification number (PIN). An assistant login process 272 is used by the system 100 to identify an assistant who has previously registered into the system by prompting for an assistant identification number (AIN). An assisted patient login process 276 is used by the system 100 to identify a patient who has previously registered into the system by prompting for the patient identification number. If the caller is the patient, a patient registration process 252 is used by the system to register new or first-time patients. If the caller is not the patient, an assistant registration process 274 is used by the system to register new or first-time assistants. Then, if the patient is not already registered, an assisted patient registration process 278 is used by the system to register the patient. These processes will be further described hereinbelow.

Once a caller has logged in or registered, the system provides a choice of two other processes in the current embodiment. The first of these processes is the evaluation process 254 that performs a patient diagnosis. The second of these is a treatment table process 256 to obtain current treatment information for a particular disease or diagnosis. In another embodiment, other choices are added to access other medical information processes.

Associated with these eight processes are a patient and assistant enrollment database 260, a consultation history database 262, a patient response database 264, a medical history objects database 266, a patient medical history database 268, a pending database 269, and a patient medication database 270 that are described as follows:

A. The master patient and assistant enrollment database 260 is created at run-time by one of the registration processes 252, 274, or 278. This database 260 is read by the patient login process 250 or the assisted patient login process 276 to validate a patient's identity at login time and by the assistant login process 272 to validate an assistant's identity at login time. The database 260 is essentially a master file of all registered patients and assistants indexed by their patient ID number or assistant ID number, respectively. The patient ID or assistant ID, date of birth and gender fields are entered by the on-line registration process; the system administrator manually enters the name of the patient or assistant in an off-line manner.

The patient and assistant database 260 contains one record for each patient or assistant. This database 260 is indexed by the identification number. The system appends the enrollment database 260 after a caller is successfully registered. The "next ID number" is stored in a binary file, config.fos, and is incremented after each successful registration. Each record has the following fields:

| Field Name | Data Type | Width | Usage |
|---|---|---|---|
| ID | Numeric | 10 | ID number |
| TYPE | Character | 1 | User type: "P" - patient, "A" - assistant |
| ASST_PERM | Boolean | 1 | Permanent assistant flag |
| ASST_EXP | Date | 8 | Expiration for permanent assistant |
| RELATIONS | Pointer | 20 | Pointers to related patients/assistants |
| ORGZTN | Character | 8 | Organization alphanumeric code |
| NAME | Character | 20 | Patient/Assistant name |
| SEX | Character | 1 | Gender |
| YEAR | Numeric | 4 | Year of birth |
| MONTH | Numeric | 2 | Month of birth |
| DAY | Numeric | 2 | Day of birth |
| ACCESS | Date | 8 | Last access |
| RV_PATH | Character | 20 | Path name of recorded voice file |

B. The consultation history or meta database 262 is created at run-time by the evaluation process 254. A consultation record contains alpha-numeric codes for the patient's complaint, the affected anatomic system and the diagnosed cause of the patient's complaint. When the meta function is invoked at run-time, it compares alphanumeric strings provided by the evaluation process with the fields of all the patient's meta records that fall within a time window specified by the evaluation process. The meta function returns the number of matches found, and an indication of the frequency of the patient's complaint.

Each patient has an individual meta file that is part of the consultation history database 262. At the conclusion of the evaluation process and dependent on the run-time operating mode flag, the system will create a new meta record, populate its fields with the information gathered during the evaluation process, and append this record to either the consultation history database 262 or the Pending file 269. For example, information used in the new meta record may come from a "Write Meta" command in a node Work list. Each record has the following fields:

| Field Name | Data Type | Width | Usage |
|---|---|---|---|
| DATE | Date | 8 | Date stamp |
| PROBLEM | Character | 5 | Patient complaint/symptom |
| SYSTEM | Character | 5 | Anatomical system affected |
| CAUSE | Character | 5 | Diagnosed cause of complaint |

C. The patient response database 264 is created at run-time by the evaluation process 254. The response database 264 is an audit trail: each record is time stamped and registers the patient's response to each question. This database 264 can later be analyzed off-line with a database program such as FoxPro/FoxBase to reveal how the patient responded to questions during the evaluation process 254, or a database program can be developed to gather response patterns and statistics and generate appropriate reports.

Each patient has a response trace file that is part of the patient response database 264. The system 100 appends this response trace file with a response record every time the patient answers a question or provides algorithm-requested data. For human readability, the system also inserts "Begin Call" and "End of Call" records in this file. Each record has the following fields:

| Field Name | Data Type | Width | Usage |
|---|---|---|---|
| DATE | Date | 8 | Date stamp MM/DD/YY |
| TIME | Character | 8 | Time stamp HH:MM:SS |
| NODE | Numeric | 6 | Current node number |
| TYPE | Character | 5 | Response type: DTMF or VOICE |
| RESP | Character | 5 | Response command or digit string |
| MODE | Character | 1 | Consultation operating context |
| VERSION | Character | 20 | Version or Begin/End call comment |
| SENS_FACT | Character | 20 | Current sensitivity factor settings |

D. The medical history objects database 266 is an auxiliary database that supports a key feature of the MDATA system 100: past medical history. The medical history objects database is a catalog of unique alphanumeric codes, each code corresponding to a medical condition or diagnosis that is not expected to change during the life of the patient (e.g., a diagnosis for asthma is coded as "RWHZAST").

In addition to the alphanumeric codes, the MDATA system 100 uses the "memo" field in a Foxpro database to store binary objects. Currently, these binary objects are clinical sounds obtained from the patient over the telephone.

It is anticipated, that as database technology gets more sophisticated (moving toward multi-media and so forth), it will allow storing of larger and more complicated binary files such as the following: a digitized x-ray, a digitized CAT scan, a digitized MRI scan. In addition, as video-telephone technology advances, it is anticipated that the system 100 will store video images or even holographic images of the patient. For every past medical condition there is a record in the medical history objects database that contains the attributes of the medical condition, and contains a pointer into the past medical history questionnaire. The attributes of a medical condition include its data type (e.g., boolean or numeric) and the number of digit positions needed to store the value of a numeric value associated with this condition (not applicable to boolean type).

The pointer field is useful for obtaining medical history at run-time. If a patient has an incomplete medical history questionnaire on file with the MDATA system 100, then the pointer field allows the evaluation process to momentarily suspend the evaluation, go to the medical questionnaire and ask an individual question, collect and verify the patient's response, and then resume the evaluation process. This "ask-when-you-need-it" approach relieves the new patient of going through an exhaustive medical history questionnaire before the first consultation of the diagnostic process.

Each record of the medical history objects database has the following fields:

| Field Name | Data Type | Width | Usage |
|---|---|---|---|
| LABEL | Character | 8 | Object code name |
| TYPE | Character | 1 | Object data type |
| DIGITS | Numeric | 3 | Maximum number of digits in response |
| CALL | Pointer | 6 | Identifies question(s) to be asked to configure this object |
| AUDIO | Binary | N/A | Voice print |
| IMAGERY | Binary | N/A | Face print |
| RFU | Character | 20 | (For future use) |

E. The patient medical history (PMH) database 268 is created at run-time by the evaluation process 254 or by use of a past medical history questionnaire. The PMH database 268 is read by the evaluation process during run-time. This database 268 contains each patient's individual medical history. A new patient has an option to go through the entire medical questionnaire at one time, thereby configuring all the past medical history objects listed in the objects database 266. Alternately, the new patient can bypass the questionnaire and go right into the diagnosis of a medical complaint. Then, if a medical algorithm requires a past medical history object that has not yet been configured, the evaluation process 254 invokes a past medical history function before it continues with the algorithm.

Each patient has their own past medical history file, which is part of the PMH database 268, that contains records which describe medical events or conditions from the patient's life. The system 100 appends a record to this file each time a past medical history object is configured for the patient. The contents of this file are installed in the symbol table when the patient logs in to the system 100. The medical algorithm programmer is responsible for using a TEST command to verify that necessary items are present in the symbol table before algorithm execution. A side effect of a negative TEST result is that the system 100 prompts the patient to provide that information. The system 100 flags any new or modified items, and asks the patient to confirm these values during an Exit Confirmation Loop which will be described hereinbelow. Each record has the following fields:

| Field Name | Data Type | Width | Usage |
|---|---|---|---|
| LABEL | Character | 20 | The object's label |
| TYPE | Character | 1 | Object data type |
| VALUE | Character | 10 | Object's configured value |
| CERT | Numeric | 3 | Certainty of object's value |
| DATE | Date | 8 | Object configuration date |
| ICD9A | Float | 5 | First ICD-9 code |
| \| | \| | \| | \| |
| ICD9E | Float | 5 | Fifth ICD-9 code |

F. The "Pending" database file 269 holds medical information gathered during Pending mode for offline verification. The Pending database record structure is the same as that used for the past medical history (PMH) database 268. The evaluation process writes to the Pending database at run-time when it configures a new past medical history object for a patient during a Pending mode interaction. The contents of the Pending database are reviewed off-line by a staff person, and if the information is verified, the staff person appends the information to the patient's past medical history file.

G. An optional patient medication database 270 contains a file for each patient containing information about medication they are taking, or have taken in the past. The medication database 270 is created by the evaluation process 254 at run time. A "Write Drug" command builds a record and fills its fields with same-named memory variables from the symbol table. The evaluation process 254 may read the medication database 270 during run time as needed. The treatment table 256 optionally reads the medication database 270 to determine the medication (s) being used by the patient.

| Field Name | Data Type | Width |
|---|---|---|
| GENERIC_NAME | Character | 20 |
| TRADE_NAME1 | Character | 20 |
| TRADE_NAME2 | Character | 20 |
| TRADE_NAME3 | Character | 20 |
| ICD-9-CM_CODE | Character | 10 |
| ICD-9-CM_ECODE | Character | 10 |
| ICD-9-CM_VCODE | Character | 10 |
| OTHER | Character | 20 |
| DOSAGE | Character | 20 |
| ROUTE_OF_ADMINISTRATION | Character | 10 |
| FREQUENCY | Character | 10 |
| USE | Character | 20 |
| START_DATE | Date | 8 |
| STOP_DATE | Date | 8 |
| OTHER1 | Character | 20 |
| OTHER2 | Character | 20 |

VII. Top-Level Flow

Referring to FIGS. 7a, 7b, 7c and 7d, the top level flow 300 of the MDATA system 100 software will be described. The telephone number used to access the MDATA system 100 may vary in various embodiments of the system. If the sponsoring agency or hospital wishes to provide access to the MDATA system 100 at no cost to the caller, then a toll-free 800 service number can be used. If the sponsoring agency or hospital wishes to recover the costs of running the MDATA system 100 from the caller, it may use a pay-per-call or premium charge number (e.g., 900 service). "Current Procedural Terminology" (CPT-4) codes are available to describe and bill third party payers for telephone consultations. They are a listing of the descriptive terms and identifying codes for reporting medical services and procedures. CPT-4 codes are the most widely accepted nomenclature for reporting physician services to insurance companies.

Beginning at a start state 302, a person 112 (FIG. 1) desiring medical advice calls the telephone number for the MDATA system 100 on a telephone line 106. The caller may be the patient or may be an "assistant", e.g., parent, relative, or friend, that is helping the patient. Moving to state 304, the system 100 answers the call automatically and greets the caller 112 with an introductory greeting message by playing back a speech file stored on the hard drive 152 by use of the VP board 122. Proceeding at state 306, the MDATA system 100 asks each patient who calls the system a series of "initial screening questions." These questions are designed to identify patients who are critically ill; they are not designed to identify the patient's problem. The initial screening questions enable the system to filter out patients who require immediate medical attention.

Moving to decision state 308, any patient found to be critically ill is instructed to dial the emergency response telephone number "911" at state 309 or will be automatically connected to the nearest emergency medical services system in the patient's area. The telephone call is terminated by the computer 102 at state 310. The following are examples of initial screening questions:

IS THIS A MEDICAL EMERGENCY?
ARE YOU HAVING DIFFICULTY BREATHING?
ARE YOU EXPERIENCING SEVERE PAIN OR PRESSURE IN YOUR CHEST?

If the system determines that the patient is experiencing a medical emergency, it may provide the patient with a menu of emergency medical procedures at state 311. In situations where the patient or the caller for the patient is far from the nearest emergency help, e.g., a rural setting, the caller may need to initiate emergency procedures immediately. The menu of emergency medical procedures provides several choices to the caller. If the caller presses touch tone key "1" or speaks the word "one" into the telephone mouthpiece, the computer 102 branches to state 312 wherein well known CPR (cardiopulmonary resuscitation) information is recited. If the caller has a speakerphone capability associated with the telephone 110 being used, the caller may be able to listen to and perform the instructions given by the system 100 in a hands-free manner away from the telephone. If the caller presses touch tone key "2" or speaks the word "two" into the telephone mouthpiece, the computer 102 branches to state 313 wherein well known Heimlich Hug information for choking is recited. At the completion of either state 312 or state 313, the telephone call ends at state 314.

Figure 7A:
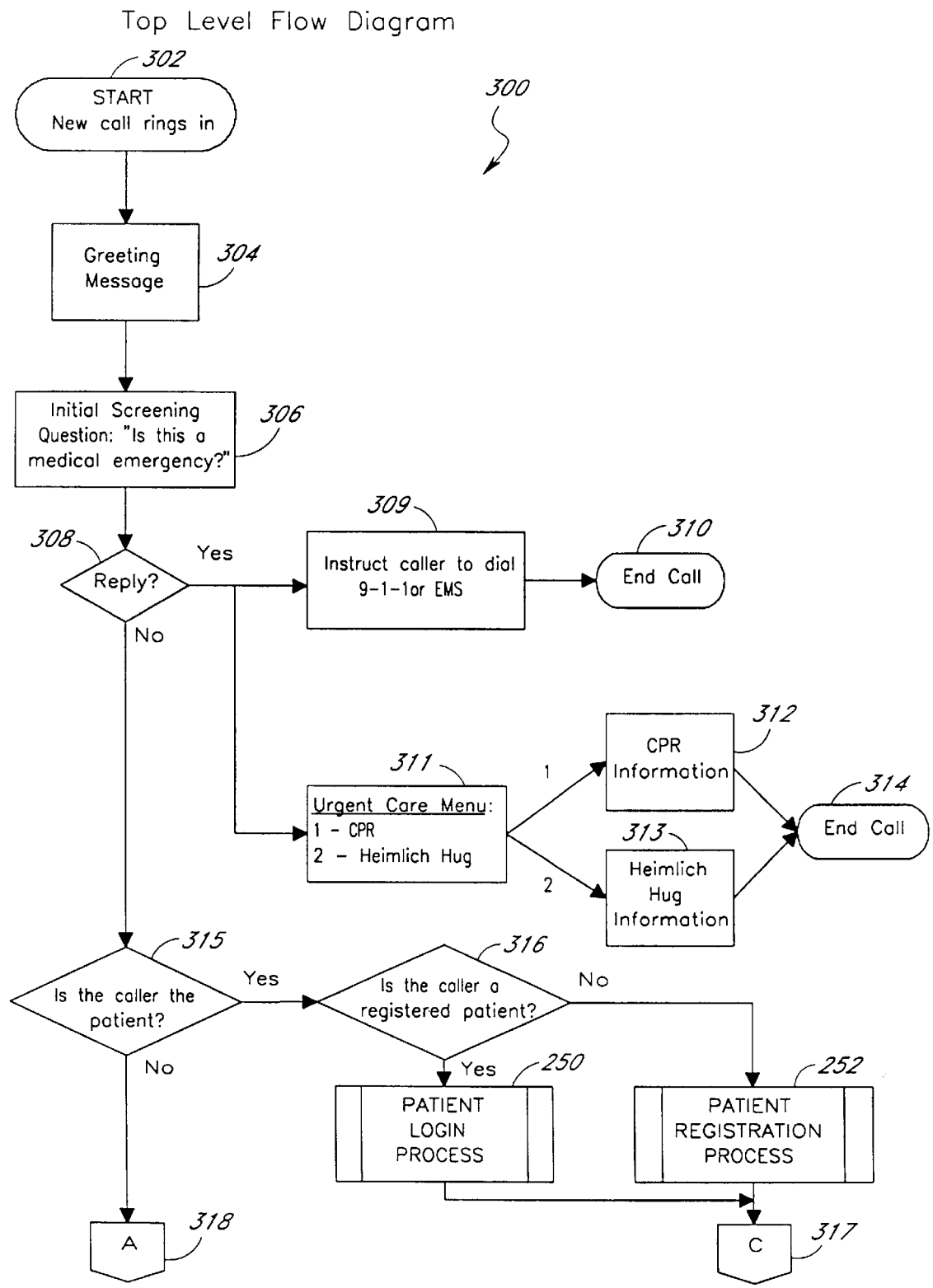
FIGS. 7a, 7b, 7c and 7d are a top-level flow diagram of the MDATA system of FIG. 1.

If the patient is determined at state 308 not to have a medical emergency, i.e., the MDATA system 100 is satisfied that no immediately life threatening condition is present, the computer 102 moves to a decision state 315 to determine if the caller is the actual patient. If so, the computer 102 proceeds to a decision state 316 to determine if the patient has previously registered or ever consulted with the system 100, i.e., is not a new or first-time caller. If so, the system 100 verifies the patient's identification and retrieves their medical record at the patient login process 250, which will be further described hereinbelow. At the completion of process 250, the computer 102 proceeds through off-page connector C 317 to state 344 (FIG. 7d). If the patient is not registered, the MDATA system 100 proceeds to the patient registration process 252 for a new patient, which will be described hereinbelow. At the completion of process 252, the computer 102 proceeds through off-page connector C 317 to state 344 on FIG. 7d.

Figure 7B:
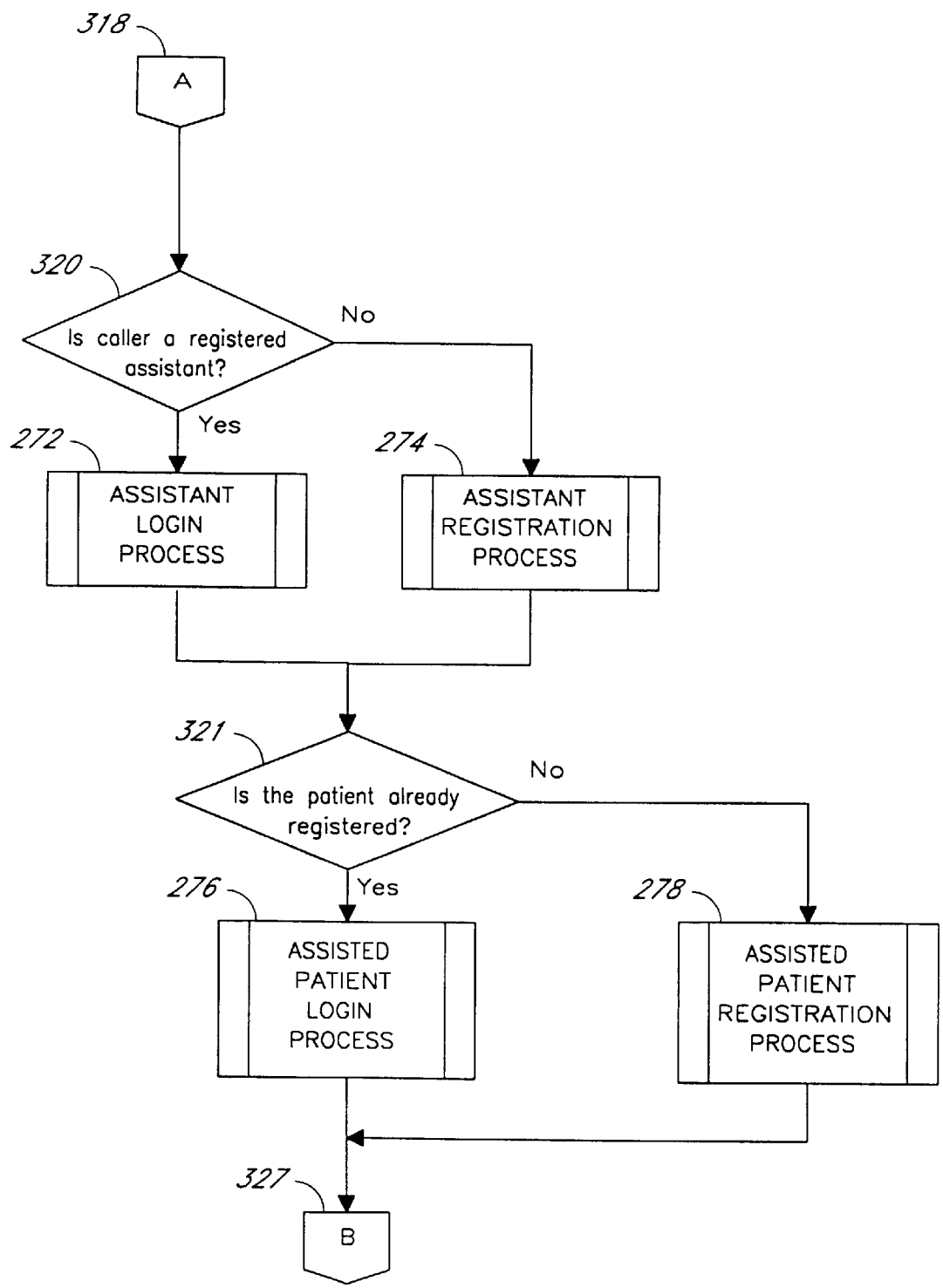
Figure 7C:
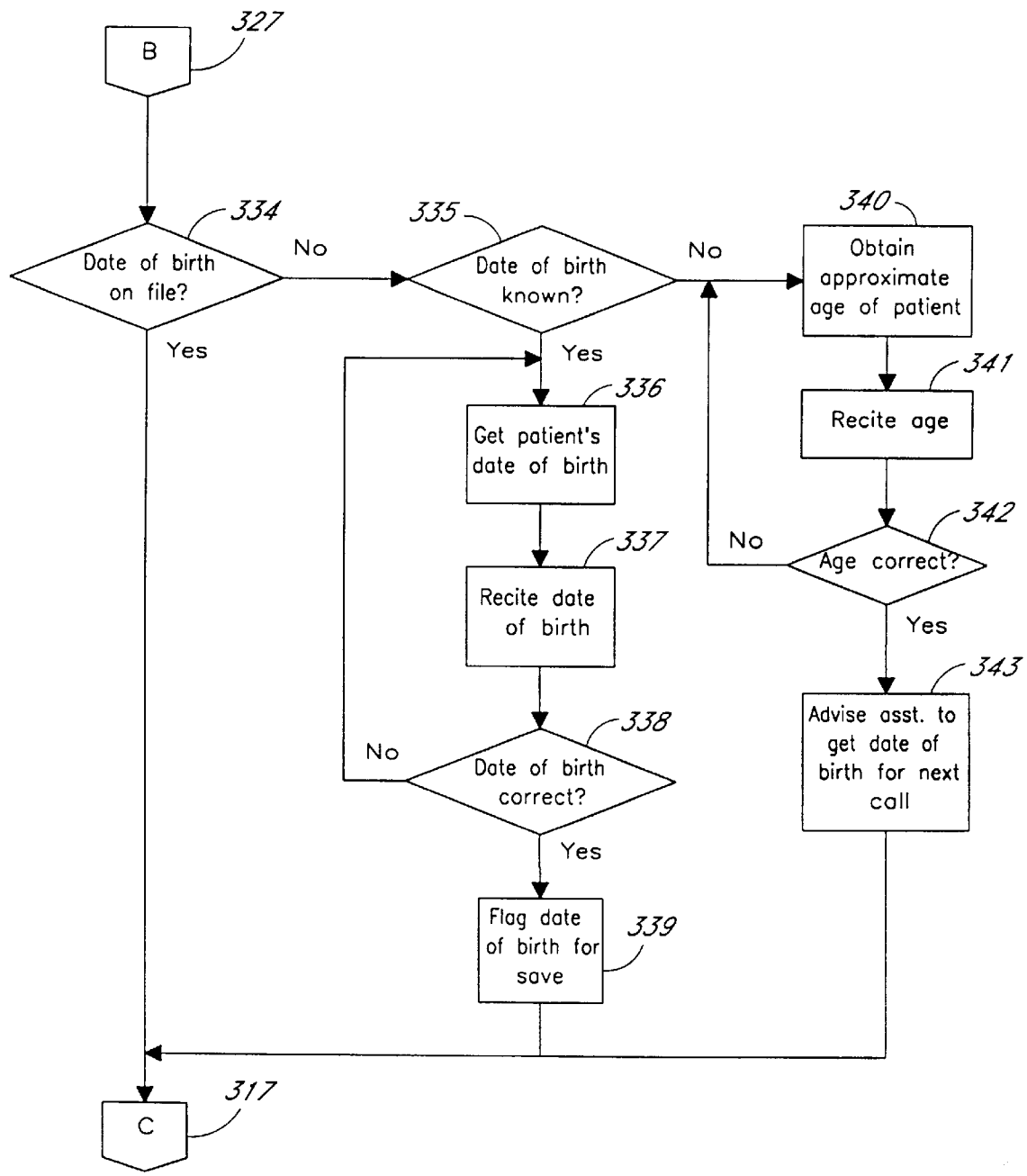
Figure 7D:
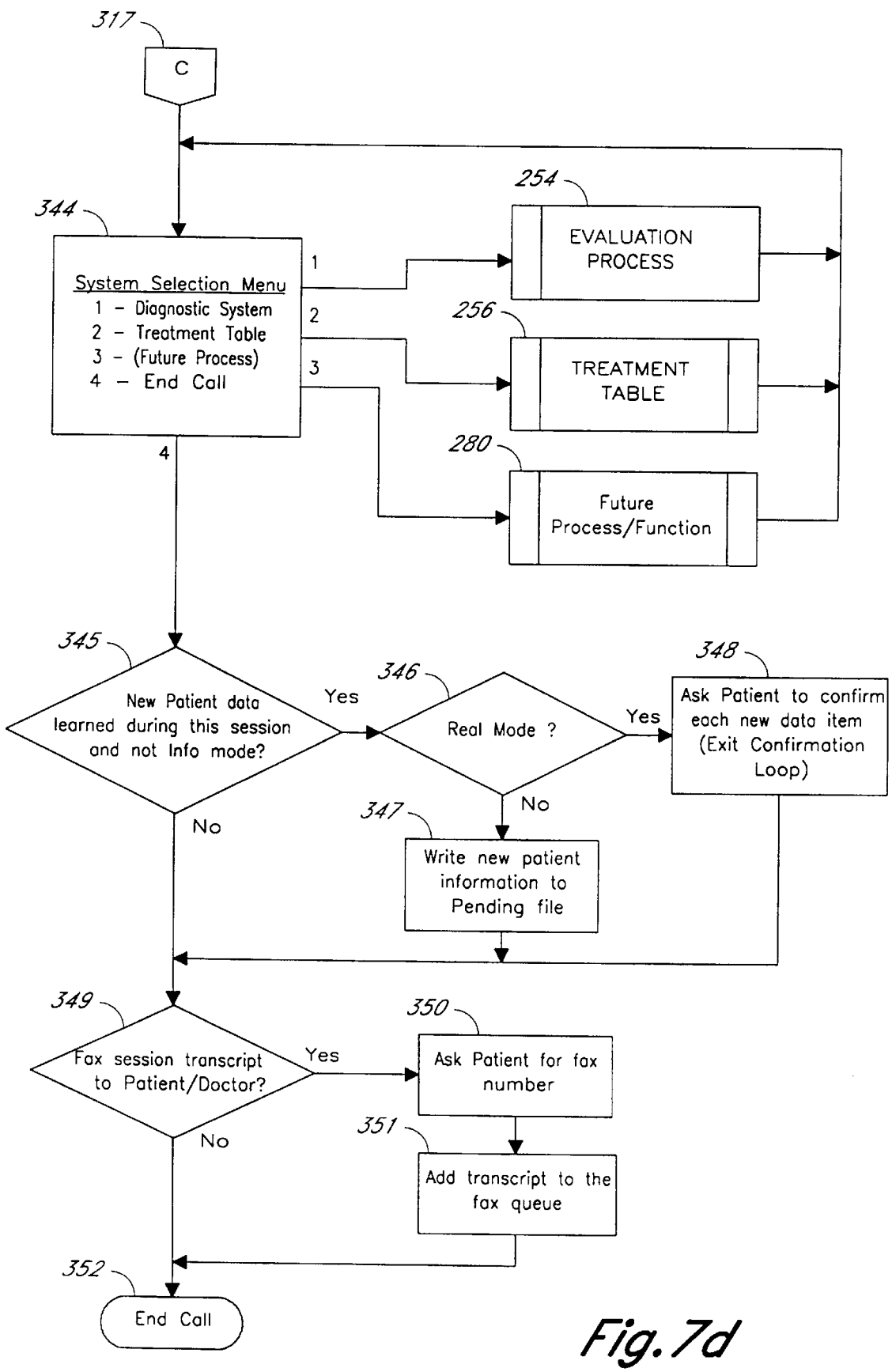

If the caller is not the patient, as determined at state 315, the computer 102 proceeds through off-page connector A 318 to state 320 on FIG. 7b. There will be times when the patient may not be able to use the MDATA system 100 directly, e.g., due to injury, weakness or altered level of consciousness. In these cases, an "assistant" may interact with the system on behalf of the patient.

An assistant registers with the system through the assistant registration process 274 which will be described hereinbelow. The assistant registration record is identical to the patient registration record in structure, but three fields have special significance for an assistant: ASST_PERM, ASST_EXP, and RELATIONS. The ASST_PERM field is a boolean flag that can only be set true off-line by the system administrator who has verified, through separate means, that a relationship exists between a patient and an assistant. The relationships are one-to-many, i.e., a patient may have one or more assistants, and an assistant may be related to more than one patient. The ASST_PERM flag may also be constrained by the ASST_EXP field, which contains a timestamp for the expiration of the ASST_PERM attribute. If the ASST_PERM flag is true, then the RELATIONS pointers will point to one or more patient records for whom this assistant is a "permanent assistant;" otherwise the RELATIONS field will be empty.

The medical information gathered during an assisted consultation is written to the patient's medical record only if the following three conditions are met:

(a) the assistant's ASST_PERM flag is True
(b) the ASST_EXP timestamp has not been reached
(c) the assistant has a relationship pointer to the patient record If any of these conditions are not met, then any new medical information gathered on this patient will be saved to the Pending file 269 for off-line verification by the system administrator.

The system 100 establishes at state 315 whether the caller is the patient, or an assistant. If the caller is not the patient, then the system asserts that the caller is an assistant and, at a decision state 320, determines if the assistant is registered. If the assistant is not already registered with the system, the system enrolls the new assistant at the assistant registration process 274. If the assistant is already registered with the system 100, the computer 102 performs the assistant login process 272. At the completion of either process 272 or process 274, the computer 102 advances to a decision state 321.

If the patient is not already registered with the system 100, as determined at decision state 321, then the system allows the assistant to register a new patient at the assisted patient registration process 278. However, if the patient is already registered with the system 100, as determined at state 321, the computer 102 performs the assisted patient login process 276. At the completion of process 278 or process 276, the computer 102 proceeds through off-page connector B 327 to a decision state 334 on FIG. 7c.

At decision state 334, the computer 102 determines if the patient's date of birth is in the patient's medical record. If so, the computer proceeds through off-page connector C 317 to state 344 on FIG. 7d. If not, the system 100 attempts to get the patient's date of birth. Moving to state 335, the system 100 asks the assistant if the patient's date of birth is known. If so, the computer 102 advances to state 336 to request the patient's date of birth. At state 337, the system 100 recites the patient's date of birth obtained at state 336. At a decision state 338, the assistant determines if the date of birth is correct as recited by the system 100. If not, the computer 102 loops back to state 336 to request the patient's date of birth again. If the patient's date of birth is correct, as determined at state 338, the computer 102 flags the date of birth for saving in the patient's medical record at state 339, and proceeds to state 344 on FIG. 7d.

If the patient's date of birth is not known, as determined at state 335, the computer 102 proceeds to state 340 wherein the system requests the assistant to provide an approximate age of the patient. The age is an important parameter used in the evaluation process 254 and treatment table 256. At state 341, the system 100 recites the patient's approximate age obtained at state 340. At a decision state 342, the assistant determines if the age is correct as recited by the system 100. If not, the computer 102 loops back to state 340 to request the patient's approximate age again. If the patient's approximate age is correct, as determined at state 342, the system 100 advises the assistant at state 343 to get the patient's actual date of birth before the next consultation, and proceeds to state 344 on FIG. 7d. The system 100 uses the approximate age in the consultation during the evaluation process 254 and the treatment table 256.

At state 344 on FIG. 7d, the system 100 presents the caller with a system selection menu. Here, the caller is asked to select from among four choices: diagnostic system, treatment table, a future process/function, or end call as described below:

A. Diagnostic System: The system starts the evaluation process 254 at a menu, where it asks the patient to begin identification of the complaint.

B. Treatment Table: The system takes the patient to the treatment table process 256 at a menu, where it asks the patient to select a treatment selection method.

C. Future Process/Function: A future process or function 280, undefined in the present embodiment, that reads and/or writes the databases shown in FIG. 6.

D. End Call: The system performs several steps and then terminates the telephone call.

In either process 254 or 256, the computer 102 functions as an interpreter as performed by algorithm processor 160 in following the node map created by the algorithm programmer. At the exit point of the evaluation process 254, the system 100 gives the patient the option of selecting another complaint. At the end of the treatment table process 256, the system gives the patient the option of selecting another treatment.

At the completion of the evaluation process 254, treatment table process 256, or future process 280, the system 100 loops back to state 344 and recites the system selection menu to the caller. If the caller chooses the End Call selection at state 344, the MDATA system 100 moves to a decision state 345. At decision state 345, the system 100 determines if process 254, process 256, or process 280 did not occur in Information mode, i.e., did occur in either Real mode or Pending Mode, and examines the patient's symbol table to determine if any of the configured memory variables are past medical history conditions that need to be saved to the patient's medical history file. If both conditions are true at state 345, the system 100 advances to a decision state 346 to determine if the consultation is being performed in Real mode. If not, the consultation is being performed in Pending mode, and the system 100 then writes any new patient information obtained during the consultation to the Pending file 269. If state 346 proves to be true, i.e., Real mode, for each past medical condition that needs to be saved, the MDATA system 100 asks the patient at state 348 to grant permission to save the datum to the patient's medical history file and to confirm that the datum is correct. For example, during a consultation for cough, the MDATA system 100 learned that the patient has been diagnosed as being HIV positive. The system 100 will ask, "May I record the information about your HIV diagnosis in your medical record?" If the patient responds "yes", then the system 100 will ask, "Please verify that your diagnosis for HIV was positive, is this correct?" If the patient responds "yes", then the system 100 writes this fact to the patient's medical history file. After confirmation, each data item is stored in the patient's file in the patient medical history database 268 (FIG. 6).

At the completion of either updating the history database 268 at state 348, state 345 proves to be false, or at the completion of state 347, the system 100 moves to a decision state 349. Before the MDATA system 100 ends the consultation with the patient, it presents a summary of all the advice it has given. The patient is asked to write down and repeat back the key points. The MDATA system 100 then gives the patient the option of receiving a summary of the consultation session and specific recommendations provided by the system by either facsimile or first class mail. If a fax is desired, the system 100 asks the patient for a fax number at state 350. The patient also has the option to send a summary of the consultation to his or her health care provider or specialist. Proceeding to state 351, the computer 102 adds the transcript of the current telephone session to a fax queue for subsequent transmission. At the completion of state 351 or if the system 100 determined at state 349 that the session transcript was not to be faxed, the telephone call is terminated at state 352.

VIII. Login Process

Figure 8A:
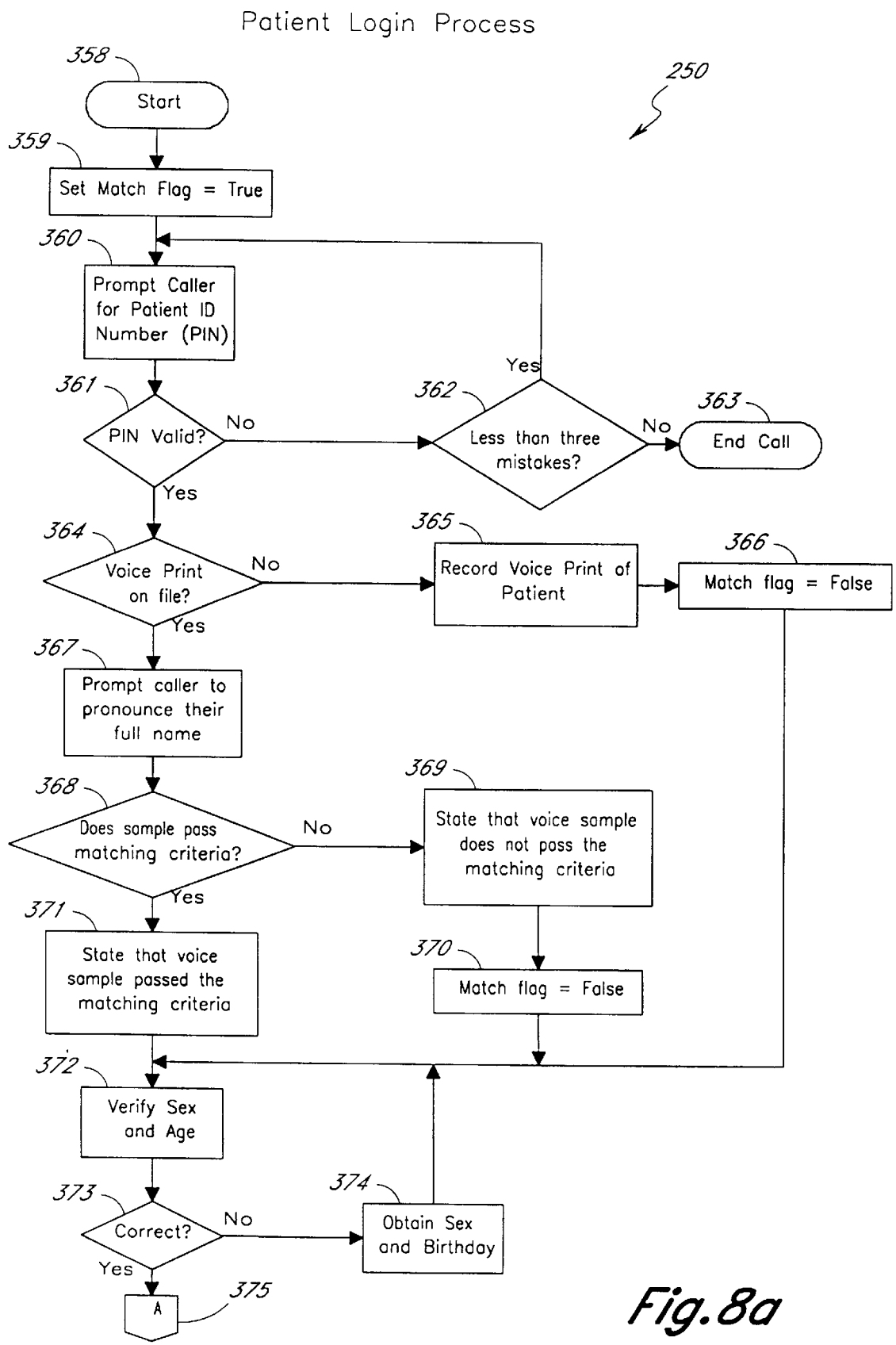
Figure 8B:
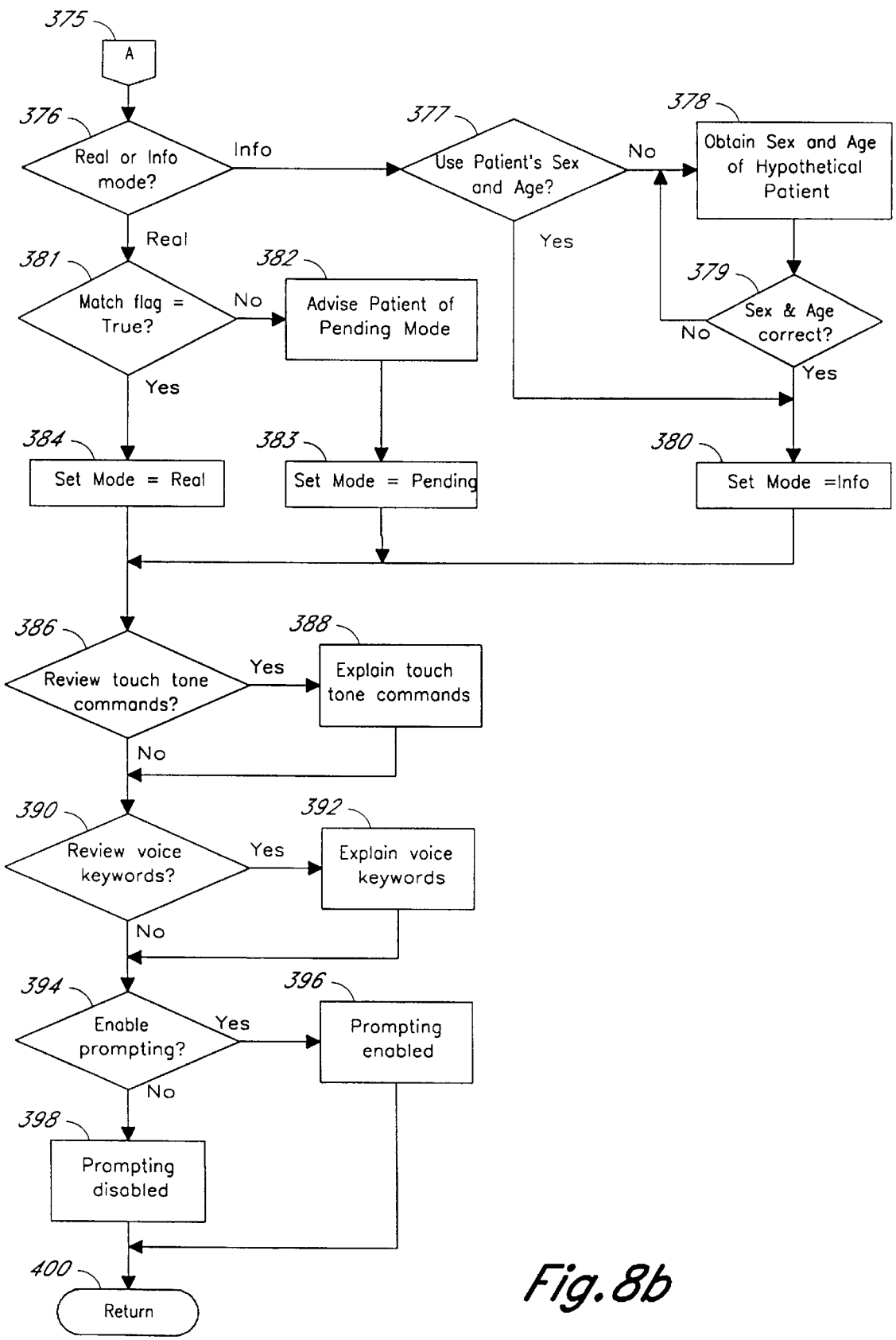

Referring now to FIGS. 8a and 8b, the patient login process 250 defined in FIG. 7a will be described. This process 250 is called if the patient has previously called and registered with the system 100. Beginning at a start state 358, the computer 102 moves to state 359 and initializes a match flag to true. The match flag is checked later in this process 250 in conjunction with setting the mode of the consultation. Proceeding to state 360, the computer 102 prompts the patient for the patient ID (identification) number (PIN) that is assigned during the registration process. The patient registration process 252 will be described in conjunction with FIGS. 9a and 9b. Proceeding to a decision state 361, the computer 102 determines whether the PIN is valid. If not, the computer 102 determines, at a decision state 362, if less than three tries at entering the PIN have been attempted. If so, the computer 102 loops back to state 360 to repeat the request for the PIN. However, if three attempts at entering the PIN have been made, as determined at state 362, the computer 102 plays a polite message that advises the patient that the login attempt failed and terminates the call at state 363. The computer 102 reports the failed login attempt to the system administrator at the sponsoring agency, hospital or other organization. The patient is allowed to reregister as a new patient, however, to permit access to the needed medical information. The system administrator resolves this type of situation off-line.

If the patient has correctly entered a valid PIN, as determined at state 361, the computer 102 moves to a decision state 364 to determine if the patient identified by the PIN has a voice print or sample voice waveform on file in the system 100. If not, the computer 102 proceeds to state 365 to record the voice print of the patient, e.g. the patient's pronunciation of his or her full name. The patient's voice print may not be on file, for example, if the patient could not provide a voice print during the assisted patient registration process 278 in a prior consultation. At the completion of recording the voice print at state 365, the computer 102 advances to state 366 wherein the match flag is set to false to indicate that the patient's voice print was recorded during the current login.

If the patient identified by the PIN has a voice print on file in the system 100, as determined at state 364, the computer 102 proceeds to state 367 and prompts the patient to pronounce his or her full name. Moving to a decision state 368, the computer 102 determines whether the voice sample obtained at state 367 passes the matching criteria. If not, the computer proceeds to state 369 and recites a message that the current voice sample does not pass the matching criteria. In the presently preferred embodiment, the current voice sample is compared to the reference voice sample recorded during the patient registration process 252 or the assisted patient registration process 278. Because the voice samples did not match, as determined at state 368, the computer 102 sets the match flag to false at state 370. In this case, the match flag is set to false to indicate that one of the security checking methods has failed. However, the process 250 continues at state 372 after the match flag is set to false at either state 366 or 370.

If the voice sample passed the matching criteria at state 368, the computer 102 advances to state 371 and recites a message that the current voice sample passed the matching criteria. This security check condition is now satisfied, and the match flag remains set to true. At the completion of state 371 the computer 102 moves to state 372. At state 372, the computer 102 verifies the sex and age of the patient by reciting the sex and age, as stored in the enrollment database 260 (obtained during the patient registration process 252), to the patient. At a decision state 373, the patient responds to the correctness of the recited information. If the sex or birth date information is not correct, the computer 102 moves to state 374 to request the correct information. The computer 102 then proceeds back to state 372 to verify the information received at state 374. If the result of the decision state 373 is true, i.e., the sex and age are correct, the computer moves through off-page connector A 375 to a decision state 376 on FIG. 8b to determine if the patient desires to conduct the telephone session in Real mode or Information mode. If Information mode is desired, the computer 102 moves to a decision state 377 to determine if the patient's sex and age are to be used during the Information mode consultation. If not, the computer 102 moves to state 378 to request an age and sex to use in a hypothetical situation during the Information mode session. Moving to a decision state 379, the computer 102 recites the sex and age obtained at state 378, and asks the patient to confirm that this information is correct. If not, the computer 102 moves back to state 378 to request the age and sex again. When decision state 379 is true or the patient's age and sex are to be used during this consultation, as determined at state 377, the computer 102 moves to state 380 and sets the operating mode to be Information mode.

If decision state 376 is determined to be Real mode, the computer 102 moves to a decision state 381 to check if the match flag is true. If not, the system 100 advises the patient, at state 382, that the current consultation is to be performed in Pending mode. The operating mode is set to be Pending mode at state 383. If the match flag is true, as determined at state 381, the computer 102 sets the operating mode to be Real mode at state 384.

At the completion of setting the operating mode at either state 380, state 383, or state 384, the computer moves to a decision state 386. At decision state 386, the computer 102 determines if the patient desires to review the touch tone commands described during the registration process. If so, the computer 102 advances to state 388 and recites the touch tone commands. At the completion of state 388 or if the patient did not wish to review the touch tone commands, the computer 102 proceeds to a decision state 390 wherein the computer 102 determines if the patient desires to review the voice keywords described during the registration process. If so, the computer 102 advances to state 392 and recites the voice keywords. At the completion of state 392 or if the patient did not wish to review the voice keywords, the computer 102 proceeds to a decision state 394 wherein the computer 102 determines if the patient desires to enable prompting. If so, the computer 102 advances to state 396 and enables prompting. If not, prompting is disabled at state 398. To "enable prompting" means that the patient would like to be prompted for responses. This is referred to as "hard" is prompting, since this will remain in effect for the duration of the call. If hard prompting is off, and the system 100 has difficulty recognizing patient responses, the computer 102 turns on "soft" prompting. After the next successful recognition, the computer 102 turns off soft prompting. At the completion of state 396 or 398, the computer 102 returns at state 400 to the top level flow (FIG. 7).

Figure 12A:
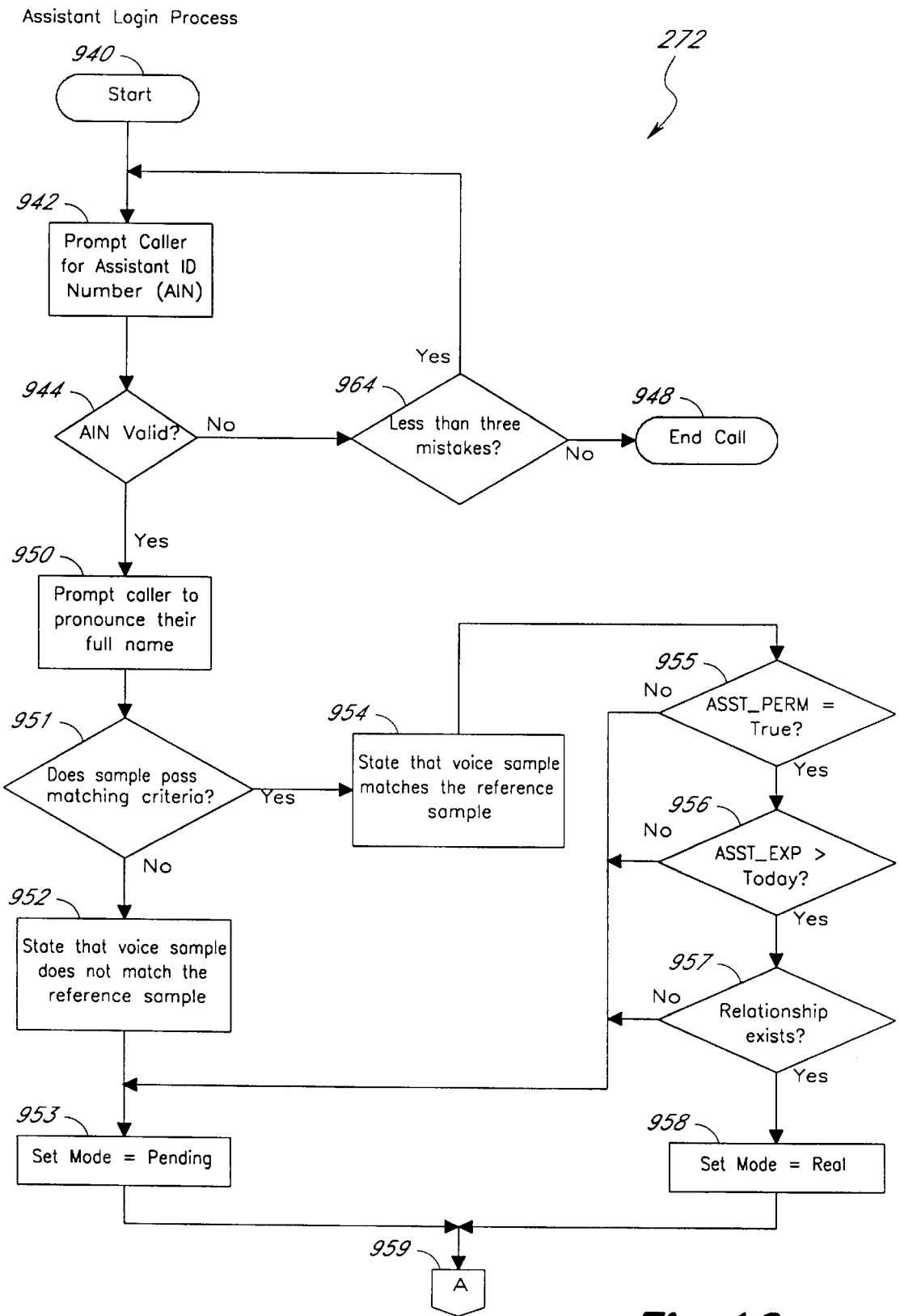
FIGS. 12a and 12b are a flow diagram of the assistant login process 272 defined in FIG. 7b.
Figure 12B:
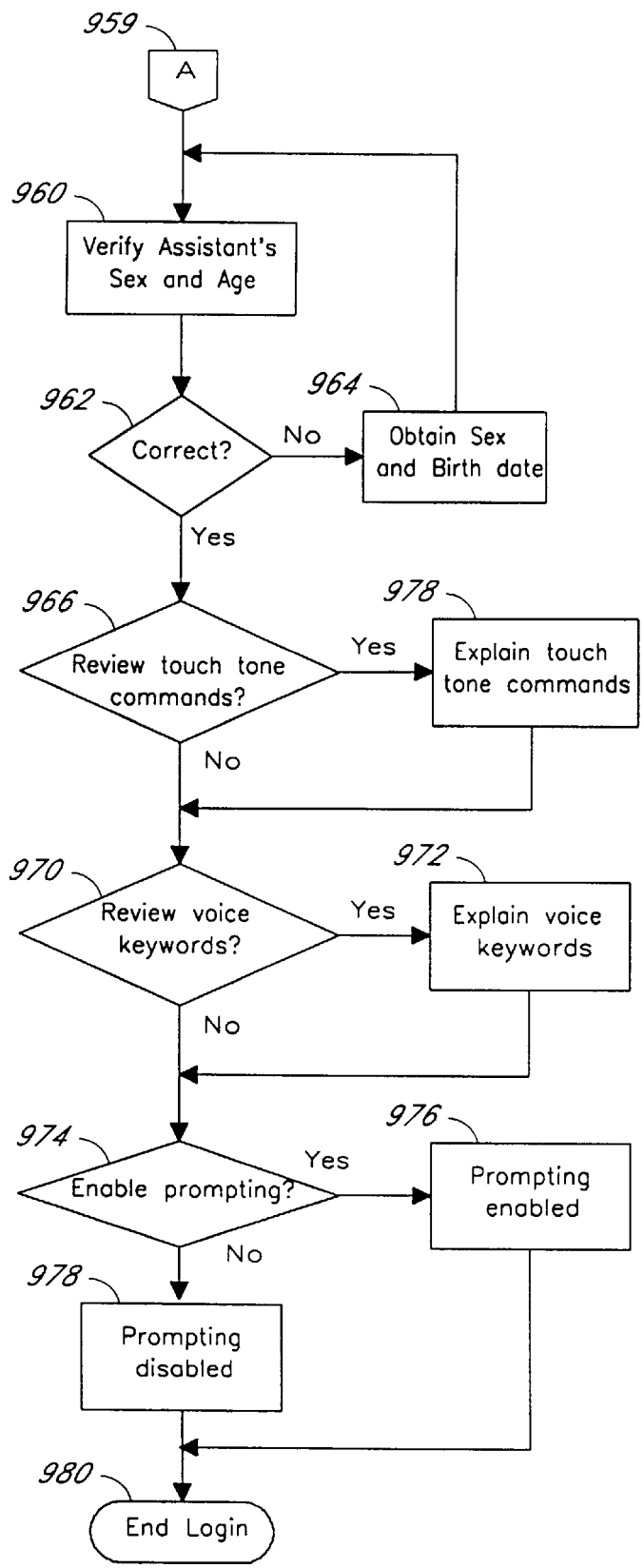

Referring now to FIGS. 12a and 12b, the assistant login process 272 defined in FIG. 7b will be described. This process 272 is called if the assistant has previously called and registered with the system 100. Beginning at a start state 940, the computer 102 moves to a state 942 and prompts the assistant for the assistant ID (identification) number (AIN) that is assigned during the registration process. The assistant registration process 274 will be described in conjunction with FIGS. 14a and 14b. Proceeding to a decision state 944, the computer 102 determines whether the AIN is valid. If not, the computer 102 determines, at a decision state 946, if less than three tries at entering the AIN have been attempted. If so, the computer 102 loops back to state 942 to repeat the request for the AIN. However, if three attempts at entering the AIN have been made, as determined at state 946, the computer 102 plays a polite message that advises the assistant that the login attempt failed and terminates the call at state 948. The computer 102 reports the failed login attempt to the system administrator at the sponsoring agency, hospital or other organization.

If the assistant has correctly entered a valid AIN, as determined at state 944, the computer 102 proceeds to state 950 and prompts the caller to pronounce his or her full name. Moving to a decision state 951, the computer 102 determines whether the voice sample obtained at state 950 passes the matching criteria. If not, the computer proceeds to state 952 and recites a message that the current voice sample does not pass the matching criteria. In the presently preferred embodiment, the current voice sample is compared to the reference voice sample recorded during the assistant registration process 274. Because the voice samples did not match, as determined at state 951, the computer 102 sets the operating mode to Pending at state 953. In this case, Pending mode is set to indicate that one of the security checking methods has failed. However, the process 272 continues at state 960 on FIG. 12b after Pending mode is set at state 953.

If the voice sample passed the matching criteria at state 951, the computer 102 advances to state 954 and recites a message that the current voice sample passed the matching criteria. This security check condition is now satisfied. Next, three additional checks are performed on the assistant identified by the AIN obtained at state 942. At a decision state 955, the computer 102 determines if the permanent assistant flag is true, as stored in the patient and assistant enrollment database 260. If so, the computer 102 advances to a decision state 956 to determine if the expiration date for the permanent assistant is in the future, i.e., the expiration date has not been reached yet. If so, the computer 102 advances to a decision state 957 to determine if a relationship exists between the assistant and a patient, i.e., the assistant has a relationship pointer to the patient record. If so, the operating mode is set to Real at state 958, and then the computer 102 advances through offpage connector A 959 to state 960 on FIG. 12b. However, if any of the decision states 955, 956, or 957 prove to be false, the computer 102 moves to state 953 wherein the operating mode is set to Pending.

States 960 through 964 are similar to states 372 through 374 of the patient login process 250 (FIG. 8). Because of this similarity, only significant differences are discussed in the interest of avoiding repetitiveness. States 960, 962 and 964 verify the assistant's age and sex, rather than the patient as in states 372, 373 and 374. States 966 through 980 are similar to states 386 through 400 of the patient login process 250 (FIG. 8b). The main distinction is that states 966–980 pertain to the assistant and states 386–400 pertain to the patient.

Figure 13A:
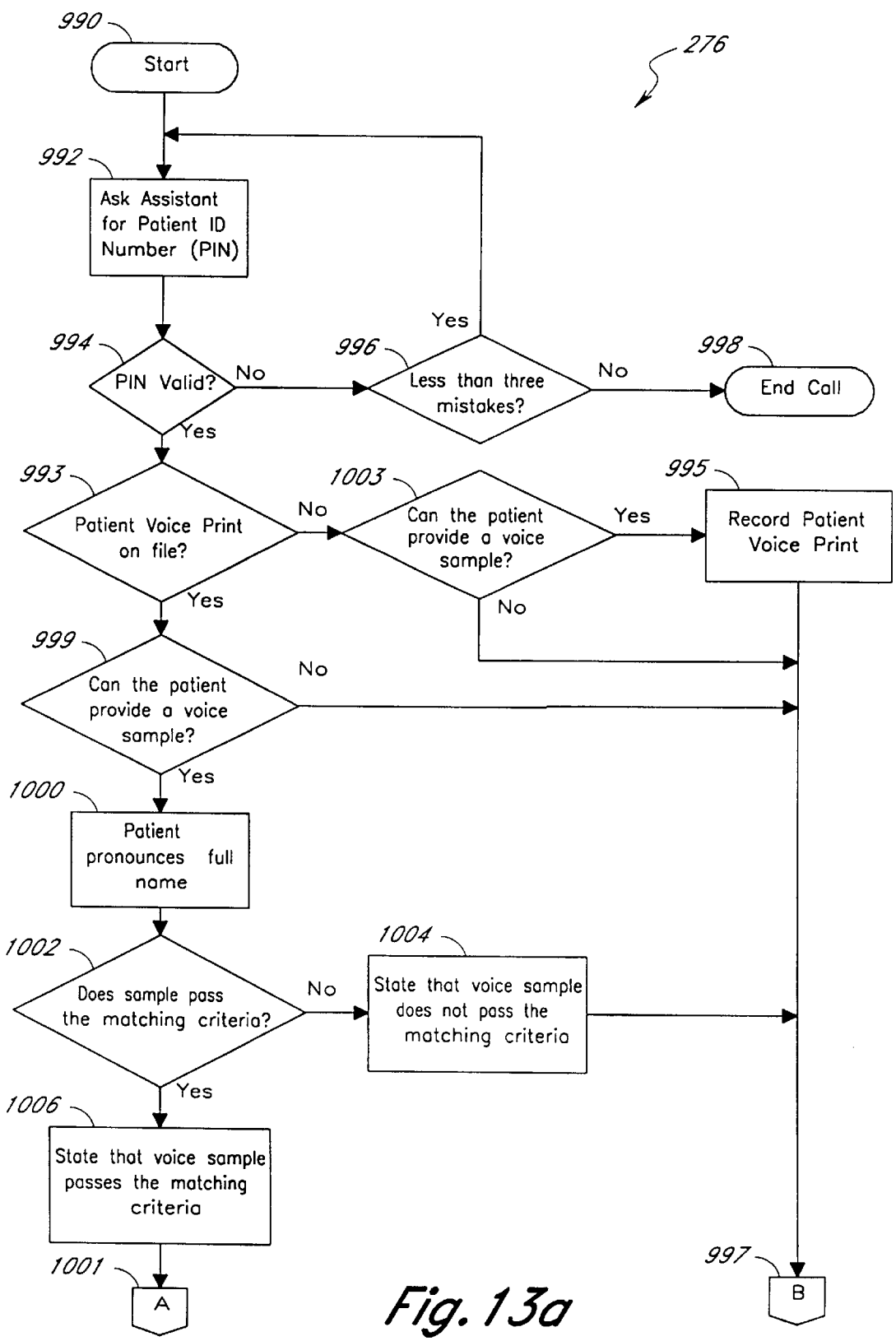
FIGS. 13a and 13b are a flow diagram of the assisted patient login process 276 defined in FIG. 7b.
Figure 13B:
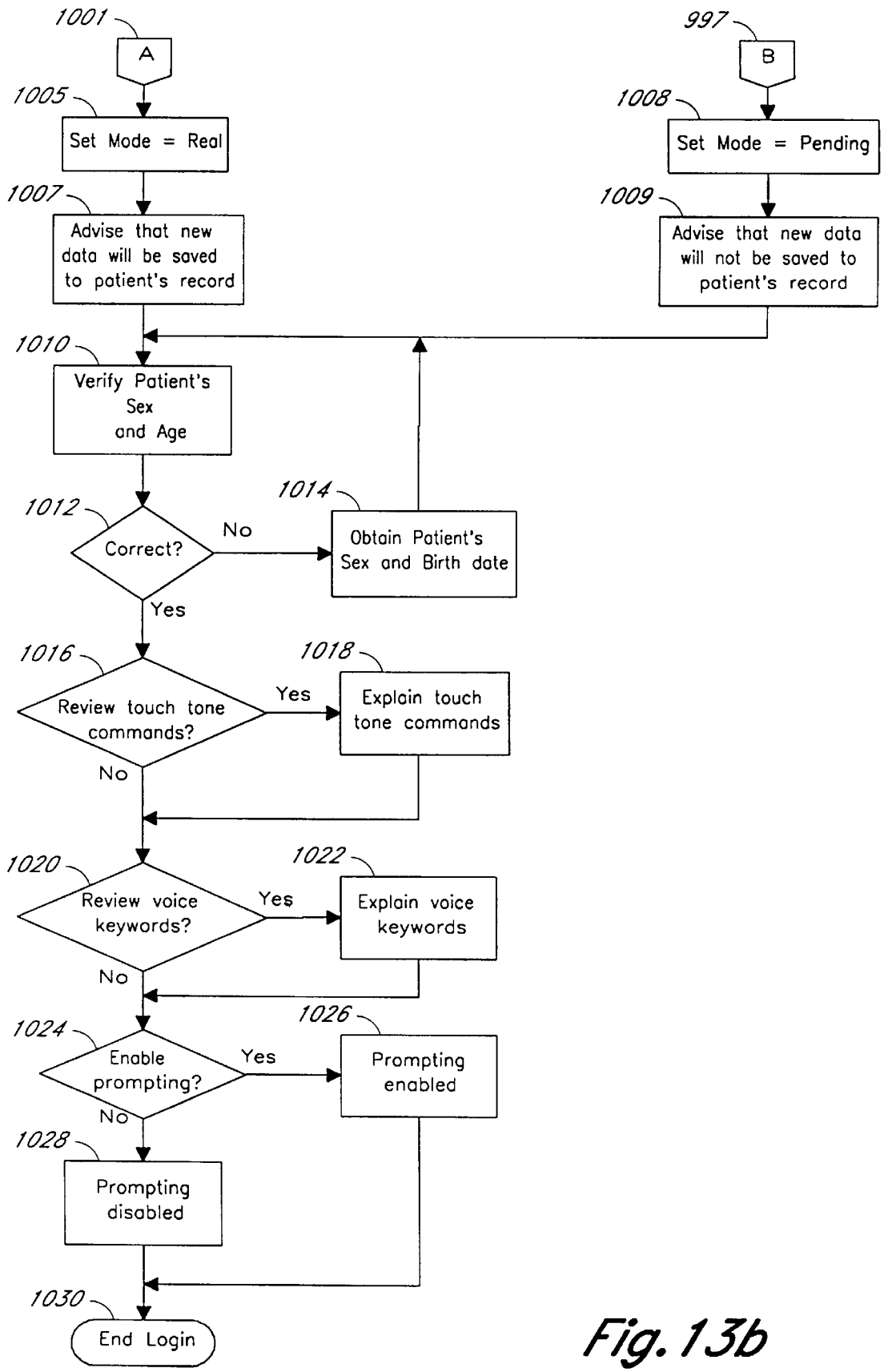

Referring now to FIGS. 13a and 13b, the assisted patient login process 276 defined in FIG. 7b will be described. This process 276 is called if both the patient and the assistant have previously called and registered with the system 100. This process allows the patient flexibility by permitting the assistant to provide help during the login and subsequent consultation. Beginning at a start state 990, the computer 102 moves a state 992 and prompts the assistant for the patient ID (identification) number (PIN) that is assigned during the registration process. As previously defined in FIG. 7, the assisted patient registration process 278 is called if the patient is not already registered. Process 278 will be described in conjunction with FIGS. 15*a* and 15*b*. Proceeding to a decision state 994, the computer 102 determines whether the PIN is valid. If not, the computer 102 determines, at a decision state 996, if less than three tries at entering the PIN have been attempted. If so, the computer 102 loops back to state 992 to repeat the request for the PIN. However, if three attempts at entering the PIN have been made, as determined at state 996, the computer 102 plays a polite message that advises the caller that the login attempt failed and terminates the call at state 998. The computer 102 reports the failed login attempt to the system administrator at the sponsoring agency, hospital or other organization. If the assistant doesn't know the PIN and the patient cannot provide it, the assistant is allowed to reregister the patient as a new patient at process 278 to permit access to the needed medical information. In this case, the assistant may have to estimate the age of the patient if the patient has, for example, an altered state of consciousness. The system administrator resolves the record-keeping in this situation off-line.

If the assistant has correctly provided a valid PIN to the system 100 at state 994, the computer 102 moves to a decision state 993 to determine if the patient identified by the PIN has a voice print or sample voice waveform on file in the system 100. If not, the computer 102 moves to a decision state 1003 to determine if the patient can provide a voice sample. If not, the computer 102 proceeds through off-page connector B 997 to state 1008 on FIG. 13*b*. If the patient can provide a voice sample, as determined at state 1003, the computer 102 moves to state 995 to record the voice print of the patient, e.g. the patient's pronunciation of his or her full name. The patient's voice print may not be on file, for example, if the patient could not provide a voice print during the assisted patient registration process 278 in a prior consultation. At the completion of recording the voice print at state 995, the computer proceeds through off-page connector B 997 to state 1008 on FIG. 13*b*.

If the patient identified by the PIN has a voice print on file in the system 100, as determined at state 993, the computer 102 proceeds to state 999 and asks whether the patient can provide a voice sample to the system. If not, the computer 102 proceeds through off-page connector B 997 to state 1008 on FIG. 13*b*. States 1000, 1002, 1004, 1006 are similar to states 367, 368, 369, 371, respectively, of the patient login process 250 (FIG. 8). Because of this similarity, only significant differences are discussed in the interest of avoiding repetitiveness. At the completion of state 1004, i.e., the patient's voice sample does not pass the matching criteria, the computer 102 proceeds through off-page connector B 997 to state 1008 on FIG. 13*b*. At the completion of state 1006, i.e., the patient's voice sample does pass the matching criteria, the computer 102 proceeds through off-page connector A 1001 to state 1005 on FIG. 13*b*.

At the completion of state 995, i.e., the patient's is voice print is recorded, state 999 or state 1003, i.e., the patient cannot provide a voice sample, or state 1004, i.e., the voice sample match fails, the system continues process 276 at state 1008 on FIG. 13*b*. For the three situations just described in this process 276, the computer 102 sets the operating mode to Pending at state 1008. The system 100 then advises the caller at state 1009 that new patient information will not be saved to the patient's medical record because the consultation is in Pending mode until the information is verified off-line.

At the completion of state 1006, i.e., the voice sample passes, the computer 102 continues process 276 at state 1005 wherein the operating mode is set to Real. The system 100 then advises the caller at state 1007 that new patient information will be saved to the patient's medical record.

At the completion of state 1009 or state 1007, the computer 102 moves to state 1010. States 1010, 1012 and 1014 verify the patient's age and sex, similar to states 372, 373 and 374 (FIG. 8). States 1016 through 1030 are similar to states 386 through 400 of the patient login process 250 (FIG. 8). The main distinction is that states 1016–1030 are directed to the assistant and states 386–400 are directed to the patient.

IX. Registration Process

Figure 9A:
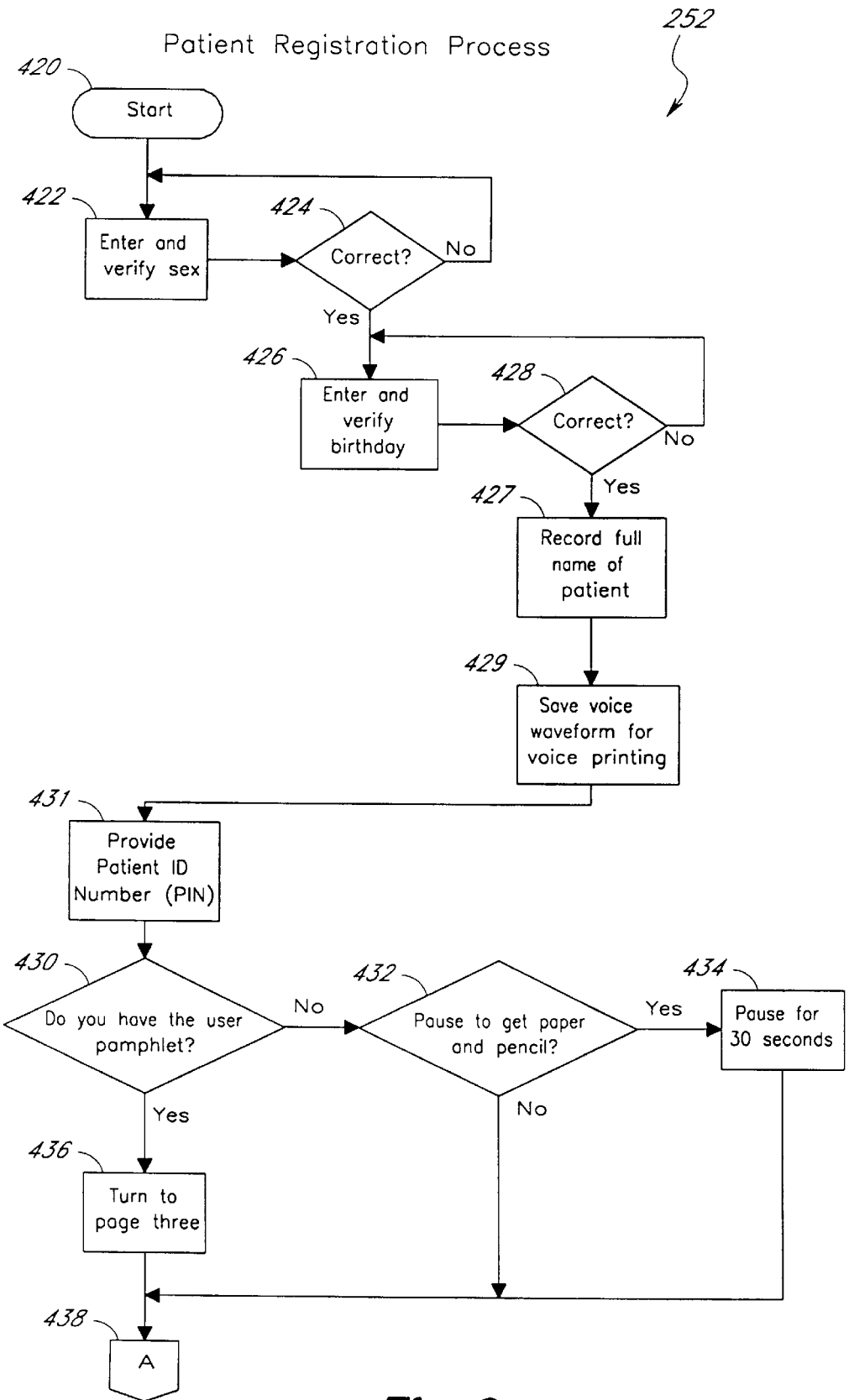
Figure 9B:
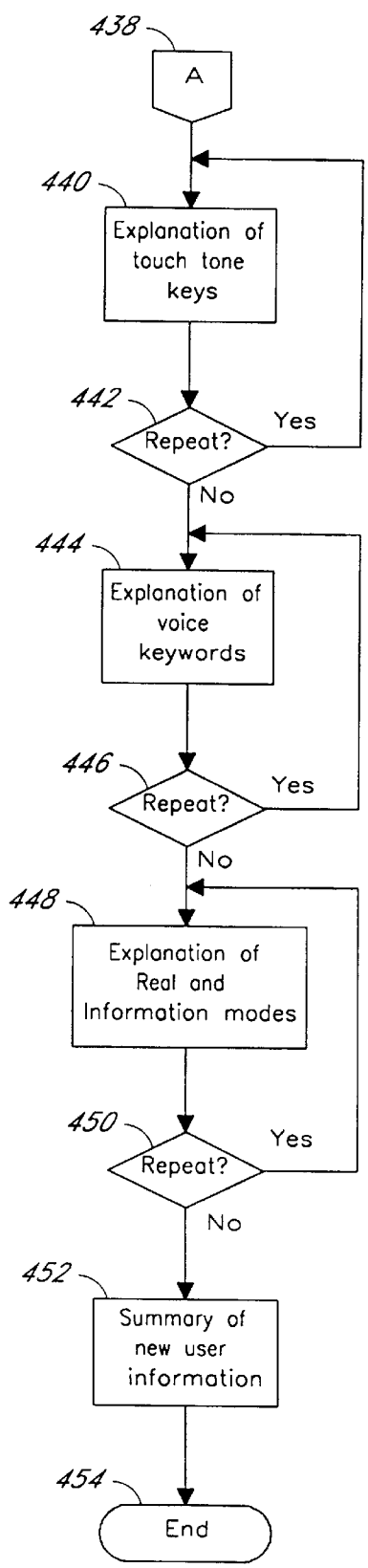

Referring now to FIGS. 9*a* and 9*b*, the patient registration process 252 defined in FIG. 7*a* will be described. This process 252 is called if the patient has not previously called and registered with the system 100. During the first consultation, the MDATA system 100 obtains the patient's age and sex. This is the minimum amount of information that the MDATA system requires in order to give medical advice. The more information the MDATA system has about a patient, however, the more specific is its advice.

The MDATA system 100 assigns each of its patients a unique patient identification number. In addition, when a patient initially registers, the patient's own pronunciation of his or her name is recorded, digitized and saved to their medical record. Then, when the patient calls back, the previous recording is retrieved and the patient is asked to repeat their name exactly as they did during registration. The two recordings are then compared to see if they match. This use of "voice printing" helps to further ensure the security and confidentiality of a patient's medical record.

Beginning at a start state 420, the computer 102 proceeds to state 422, requests the sex of the patient, and verifies by repeating the response given by the patient. Moving to a decision state 424, the patient responds by indicating to the system 100, via touch tone key or a voice response, whether the repeated information is correct. If not, the computer 102 loops back to state 422 to request the information again. When the information is correct at state 424, the computer 102 proceeds to states 426 and 428 to request and verify the birth date of the patient in a similar fashion to states 422 and 424.

When the decision state 428 is determined to be true, the computer 102 proceeds to state 427 and requests the patient to pronounce his or her full name. Moving to state 429, the full name is digitized and stored in a subdirectory on the hard drive 152 (FIG. 1) indexed by a Patient Identification Number (PIN). File names are of the form: <PIN>.vox. The computer 102 accesses a file to retrieve the next available PIN. The path name to the recorded voice file is saved in the patient's record in the enrollment database 260. In subsequent telephone sessions with the system 100, the patient's voice waveform will be compared to the recorded voice waveform for security and other optional purposes. When the voice waveform is stored, the computer 102 moves to state 431 and provides the PIN to the patient. The patient is informed of the importance to save the PIN for use in future consultations with the system 100.

At the completion of state 431, the computer 102 moves to a decision state 430 to determine if the patient has a MDATA system user pamphlet available. If so, the computer 102 moves to state 436 and requests the patient to turn to the pamphlet page that documents the touch tone keys, voice keywords, and modes. If not, the computer 102 moves to a decision state 432 to determine if the patient would like the system 100 to pause to enable the patient to get paper and a writing instrument for writing user instructions. If so, the computer 102 pauses at state 434 for 30 seconds. At the completion of the pause at state 434, if the user did not desire a pause at state 432, or after the patient is instructed to turn to the proper page of the pamphlet, the computer 102 proceeds to state 440 of FIG. 9b via the off-page connector A 438.

At state 440, the system 100 provides an explanation of the touch tone keys to the patient. These keys were described above in relation to the discussion on Voice Keywords and DTMF Command Keys. Moving to state 442, the computer 102 asks if the patient desires to hear the explanation of keys again. If so, the computer 102 repeats state 440. If not, the computer 102 advances to state 444 wherein an explanation of the voice keywords is provided to the patient. These keywords were previously described above. Moving to state 446, the computer 102 asks if the patient desires to hear the explanation of keywords again. If so, the computer 102 repeats state 444. If not, the computer 102 advances to state 448 wherein an explanation of Real and Information modes is provided to the patient. These modes were previously described above. Moving to state 450, the computer 102 asks if the patient desires to hear the explanation of the modes again. If so, the computer 102 repeats state 448. If not, the computer 102 advances to state 452 wherein a summary of new user information is recited to the patient. The summary includes a recap of the two methods of controlling the system: voice key words and DTMF, and the two interaction modes: Real and Info. The computer 102 returns at state 454 to the top level flow (FIG. 7).

Figure 14A:
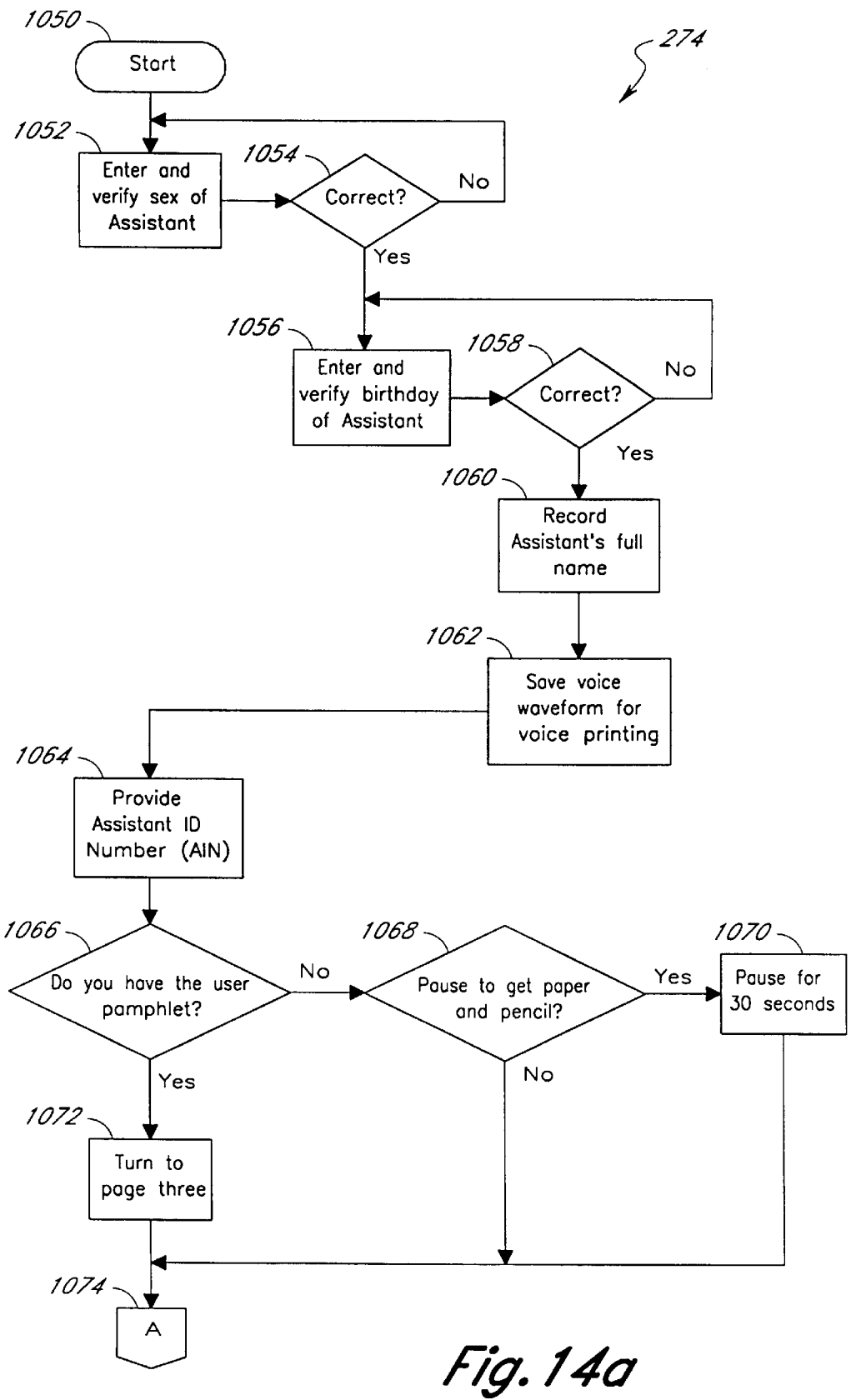
FIGS. 14a and 14b are a flow diagram of the assistant registration process 274 defined in FIG. 7b.
Figure 14B:
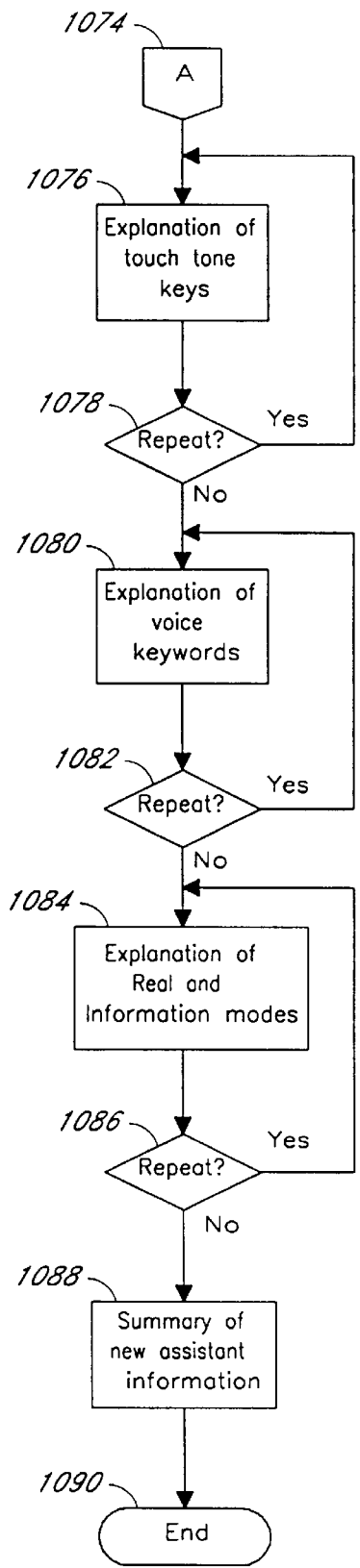

Referring now to FIGS. 14a and 14b, the assistant registration process 274 defined in FIG. 7b will be described. This process 274 is called if the caller is not a registered patient and has not previously called and registered as an assistant with the system 100. States 1050 through 1090 are similar to states 420 through 454 of the patient registration process 252 (FIG. 9). Because of this similarity, only significant differences are discussed in the interest of avoiding repetitiveness. States 1052, 1056, 1060, 1062 and 1064 pertain to the assistant rather than the patient as in states 422, 426, 427, 429 and 431 (FIG. 9a), respectively. State 1060 records the assistant's pronunciation of his or her full name and state 1062 saves it in the patient and assistant enrollment database 260. The system 100 provides an assistant identification number (AIN) at state 1064. The AIN is used similarly to the PIN in the access of files or records. The remaining states 1066–1090 are directed to the assistant also.

Figure 15A:
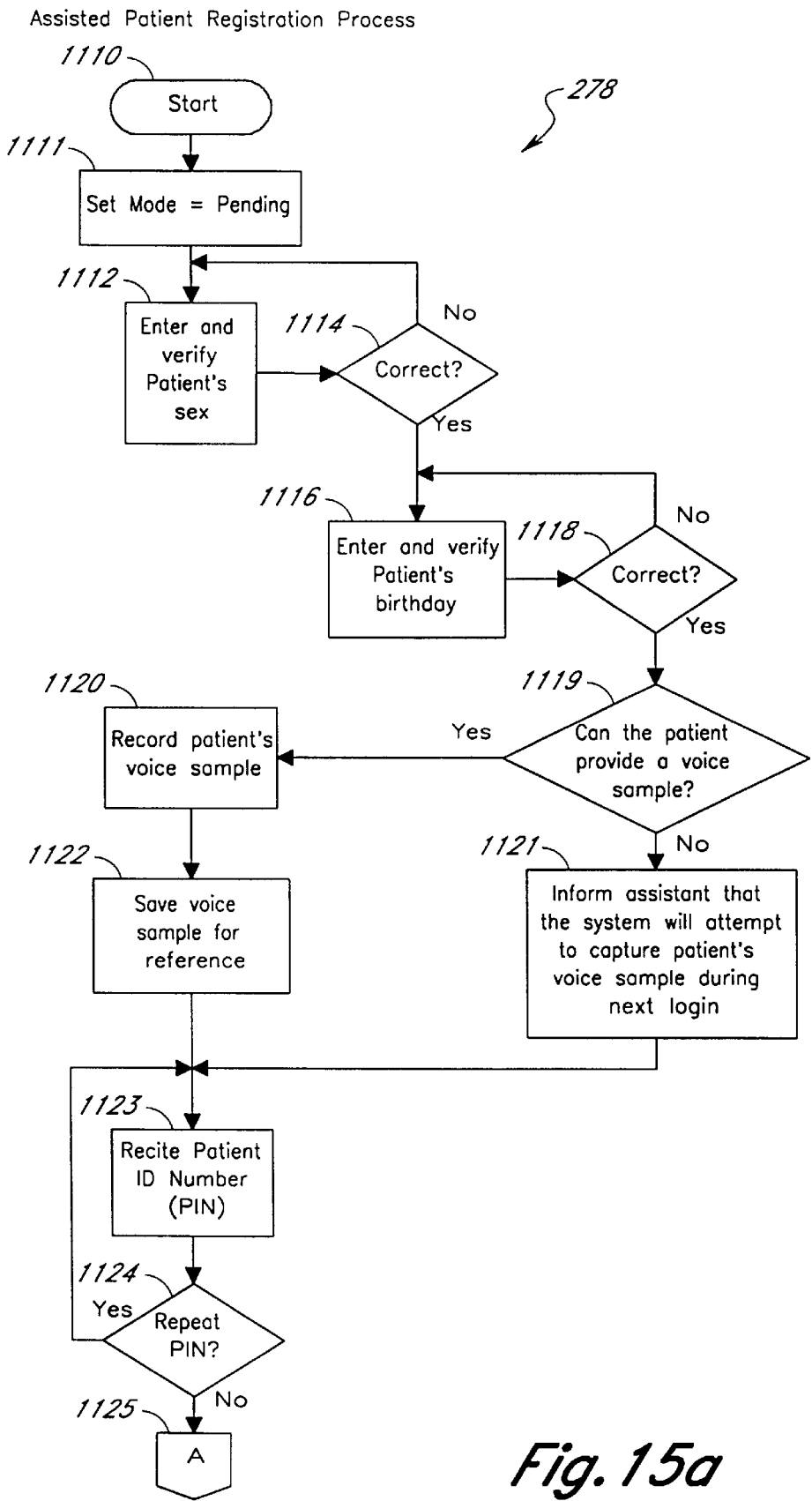
FIGS. 15a and 15b are a flow diagram of the assisted patient registration process 278 defined in FIG. 7b.
Figure 15B:
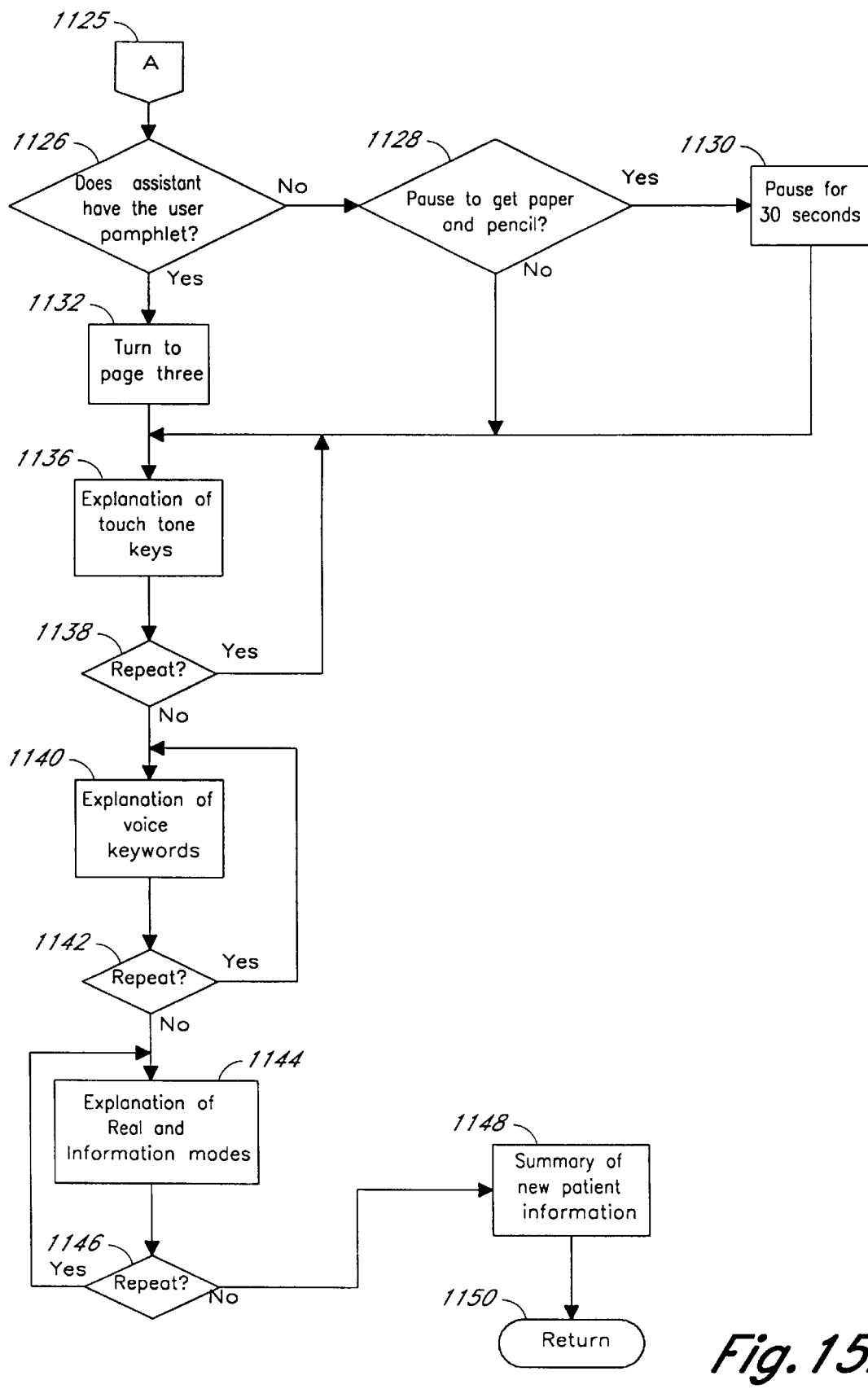

Referring now to FIGS. 15a and 15b, the assisted patient registration process 278 defined in FIG. 7b will be described. This process 278 is evoked if the caller is not the patient and the patient has not previously called and registered with the system 100. States 1110 through 1150 are similar to states 420 through 454 of the patient registration process 252 (FIG. 9). Because of this similarity, only significant differences are discussed in the interest of avoiding repetitiveness. The main difference is that the assistant is interacting with the system 100 on behalf of the patient during this process 278, and therefore, the operating mode is set to Pending at state 1111. States 1112 and 1116 obtain the patient's sex and age, respectively. If the patient cannot provide the age to the assistant and the system, the assistant provides an estimated age. The estimated age can be corrected during a subsequent consultation with the system 100. At state 1119, the system 100 asks whether the patient can provide a voice sample of his or her full name. If so, the voice waveform is recorded and saved in enrollment database 260 (FIG. 6) at states 1120 and 1122. If the patient cannot provide a voice sample at state 1119, the system 100 informs the assistant, at state 1121, that the patient's voice sample will be requested during the subsequent consultation. Then, whether or not a voice sample is recorded, the system 100 provides a patient identification number (PIN) of the patient to the assistant and the patient (if coherent) at state 1123. The caller is instructed to safeguard the PIN for future consultations by either the patient or the assistant on behalf of the patient. If the assistant and/or patient desires to hear the PIN again, as determined at a decision state 1124, the computer 102 repeats the PIN at state 1123. The computer 102 proceeds through off-page connector A 1125 to a decision state 1126 on FIG. 15b. The remaining states 1126–1150 in process 278 are directed to the assistant rather than the patient, as in states 430–454 of process 252 (FIG. 9).

X. Evaluation Process

Figure 10A:
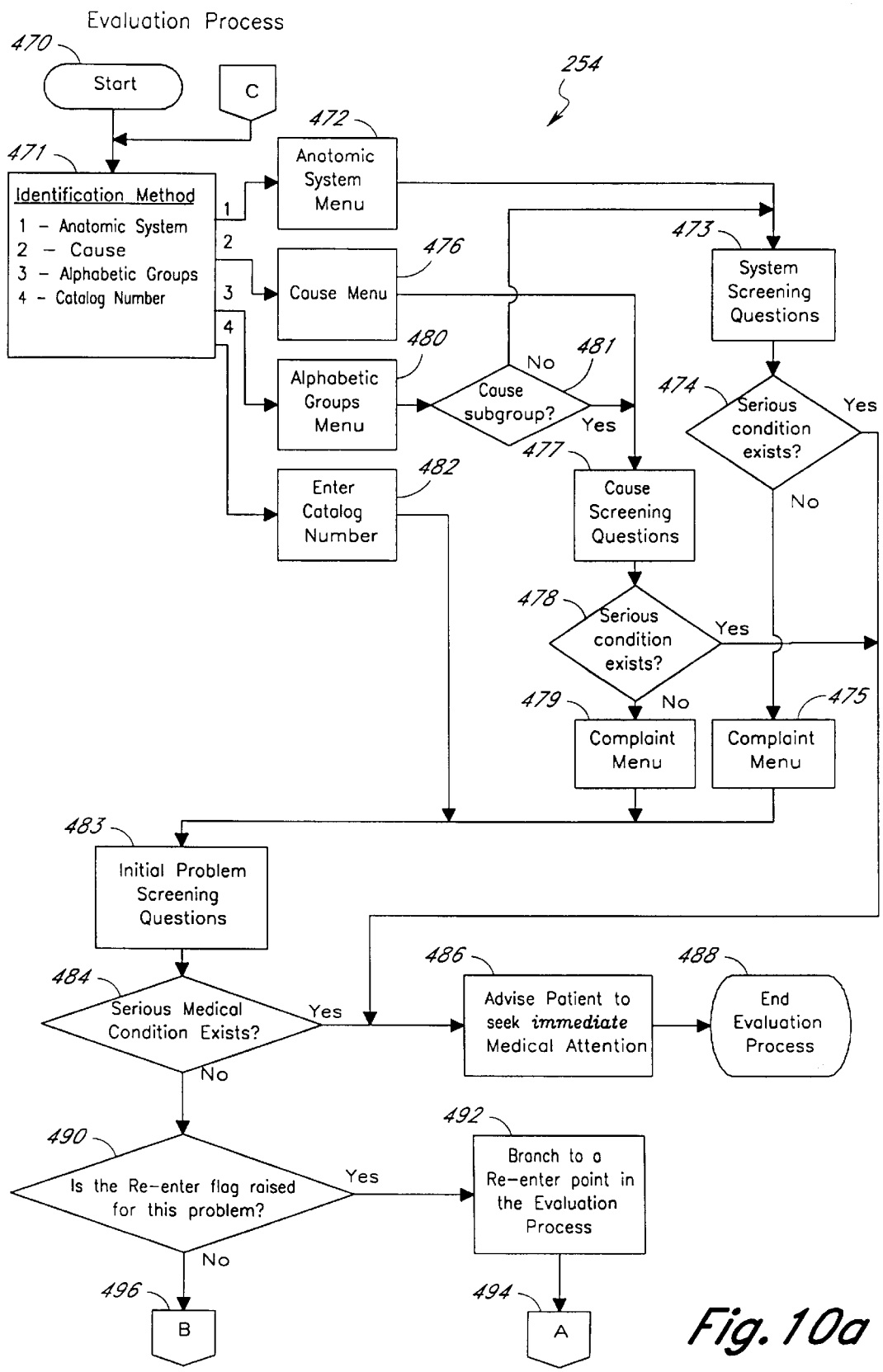
FIGS. 10a and 10b are a flow diagram of the evaluation process 254 defined in FIG. 7d.
Figure 10B:
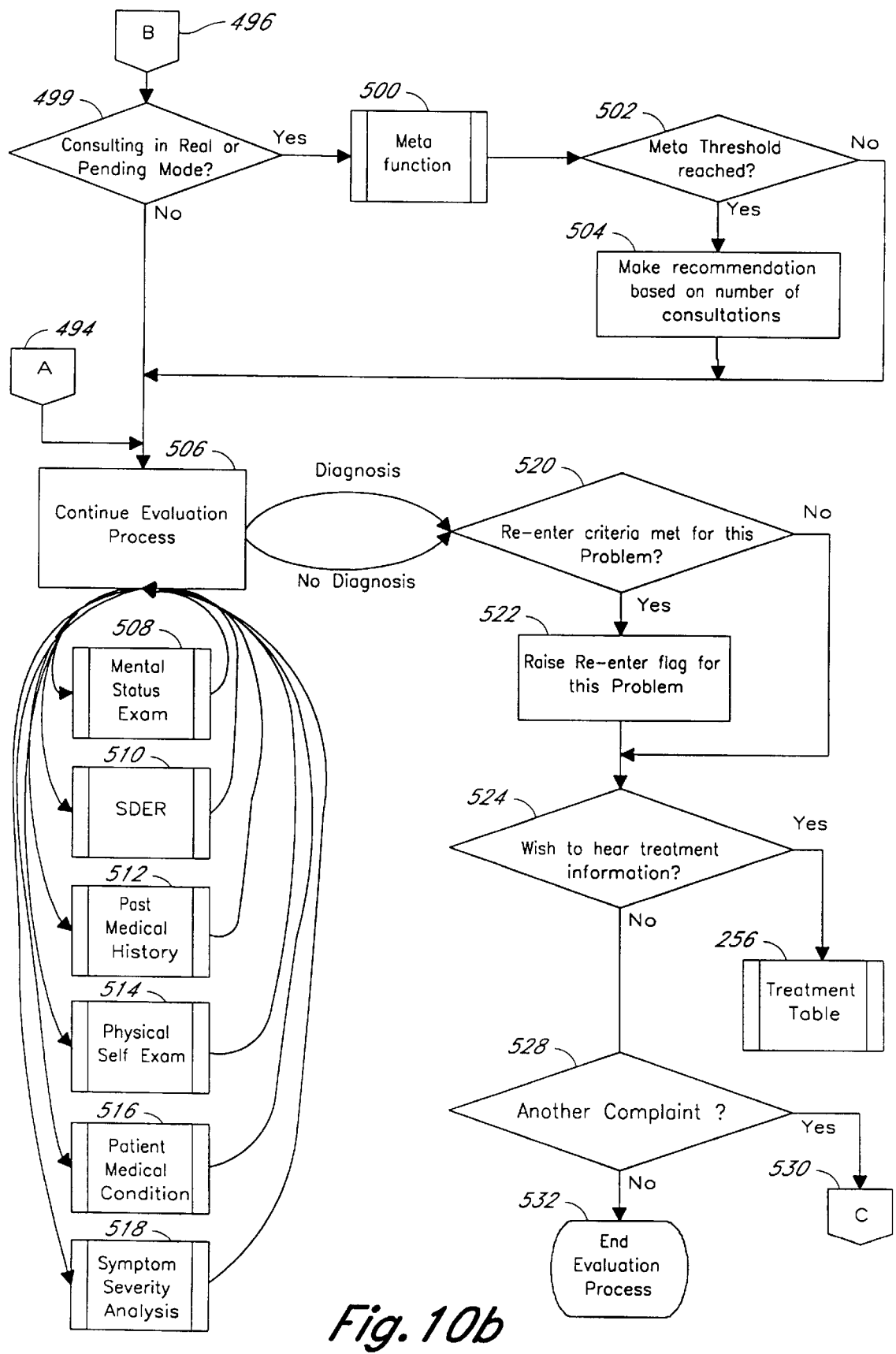

Referring now to FIGS. 10a and 10b, the evaluation process 254 defined in FIG. 7d will be described. This process 254 is called if the patient has selected the Diagnostic System choice in the system selection menu (FIG. 7d, state 344). Beginning at a start state 470, the computer moves to state 471 and recites a identification method menu to request complaint identification. After the initial screening questions (state 306, FIG. 7a) are completed and a medical record (registration function 252) has been opened, the MDATA system 100 asks the patient to describe the complaint. The identification of the patient's problem is one of the most important steps in the evaluation process. The system 100 has built-in safeguards to ensure that the patient understands the questions and that the MDATA system 100 understands the patient's complaint. For example, the system keeps tables of synonyms so that any problem regarding the semantics of a question or a response can be quickly resolved. The complaint may be identified in one of four ways: by anatomic system 472, by cause 476, by alphabetic groups 480 or by catalog number 482.

The easiest and most frequently used way to identify the complaint is by anatomic system, i.e., "what system is your problem in?". Anatomic system 472 refers to basic body systems such as cardiovascular, respiratory, nervous system, digestive, ear/nose/throat, ophthalmology, gynecology/ obstetrics, urology, blood/hematology, skin, and endocrine. After the patient has identified the anatomic system of their complaint, they are asked a series of "System Screening Questions" at state 473. For each anatomic system, there are some symptoms or combinations of symptoms that, if present, would mandate immediate intervention, such that any delay, even to go any further through the menuing process, could cause harm. For example, if the patient has identified the cardiovascular system as the anatomic system in which his or her complaint lies (i.e., chest pain), the MDATA system 100 will ask the cardiovascular system screening questions. For example, the patient would be asked, "Do you have both pressure in your chest and shortness of breath? If these symptoms are present together, immediate intervention is necessary. With the thrombolytic agents that are available today, time is critical in order to save myocardial cells. Just a few minutes can mean the difference between being able to resuscitate a patient or not.

Therefore, at state 474, the system 100 determines if a serious medical condition exists. If so, the system 100 moves to state 486, plays a message that advises the patient to seek immediate medical attention and ends the evaluation process 254 at a terminal state 488. If it is determined at state 474 that a serious medical condition does not exist, the system 100 proceeds to a complaint menu at state 475 and recites a list of algorithms dealing with the problem that corresponds to the anatomic system selected. The patient then selects an algorithm from the list.

If the patient is not sure of the anatomic system, the system 100 attempts to identify the problem by requesting the cause. Cause 476 refers to a cause for an illness or disease such as trauma, infection, allergy/immune, poisoning, environmental, vascular, mental, genetic, endocrine/metabolic, and tumor. Once the patient has identified what they think is the cause of their problem (e.g., trauma, infection), the MDATA system 100 asks the "Cause Screening Questions" at state 477. These questions are asked to make sure that the patient is not suffering from an immediate life-threatening problem. For example, if infection were chosen as the cause, the system would first rule out the possibility of epiglottitis or meningitis before proceeding. Therefore, at state 478, the system 100 determines if a serious medical condition exists. If so, the system 100 moves to state 486, plays a message that advises the patient to seek immediate medical attention and ends the evaluation process 254 at a terminal state 488. If it is determined at state 478 that a serious medical condition does not exist, the system 100 proceeds to a complaint menu at state 479 and recites a list of algorithms dealing with the problem that corresponds to the cause selected. The patient then selects an algorithm from the list.

Alphabetic groups 480 lists the items in the anatomic system group and the cause group together in alphabetic order. Moving to state 481, the system determines if the selected item is from the cause subgroup of the combined alphabetic groups. If so, the system 100 proceeds to the "Cause Screening Questions" at state 477. If not, the system moves to the "System Screening Questions" at state 473.

Enter Catalog number state 482 refers to the ability of the patient to select and enter an individual medical algorithm from a catalog of medical algorithms listed in the patient guide distributed to all patients. At the completion of state 475, 479, or 482, the complaint has been identified, and the computer 102 proceeds to state 483 wherein a series of "initial" problem screening questions are presented to the patient. There is a different set of problem screening questions for every complaint for which advice is offered.

For the purpose of this discussion, "Headache" will be used as an example to describe how the system approaches the diagnosis of a problem and provides treatment recommendations. As with many problems, there are some causes of headache that require immediate medical attention. Quite often, when a problem is very serious, any delay, even to discuss it further, can adversely affect the patient's outcome. The problem screening questions identify, at a decision state 484, the subset of patients whose headaches may require immediate medical care. If a serious medical condition exists, the patient is advised to seek immediate medical attention at state 486. The computer 102 then ends the evaluation process at state 488 and returns to state 344 in FIG. 7d.

The following is an example of a problem screening question for headache:

ARE YOU CONFUSED, LETHARGIC, OR LESS ORIENTED THAN USUAL?

By asking a question about the patient's level of consciousness, a dilemma has been confronted. What does the MDATA system 100 do about the patient whose problem itself prevents them from appropriately responding to questions or following advice?

There are some conditions that, by their very nature, may prevent patients from answering questions correctly. For this reason, the MDATA system 100 utilizes a "mental status examination" function 508. The mental status examination is a series of questions used to assess the patient's orientation. This function 508 allows the MDATA system 100 to assess the patent's ability to respond to questions and to follow advice. Although only shown in FIG. 10b, the mental status examination function 508 is incorporated into the dialogue of any problem whose presentation could include an altered level of consciousness. Function 508 will be further described in conjunction with FIG. 16.

The MDATA system 100 will, of course, be accessed by patients in whom an altered level of consciousness is not expected based on the problem that the patient has. The system 100 does anticipate the possibility of the patient having an altered level of consciousness in some problems, e.g., when a patient consults the system for striking his or her head, and invokes the mental status exam function 508. However, an intoxicated patient, calling for some other complaint, e.g., a sprained ankle, is one example where the patient may not be able to understand instructions from the system 100. For this reason, the MDATA system also utilizes a "semantic discrepancy evaluator routine" (SDER) function 510. The SDER function provides information to the patient and then, after a predetermined period of time, asks the patient to repeat or select the information. The patient's answer is then evaluated within system 100. If discrepancies are determined, the system automatically invokes the mental status examination function 508. In another embodiment, the system 100 asks the patient for some information in different ways at different times, and then compares the patient's responses to determine if they are consistent. If not, the system automatically invokes the mental status examination function 508. Although only shown in FIG. 10b, the SDER function 510 is embedded throughout system 100, and is randomly evoked by the computer 102. Function 510 will be further described in conjunction with FIG. 17.

Continuing with the headache example at state 483, the MDATA system 100 asks the next problem screening question in order to help exclude the possibility of meningitis, a very serious infection of the central nervous system.

IS BENDING YOUR NECK FORWARD SO THAT YOUR CHIN TOUCHES YOUR CHEST EITHER PAINFUL OR NOT POSSIBLE?

If the answer to this question is "yes", a serious medical condition exists at state 484 and the system 100 instructs the patient to seek immediate medical attention at state 486.

The initial screening questions (state 306, FIG. 7a) and the problem screening questions (state 483) can usually be completed within a minute or so. Once the MDATA system 100 has excluded the causes of headache that require immediate medical attention, the system becomes a little less formal and more conversational in the subsequent states. The examples given, of course, do not represent all the initial or problem screening questions.

If no serious medical condition exists, as determined at state 484, the computer 102 proceeds to a decision state 490 wherein the system 100 identifies those patients who are "reentering" the system from an earlier consultation. This occurs most frequently when the system 100 needs to monitor a patient's symptom over time, or if the system is initially unable to make a specific diagnosis and would like the patient to re-enter the system again, typically within a few hours. The system sets an internal re-enter flag to identify the situation where a patient is calling again for the same complaint. If the flag is set at state 490, the computer 102 proceeds to state 492 and branches to a re-enter point in the evaluation process depending on which medical algorithm has been evoked. The computer 102 moves via off-page connector A 494 to state 506 (FIG. 10b) to the appropriate re-enter point.

If the re-enter flag is not set, as determined at state 490, the computer 102 moves via off-page connector B 496 to a decision state 499 to determine if the consultation is being performed in Real mode or Pending mode. If not (i.e., the consultation is in Information mode), the computer proceeds to state 506 to continue the evaluation process. If the consultation is in Real or Pending mode, the computer 102 calls a "meta" function 500 wherein patients are subjected to several "meta" analyses. This concept will be explained in conjunction with FIG. 11, but, in general, it refers to the system's ability to evaluate the patient's present problem in the context of their past use of the system. The Meta function 500 matches various parameters against a predetermined meta threshold. When the MDATA system 100 opens a patient's consultation history file in database 262 (FIG. 6), it calculates how many times the patient has consulted the system for the same complaint. For each problem, the MDATA system 100 allows a specified number of system consultations, per unit of time, before it takes action. If the meta threshold is reached, as determined at a decision state 502, the MDATA system 100 makes a recommendation based on this fact alone at state 504. For example, let us assume that the threshold was set at five headaches in two months. If the patient consulted the MDATA system 100 for headache more than four times in two months, the threshold would be reached and the system would make an appropriate recommendation. The threshold, of course, is different for each complaint, and may be modified by a set of sensitivity factors that will be described hereinbelow. Alternately, the system 100 uses a time density ratio (TDR) calculated by the meta function 500 to determine if a recommendation should be given to the patient. At the completion of state 504, or if the meta threshold was not reached at state 502, the computer 102 proceeds to state 506 to continue the evaluation process. State 506 includes a medical algorithm as selected by the patient in states 475, 479, or 482. As a representative example, the Microfiche Appendix contains an algorithm for Headache and includes a Headache node map with the script or description of each node having a play list. A second example node map and associated script for Convulsion or Seizure, including meta and past medical history aspects, is also included in the Microfiche Appendix. Although not necessarily a complete list, other types of medical algorithms include: Chest Pain, Heatstroke, Altered Level of Consciousness, Tremor, Dizziness, Irregular Heartbeat, Fainting, Shortness of Breath, Chest Injury, Depression, Head Injury, Cough, Croup, High Blood Pressure, Hyperventilation, Numbness, Wheezing, Inhalation Injury, and Strokes. In addition to meta and past medical history functionality, at least some of the listed medical algorithms rely upon knowledge of age and/or sex of the patient as provided in the presently described system 100 at time of registration (see FIGS. 9a and 13a).

Depending on the medical algorithm and the exact patient condition, one or more auxiliary functions may be called by state 506 as follows: the mental status examination function 508, the SDER function 510, a past medical history function 512, a physical self examination function 514, a patient medical condition function 516, and a symptom severity analysis function 518. These functions will be described hereinbelow.

Returning to the headache example, after the meta analyses (function 500) are completed, the MDATA system 100 assesses the severity of the patient's headache on a one-to-ten scale. The importance of this purely subjective quantization of the symptom's severity will become apparent later in this description.

Although the MDATA system's paradigm is fundamentally an algorithmic one, the underlying logic of the diagnostic process for headache will be described. The MDATA system 100 begins the diagnostic process for headache by referring to three lists stored internally in the computer 102.

The first list is a ranking of the most common causes of headache in the general population. The most common cause is ranked first, the second most common is ranked second, and so on. In other words, the first list ranks all the causes of headache in the general population in decreasing frequency of occurrence.

The second list is a ranking of the various causes of headache according to the seriousness of the underlying cause. The more serious causes are positioned toward the top of the list, the less serious toward the bottom. For example, meningitis, brain tumor, and subarachnoid hemorrhage would be the top three causes on the second list.

The third list is quite similar to the second list. It ranks the causes of headache according to the rapidity with which intervention is necessary. The causes of headache that require immediate intervention, such as meningitis and subarachnoid hemorrhage, are toward the top. The problem screening questions (state 483) were developed from this list.

During the evaluation process 254, the MDATA system 100 asks the patient a series of "diagnostic screening questions." From the answers to these questions, along with any physical signs elicited from the patient (from function 514), under the direction of the MDATA system 100, the system establishes the most likely cause of the patient's headache.

The following are examples of diagnostic screening questions for headache:

DO YOU EXPERIENCE MORE THAN ONE KIND OF HEADACHE?

DO YOU, OR DOES ANYONE ELSE, KNOW THAT YOU ARE GOING TO GET A HEADACHE BEFORE THE ACTUAL PAIN BEGINS?

DO YOUR HEADACHES FREQUENTLY WAKE YOU UP AT NIGHT?

DO YOUR HEADACHES USUALLY BEGIN SUDDENLY?

Based upon the answers to the diagnostic screening questions, the MDATA system 100 reorders the first list. The first list then becomes a list of the possible causes of headache in decreasing levels of probability in the patient seeking consultation. The first list is now patient specific. If the MDATA system 100 concludes that migraine is the most likely cause of the patient's headache, then migraine will now be ranked at the top of the first list.

The MDATA system 100 is knowledgeable about the difference between classic, common, and all other variants of migraine, but for this discussion the general term "migraine" will be used. After reordering the first list and placing migraine at the top, the MDATA system 100 then asks several questions related specifically to migraine headaches. These are called the "migraine screening questions." The probability that the patient actually has a migraine headache is calculated from the answers to these questions. Each cause of headache has its own set of screening questions, physical examination signs, and, if the patient has the MDATA system's Home Diagnostic and Treatment Kit, appropriate laboratory tests.

The following are examples of migraine screening questions:

IS EITHER NAUSEA OR VOMITING ASSOCIATED WITH YOUR HEADACHE?

ARE VISUAL DISTURBANCES ASSOCIATED WITH YOUR HEADACHE?

After obtaining the answers to the migraine screening questions, if the probability that the patient is suffering from a migraine headache does not reach an established threshold, the next cause of headache on the reordered first list is considered and pursued as a diagnosis.

If the probability of having a migraine headache does reach the threshold, the MDATA system 100 asks the patient several more questions designed to confirm the presence of migraine, given the fact that the system has already determined that it is the most likely diagnosis. These are called the "migraine confirmation questions." Just as each cause of headache has a set of screening questions, each cause of headache also has a set of confirmation questions.

The following are examples of migraine confirmation questions:

DOES ANYONE WHO IS RELATED TO YOU BY BLOOD HAVE MIGRAINE HEADACHES?

WHEN YOU HAVE A HEADACHE DO YOU FEEL MORE LIKE LYING DOWN OR WALKING AROUND?

From the answers to the migraine confirmation questions, the MDATA system 100 calculates the probability of confirmation of migraine. In Bayes' terms (which refer to the probability of certainty of a diagnosis) this is called a "conditional probability."

If the probability of migraine headaches reaches threshold, but the probability of confirmation of migraine does not reach threshold, then, as mentioned, the system pursues the next diagnostic cause of headache on the patient specific list.

If the probability of the second cause of headache (say cluster) reaches threshold, then the "cluster confirmation questions" are asked. If they reach threshold, then again the serious causes of headache are excluded as a diagnosis. The MDATA system 100 stores the scores of all the screening and confirmation questions in what are called "session memory variables" that are installed in the symbol table. It is, in part, these scores that are then used to determine the probability of one diagnosis versus another.

For example, if the answers to the cluster confirmation questions do not reach threshold, then the scores of the screening and confirmation questions of migraine and cluster are compared to see which cause is the more probable. Whichever has the higher score, or exceeds the other by a predetermined threshold, is then assumed to be the more probable cause. The list is, if necessary, again reordered. This time it becomes the final diagnostic list which is a list of differential diagnoses in decreasing levels of probability for this patient.

All of the headache scoring thresholds are modified or modulated by a series of sensitivity factors as are all aspects of the system in which scalar thresholds are used. The sensitivity factors are discussed hereinbelow in section XVIII. For example, if it was found that a subset of patients in which the diagnosis of meningitis was not being made as early as it should be, then the sensitivity factor modifying the temperature threshold could be decreased so that now, a patient with a lower temperature would be instructed to seek an immediate evaluation.

Before discussing the results with the patient, however, the MDATA system 100 must again rule out the serious causes of headache. The problem screening questions have already filtered out those patients who have a serious cause of. headache, such as meningitis, that requires immediate medical intervention.

The MDATA system 100 now proceeds to eliminate those causes of headache that, although serious, do not require immediate medical attention. For example, although a brain tumor is a serious cause of headache, it is not as immediately life threatening as meningitis or subarachnoid hemorrhage. To accomplish this task, the MDATA system 100 sequentially analyzes the serious causes of headache that are located at the top of the second list. The MDATA system 100 again asks the patient the set of screening questions associated with each of the serious causes of headache. This time, however, the MDATA system 100 makes sure that the probability of having any of the serious causes of headache is sufficiently low in order to exclude them from diagnostic consideration. Only after this is accomplished will the system discuss its conclusion and recommendations with the patient.

The discussion that the MDATA system would have with the migraine headache patient would include the following:

Its diagnostic impression, or its diagnostic impressions in decreasing levels of probability.

Its estimate of the level of probability of migraine.

Whether or not the system feels it has excluded the serious causes of headache to a level of certainty that satisfies the system.

What tests, if any, should be obtained to confirm or exclude a diagnosis.

How soon to see a physician.

What kind of physician to see (e.g., family practitioner, internist, or neurologist).

What kind of information to bring to the physician when a consultation is obtained.

Questions to ask the physician.

The latest treatment for migraine.

Even if the MDATA system 100 cannot determine with sufficient certainty what is causing the headache, it can still provide patients with valuable information and advice. For example, the patient may be told the following:

"At this time, the MDATA system is unable to pinpoint a particular cause of your headache with the degree of certainty required to make specific recommendations. The MDATA system, however, suggests a consultation with a neurologist. You can either call your family practitioner or internist and ask for a referral.

"While you are waiting to be seen by the neurologist, there are many things that you can do in order to help the physician diagnose your headache. Many headache experts have found that a record of when their patients' headaches occur and how bad they are is very helpful in finding both the cause of the headache as well as the best treatment.

"In order to assist you, the MDATA system will send you a blank calendar on which you can record the time and severity of your headaches. In addition, there is space for you to record what seems to bring on the headaches, makes them worse, or makes them better. The MDATA system will also send you a questionnaire to fill out and give to your doctor, containing a list of questions asked by some of the world's leading headache experts when they are trying to arrive at a diagnosis."

A full set of instructions will be provided.

The MDATA system is able to customize the information given to patients to accommodate the individual needs of a sponsoring agency or group such as a Health Maintenance organization (HMO) or a Managed Care Plan. For example, if the system finds that the patient should see a physician, the MDATA system can determine from a patient's medical record whether they have an established relationship with an appropriate specialist. If they do, the specialist's name and phone number, or a list of participating specialists for their HMO or Managed Care Plan and any specific instructions, will be given to the patient with the recommendation to make an appointment within a specific time frame.

At the conclusion of state 506, the system may or may not have a reasonably certain diagnosis available. For example, the headache algorithm provides a diagnosis of migraine in response to a particular set of patient symptoms. In situations where the MDATA system 100 cannot determine with sufficient certainty what is causing a particular problem (no diagnosis) or in a situation where a diagnosis is available but additional information is desirable, e.g., to determine a trend, a re-enter flag may be set by the system 100. At a decision state 520, the computer 102 determines if re-enter criteria are met for the current algorithm and patient situation. If so, the computer sets the re-enter flag at state 522 for this problem so a subsequent telephone consultation by the patient will allow for additional information to be added to the patient record by the system in full knowledge of the previous call. This additional information may yield a better diagnosis.

If the re-enter criteria were not met, as determined at state 520, the computer 102 proceeds to a decision state 524 to determine if the patient desires to hear treatment information for the current problem. If so, the computer 102 calls the treatment table process 256, which will be described in conjunction with FIGS. 22 and 23. If the patient does not wish to hear treatment information at this time, the computer 102 advances to a decision state 528 to determine if the patient would like to investigate another complaint through the evaluation process 254. If so, the computer 102 moves via off-page connector C 530 to state 471 on FIG. 10a to repeat the process 254. However, if the patient does not wish to pursue another complaint, the computer returns at state 532 to the top level flow (FIG. 7d).

XI. The Meta Function

Figure 11A:
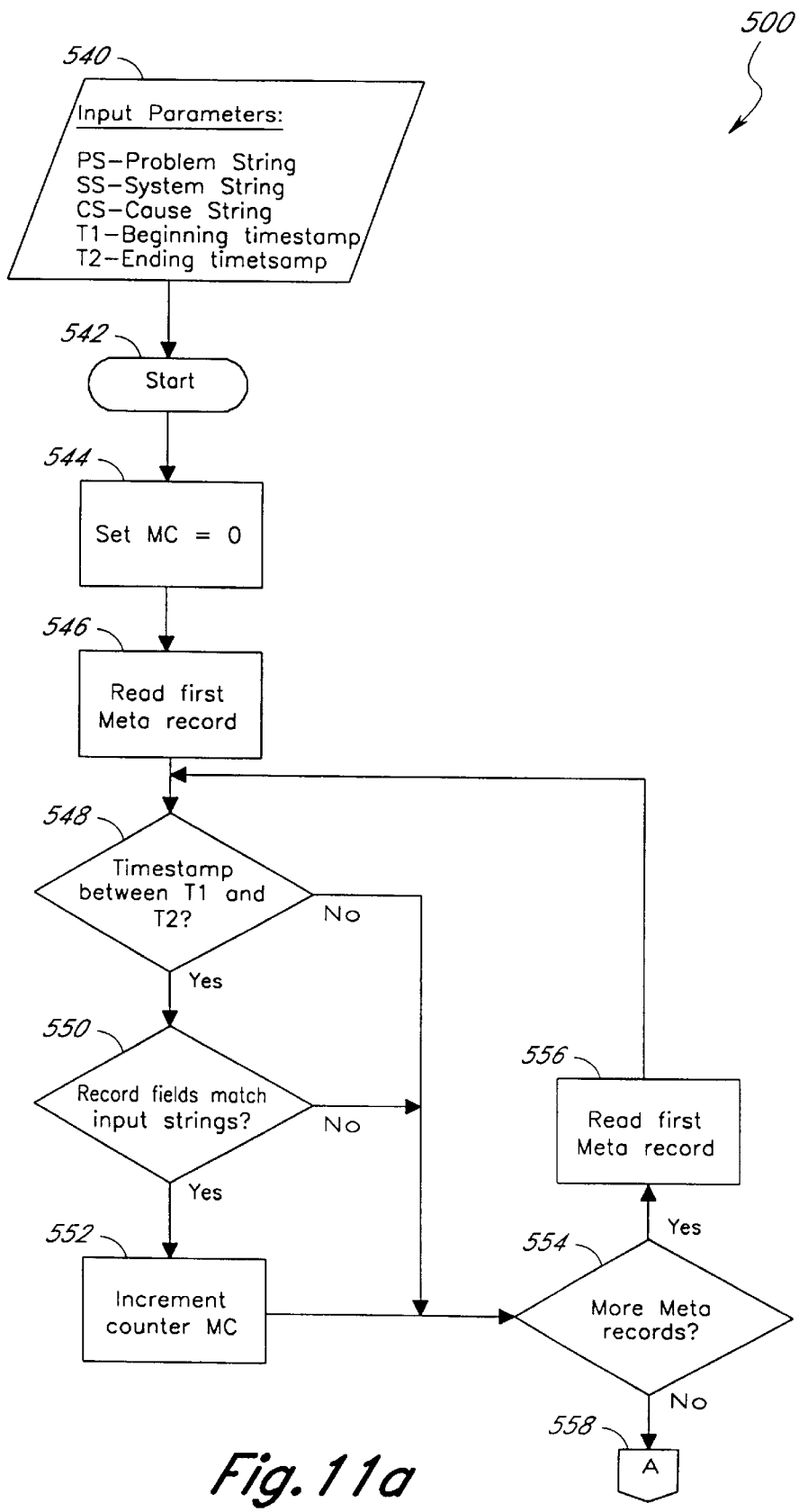
FIGS. 11a and 11b are a flow diagram of the meta function 500 defined in FIG. 10b.
Figure 11B:
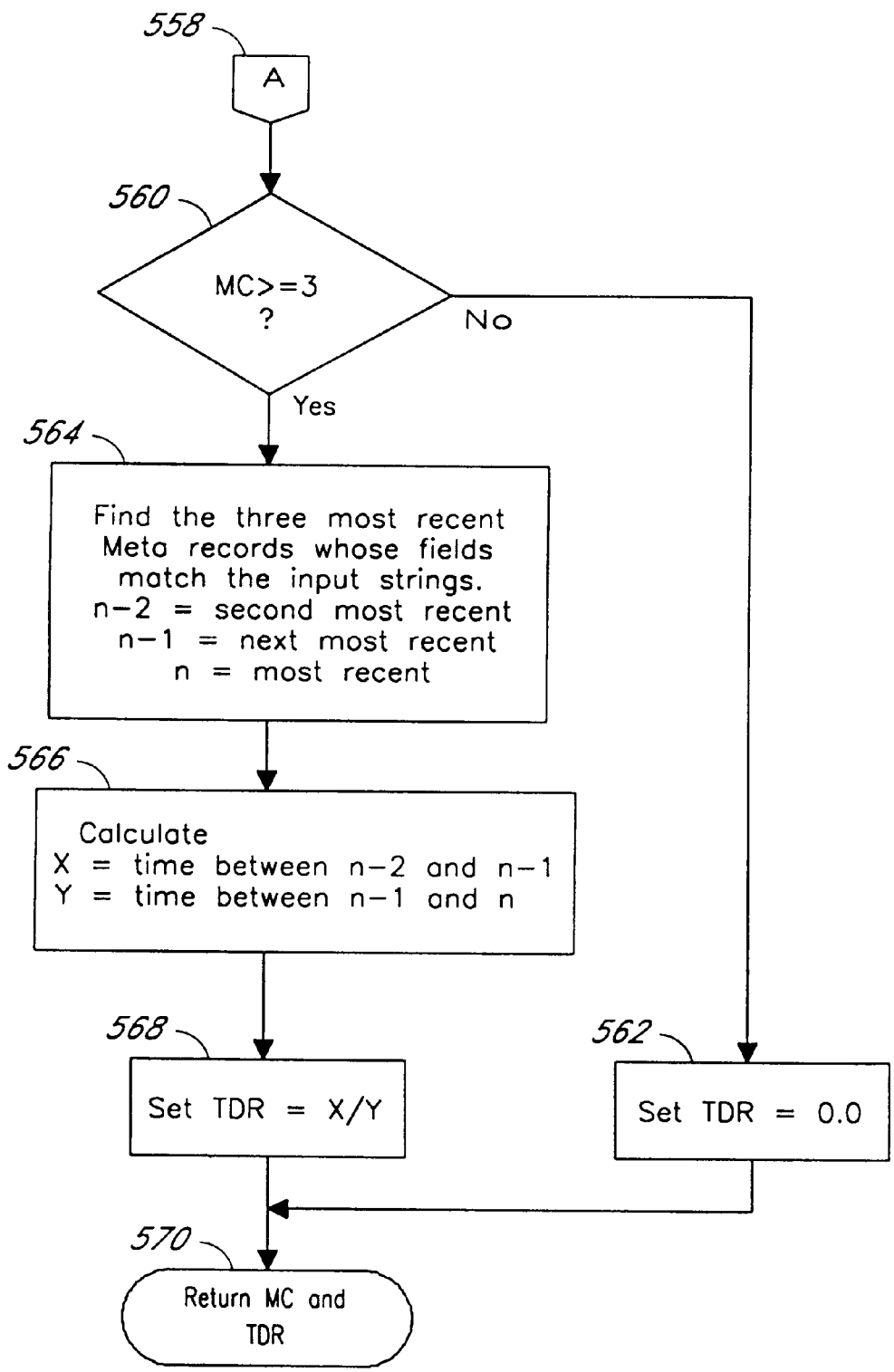

Referring now to FIGS. 11a and 11b, the meta function 500 defined in FIG. 10b will be described. One of the many ways the MDATA system 100 is qualitatively different from prior ways of providing medical advice is in its use of the "meta function." As mentioned earlier, "metal" refers to the system's ability to evaluate the patient's present problem in the context of his or her past use of the system. The meta function allows the system 100 to make an inference based upon the number and frequency of previous patient consultations (or, "medical complaints") and the system's previous diagnostic assessments. Every patient who has previously used the MDATA system 100 undergoes the meta analysis.

Input Parameters

The meta function 500 has five input parameters listed at state 540 as follows:

i. Problem String (PS)—a four character alphanumeric string indicating the patient's complaint. The first character of this string is taken from the Systems column of Table 2. For example, 'N' denotes the nervous system. The second through fourth characters identify an individual complaint, e.g., "NHDA" identifies headache. Other examples:
CCHP Chest Pain
NINJ Head injury
RINH Inhalation of toxic fumes ii. System String (SS)—a four character alphanumeric string that indicates the affected anatomic system. The first character is taken from the Systems column of Table 2. The second through fourth characters are encoded with subsystem identification, or filled with the '*' wildcard character. For example, "N***" will match all cases that involve the nervous system.

iii. Cause String (CS)—a ten character alphanumeric string that indicates the cause of the patient's complaint. The first character is taken from the Causes column of Table 2. The second through tenth characters are filled in as needed to more closely specify the cause of interest. A very broad example is "I*********" which denotes any infection. Other examples which illustrate how the cause string can become very specific:
IV Viral infection
IB Bacterial infection
IBN Gram negative bacterial infection
IBNM Meningococcal gram negative bacterial infection iv. Beginning Time ($T_1$)—a timestamp value which indicates the date and time to be used for the beginning of the time window under consideration.

v. Ending Time ($T_2$)—a timestamp value which indicates the date and time to be used for the end of the time window.

Table 2 lists code letters used as the first letter of the meta string parameter:

TABLE 2

| Causes | Systems |
|---|---|
| A - allergy | B - bones/orthopedics |
| E - environment | C - cardiology |
| I - infection | D - gastro-intestinal |
| M - mental | G - gynecology |
| P - poison | H - hematology (blood) |
| T - trauma | L - larynx (ENT) |
| V - vascular | N - nervous |
| X - genetic (chromosomal) | O - opthamology |
| Y - nutritional/metabolic/endocrine | R - respiratory |
| | S - skin |
| Z - tumor (cancer) | U - urology |

A set of meta function analyses involves the identification of trends in the patient's medical history. For example, if a patient went to his or her doctor with a history of gradually worsening headaches (either more painful, more frequent, or both) the physician would consider this worsening trend in his or her management of the case. The MDATA system 100 also does this.

Meta Analysis

The algorithm author passes input parameters to the meta function by using the keyword Meta, followed by the input parameters enclosed in parentheses. The format for the meta function is:

Meta(PS, SS, CS, $T_1$, $T_2$)

Two types of analysis are performed by the meta function:
i. Pattern Matching
ii. Time density i. Pattern Matching In pattern matching analysis, the meta function compares the input strings with the record fields in the patient's consultation history database 262. The use of the '*' wildcard character in the input string will cause the meta function to ignore the corresponding character position in the record field, thereby enabling the meta function to examine only the fields of interest. By providing input strings that are either general or specific, the fields of interest for analysis are selected. For example, Meta("NHDA", "***", "********", $T_1$, $T_2$) will cause the meta function to only consider past consultations for the problem of headache, regardless of the anatomic system and cause involved.

Through the use of a common syntax, the meta process supports four types or modes of pattern matching analysis, shown here through examples:

(a) Problem analysis:
Meta("NHDA", "***", "********", 06/01/93, 12/31/93)

Here the meta function will find the number of complaints of headaches that occurred between Jun. 1, 1993 and Dec. 31, 1993.

(b) Anatomic System analysis:
Meta("***", "D*", "**********", 06/01/93, 12/31/93)

Here the meta function will find the number of complaints involving the gastro-intestinal system between Jun. 1, 1993 and Dec. 31, 1993. For example, if a patient consulted the MDATA system 100 once for abdominal pain, once for vomiting, and once for diarrhea, but each on a different occasion, the system would recognize that these are all problems involving the gastrointestinal tract.

(c) Cause analysis:
Meta("***", "*", "********", 06/01/93, 12/31/93)

Here the meta function will find the number of complaints that were found to be caused by bacterial infection between Jun. 1, 1993 and Dec. 31, 1993. The problems (complaints) caused by bacterial infection could be in different parts of the body.

(d) Combination analysis:
Meta("NHDA", "***", "********", 06/01/93, 12/31/93)

Here the meta function will find the number of complaints of headache that were found to be caused by infection between Jun. 1, 1993 and Dec. 31, 1993.

ii. Time Density

If the pattern matching analysis finds at least three matching records in the patient's consultation history database 262, then the meta function performs a time density analysis. Time density refers to the amount of time between each consultation. If the amount of time between consultations is getting shorter, then the frequency of consultation suggests that the nature of the complaint is getting worse. Time density analysis reveals when a problem is getting better, and when it is getting worse.

Time density analysis uses the meta records that matched the pattern matching criteria. The computer designates the most recent meta record 'n', the next most recent is record 'n-1', and the second most recent is record 'n-2'. The time stamp of each meta record is examined, and two time difference values, X and Y, are determined according to the formula:

$X$=time difference ($n$-2, $n$-1)

$Y$=time difference ($n$-1, $n$)

The ratio of these time differences produces the time density ratio (TDR):

Time Density Ratio=X/Y

The significance of the time density ratio value can be seen through the following examples:

| Example 1: Time between consultations is the same. | |
|---|---|
| Consultation | Date of Consultation |
| n-2 | 06/01/93 |
| n-1 | 06/08/93 |
| n | 06/15/93 |

Calculate:
X=time difference (06/01/93, 06/08/93)=7 days
Y=time difference (06/29/93, 06/15/93)=7 days
Time Density Ratio=7 days/7 days=1.0

| Example 2: Time between consultations is getting shorter. | |
|---|---|
| Consultation | Date of Consultation |
| n-2 | 06/01/93 |
| n-1 | 06/22/93 |
| n | 06/29/93 |

Calculate:
X=time difference (06/01/93, 06/22/93)=21 days
Y=time difference (06/29/93, 06/22/93)=7 days
Time Density Ratio=21 days/7 days=3.0

When consultations are occurring at even intervals, then the TDR value is close to unity. If the frequency of consultations is decreasing, then the TDR value will be less than 1.0. This would be typical of a problem that is resolving itself. If the frequency of consultations increases, then the TDR value will be greater than one. In the second example, the TDR value of 3.0 indicates a consultation rate increase of three times during the analysis period. This would be typical of a problem that is rapidly getting worse.

Return Values

After the meta function returns, two local memory variables are installed in the symbol table and contain the results of the meta analysis:

i. Match Counter (MC)—an integer that contains the number of meta string matches found within the time window.

ii. Time Density Ratio (TDR)—a floating point value that expresses whether the frequency of meta string matches is increasing or decreasing.

After calling the meta function, the algorithm author can then make decisions based upon the values returned in these two memory variables.

For example:
Meta ("NHDA", "***", "********", 06/01/93, 12/31/93)
If MC>=3 then 100 else 101

The meta function counts the number of complaints of headache between Jun. 1, 1993 and Dec. 31, 1993. If the number of complaints found (MC) is greater than or equal to 3, then the evaluation process branches to node 100; otherwise it branches to node 101.

Another example:
Meta("***","*","********", 06/01/93, 12/31/93)
If TDR>=2.0 then 200 else 201 The meta function is invoked to count the number of diagnoses attributed to a cause of infection. If the infection caused diagnoses found have a time density ratio greater than or equal to 2.0, then the evaluation process branches to node 200; otherwise it branches to node 201.

Referring again to FIG. 11a, the meta function 500 initializes at state 540 by popping the input parameters off the run-time stack and storing them in local memory variables: PS for problem string, SS for anatomic system string, CS for cause string, $T_1$ for the beginning date and $T_2$ for the ending date. After the start state 542, the computer moves to state 544 and initializes the pattern match counter to zero.

The computer 102 then moves to state 546 wherein it begins the pattern matching analysis. The computer 102 reads the first meta record in the patient's consultation history database 262 and moves to a decision state 548 wherein it examines the record's timestamp. If the timestamp falls within the time window established by the input parameters $T_1$ and $T_2$, then the computer will move to state 550; otherwise it moves to state 554. At state 550, the computer 102 compares the contents of the meta record problem field with the input string PS, the meta record anatomic system field with the input string SS and the meta record cause field with the input string CS. If all these fields match the respective input strings, then the computer moves to state 552 wherein the match counter MC is incremented, and then the computer moves to state 554. If there is any mismatch between a meta record field and its respective input string, then the computer moves to state 554 and does not increment MC.

At decision state 554, the computer 102 determines if there are more meta records to process. If so, the computer 102 moves to state 556 wherein it reads the next record and then moves back to state 548 to perform the time window determination. The meta function iterates through this pattern matching until all of the meta records have been read. When there are no more meta records to be processed, the computer moves through off-page connector A 558 to a decision state 560 on FIG. 11b wherein a determination is made if the value of the match counter MC is greater than or equal to 3. If so, then the computer moves to state 564 wherein it begins the time density analysis.

At state 564, the computer 102 locates the three most recent meta records whose fields matched the input strings. The computer designates the most recent meta record 'n', the next most recent is record 'n-1', and the second most recent is record 'n-2'. The computer then moves to state 566 wherein it calculates X, the time difference between the timestamps of records n-2 and n-1, and Y, the time difference is between records n-1 and n. The computer 102 then moves to state 568 wherein it calculates the time density ratio (TDR) as the time X divided by time Y.

If the computer 102 determined at state 560 that there were less than three matches, then it would move to state 562 wherein it sets the value of the time density ratio (TDR) to 0.0, which indicates that the time density analysis could not be performed. At the completion of establishing the value of TDR at either state 562 or 568, the computer 102 moves to terminal state 570 wherein the meta process terminates, returns the match counter MC and the time density ratio TDR, and returns control to the evaluation process 254 (FIG. 10).

The interaction of the meta analyses for cause and for anatomic system can be conceptualized by means of a simple geometric metaphor. Consider a two dimensional array in which the causes of disease (trauma, infection, allergy/immune, and so forth) are placed on the "Y" axis, or ordinate, and the anatomic systems of the body (cardiac, respiratory, nervous system, and so forth) are placed on the "X" axis or abscissa. Disease then can be represented by, or is produced at, the intersection of the lines drawn from the applicable cause and the anatomic system.

Figure 24:
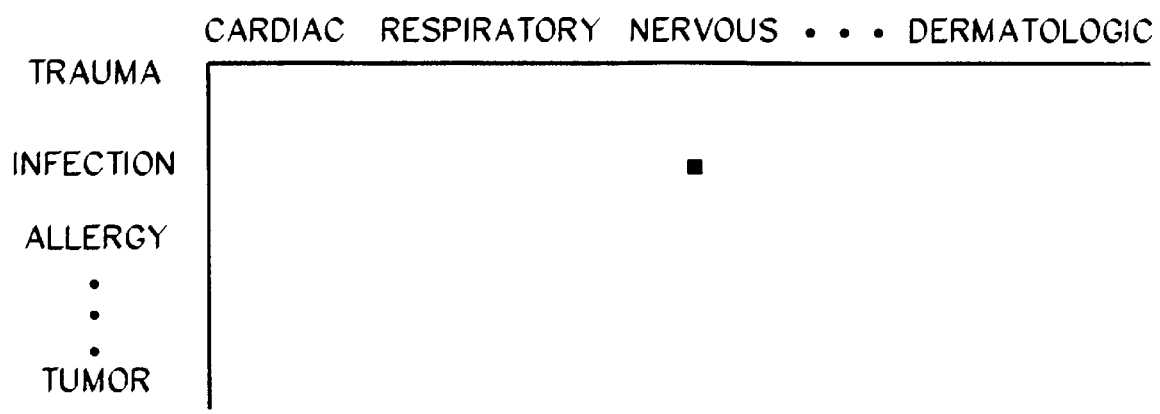
FIG. 24 is Table 3, a two dimensional array of causes of diseases plotted against anatomical systems.

As a very simple illustration, consider the two-dimensional array shown in Table 3 (FIG. 24).

The array of Table 3 shows an infection in the central nervous system represented at the intersection of the cause of disease (infection) and the anatomic system involved (the nervous system).

Of course, each cause of disease can be further divided into subcauses. For example, infection would be broken down (or subdivided) into bacterial and viral, and bacterial would be further broken down into gram positive and gram negative, and gram positive would be further yet broken down into streptococcus, and so on. The anatomic systems could be broken down in a similar way.

As a patient uses the system 100, and as the meta analyses for cause and for anatomic system attribute causes to disease processes and record the anatomic systems involved, a three-dimensional cube (a "meta cube") is produced composed of these stacked two-dimensional arrays. The "Z" axis coordinate of each layer is the time of the patient's consultation obtained from the system clock (i.e., the moment that the actual intersection of the cause and anatomic system occurs indicating the diagnosis).

The "meta cube" then represents a summation of the patient's interaction with the system 100 through time. Although much of the patient's past history is stored using ICD■9■CM codes as well as conventional text strings in fields of the patient's medical record, the "meta cube" technique allows very useful analyses to be done.

Using the same modeling metaphor, the "Z" axis coordinate can be used to represent the practice of medicine. Here the "Z" coordinate is again time, but in this representation, time refers to a spectrum of ages from pediatrics to geriatrics. Thus, each coronal plane represents specialties by time, e.g., pediatrics, adolescent medicine, adult, geriatric. A vertical plane describes a specialty by anatomic site, such as neurology or cardiology, while a horizontal plane describes a specialty which practice is bounded (subsumed) by (on) cause, such as oncology or infectious disease. To further this metaphor, the rapidity with which intervention is necessary could be a fourth dimension of the model, and the frequency of an occurrence of a disease is the fifth dimension. Ethical and moral responsibility could be a sixth dimension of the model.

Node Map Traverse Analysis

The MDATA system 100 uses a "neural net emulator" program to determine if patterns produced by patients, as they traverse down the nodes (creating "node tracks" of the algorithms in the course of a consultation, may be early predictors of disease. Somewhat like the "meta cube," the "node tracks" can be superimposed, rather than stacked, upon one another to create a two-dimensional array. This time, however, the pattern produced represents the sum of the patient's previous consultations. In the MDATA system 100, this is called a "node track traverse analysis."

For example, the MDATA system 100 may discover that the pattern that is produced when a patient consults the system, at different times, for episodes of diarrhea, cough, and oral candidiasis may be predictive of AIDS. Or, that the pattern produced when a patient consults the system for increased frequency of urination and weight loss may be predictive of diabetes mellitus.

XII. Mental Status Examination

Figure 16A:
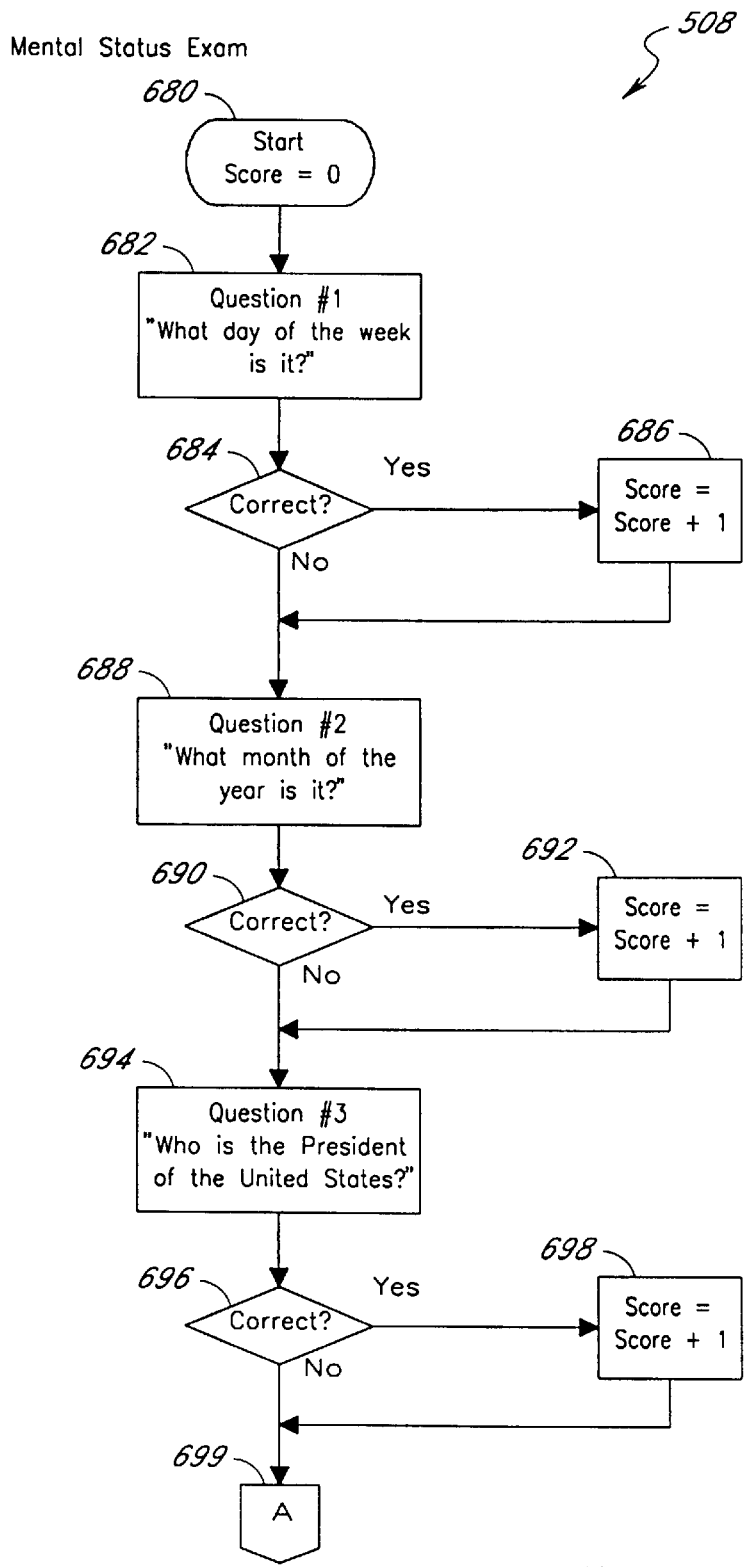
FIGS. 16a and 16b are a flow diagram of the mental status examination function 508 defined in FIG. 10b.
Figure 16B:
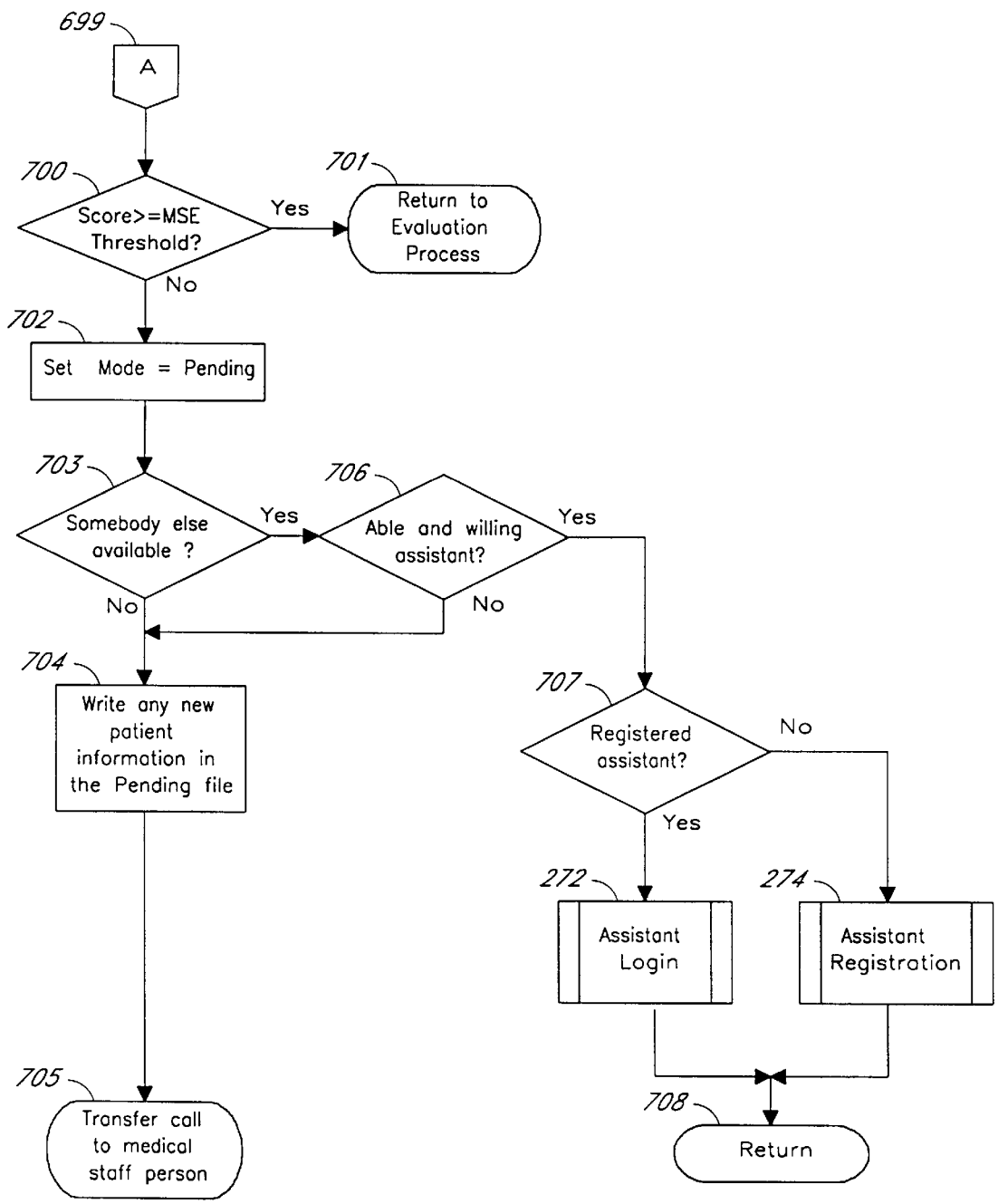

Referring to FIGS. 16a and 16b, the mental status examination function 508 defined in FIG. 10b will be described. The mental status examination is a series of questions used to assess the patient's orientation that allows the system 100 to determine the patent's ability to respond to questions and to follow advice. The examination is automatically incorporated into the dialogue of any problem whose presentation could include an altered level of consciousness. If an operator or nurse monitoring a telephone consultation at any time feels there may be a problem with the caller's ability to understand or respond to questions, the mental status examination may also be manually invoked.

If the MDATA system 100 determines that the patient is not sufficiently oriented based on the results of the mental status examination, the system 100 will ask to speak to someone other than the patient. If no one else is available, the MDATA system 100 can contact the emergency medical services system in the patient's area if the system knows the patient's present geographic position.

Beginning at a start state 680 of FIG. 16a, the computer 102 initializes the value of a variable Score to be zero. Moving to state 682, the computer asks the patient Question #1. In the presently preferred embodiment, the question is "what day of the week is it?" If the person answers the question correctly, as determined by a decision state 684, the computer 102 increments the value of Score by one. After Score is incremented or if the patient did not answer the first question correctly, the computer 102 moves to state 688 wherein the computer 102 asks the patient Question #2. In the presently preferred embodiment, the question is "what month of the year is it?" If the person answers the question correctly, as determined by a decision state 690, the computer 102 increments the value of Score by one. After Score is incremented or if the patient did not answer the second question correctly, the computer 102 moves to state 694 wherein the computer 102 asks the patient Question #3. In the presently preferred embodiment, the question is "who is the President of the United States?" If the person answers the question correctly, as determined by a decision state 696, the computer increments the value of Score by one. After Score is incremented at state 698 or if the patient did not answer the third question correctly, the computer 102 moves through off-page connector A 699 to a decision state 700 on FIG. 16b.

At decision state 700, the computer 102 compares the score to the mental status exam threshold at a decision state 700. If the score meets or exceeds the threshold, then the mental status exam returns to the evaluation process at state 701 and the diagnostic evaluation continues. If the score does not reach or exceed the threshold value, the computer 102 moves to state 702 wherein the operating mode flag is set to Pending. The MDATA system 100 will then ask, at a decision state 703, if someone else is available to continue the consultation. If no one else is available, any new information gathered up to this point in the session is saved to Pending file 269 at state 704 and then, at state 705, the telephone call with the patient is transferred to a medical staff person. If someone else is available, as determined at state 703, and is able and willing to continue the evaluation process of the patient, as determined at state 706, the computer 102 asks the person if he or she is a registered assistant at state 707. If the person responds "yes", the computer 102 invokes the assistant login process 272 at start state 940 on FIG. 12a. If the person is not a registered assistant, the computer 102 invokes the assistant registration process 274 at start state 1050 on FIG. 14a. After assistant registration or login, the computer 102 moves to terminal state 708 wherein the mental status examination process terminates and the evaluation process 254 resumes. At the end of the evaluation process 254, any new information gathered during the session will be written to the patient's past medical history file at state 348 or to pending file 269 at state 347 on FIG. 7d, depending on whether the session continued in real or pending mode. In the presently preferred embodiment, the value of Score could be zero, one, two, or three. Of course, in other embodiments, different questions to be asked of the patient may be utilized in the mental status exam function 508.

XIII. Semantic Discrepancy Evaluator Routine

Figure 17:
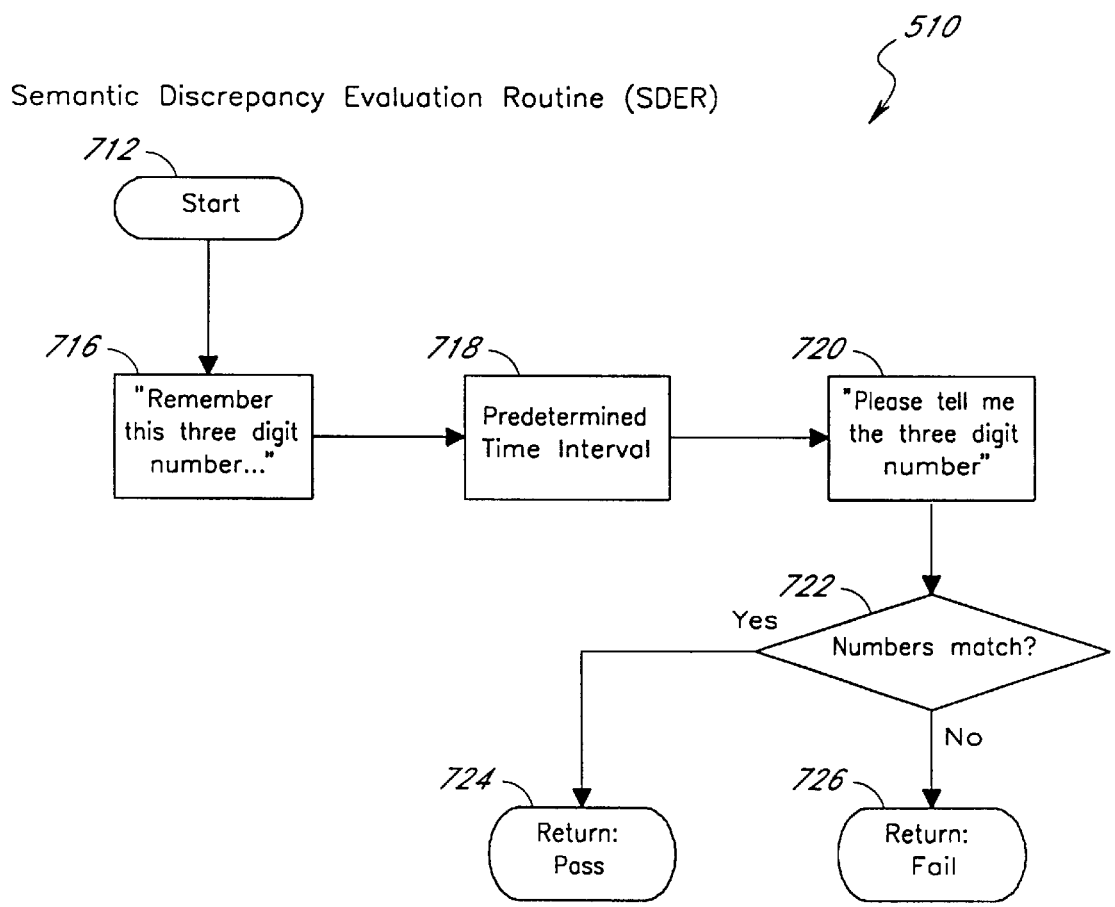
FIG. 17 is a flow diagram of the semantic discrepancy evaluator routine (SDER) 510 defined in FIG. 10b.

Referring to FIG. 17, the semantic discrepancy evaluator routine (SDER) 510 defined in FIG. 10b will be described. The SDER 510 uses one or more questions that ask for the same information at different times, and in other embodiments, in different ways. The answers given by the patient are then compared within the system 100 to help determine the mental status of the patient.

Beginning at a start state 712, the computer 102 moves to state 716 and recites a message to the patient. In the presently preferred embodiment, the message is "remember this three digit number. NUMBER", where the computer generates a random three digit number (i.e., in the range 100 to 999 inclusive) as NUMBER which is kept in a session memory variable.

Then, after a predetermined time interval at state 718, the computer 102 moves to state 720 and recites a request of the patient. In the presently preferred embodiment, the request is "please tell me the three digit number." The computer 102 then compares the number given by the patient in response to state 720 against the NUMBER kept in the memory variable at a decision state 722. If the numbers match, the computer 102 returns at state 724 with a status of pass to the evaluation process (FIG. 10b). If the numbers do not match, the computer 102 returns at state 726 with a status of fail to the evaluation process. In the presently preferred embodiment, if the return status of the SDER 510 is "fail", the evaluation process 254 automatically invokes the mental status examination function 508.

XIV. Past Medical History Routine

Figure 18:
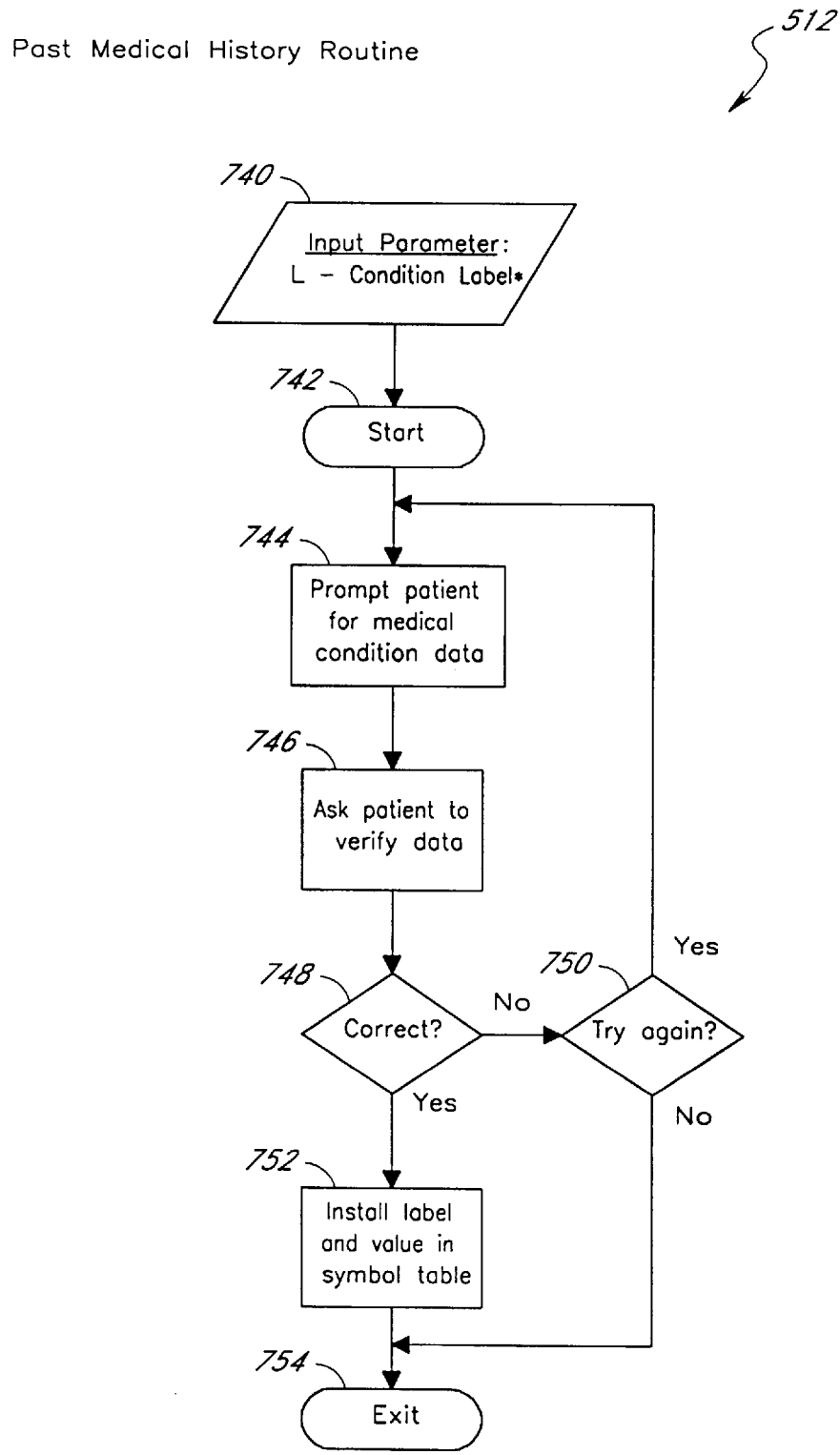
FIG. 18 is a flow diagram of the past medical history routine 512 defined in FIG. 10b.

Referring to FIG. 18, the Past Medical History Routine (PMHR) 512 defined in FIG. 10b will be described. The contents of a patient's past medical history file, which is part of the PMH database 268, are loaded to the symbol table when the patient logs in to the system 100. During the evaluation process 254, a TEST is performed by the computer 102 before a particular medical algorithm is initiated to verify that necessary items are present in the symbol table. The effect of a negative TEST result is that the system 100 prompts the patient to provide the missing past medical history information via the PMHR 512.

The PMHR 512 uses an input parameter "condition label" (L) as indicated at State 740. The "Condition label" is unique, e.g., PMHRLTB1 corresponds to the first PMH object tested in the croup (RLTB) algorithm: diagnosis for croup in children. The label is passed so that PMHR 512 knows what questions to ask. The ability of the system 100 to ask a past medical history question in the middle of the evaluation process 254 is a feature that saves the patient from having to answer the entire PMH questionnaire during the registration process. The boolean result, or scalar value, is stored in the symbol table under this label (PMHRLTB1), and the algorithm can use it in decision making, e.g., If PMHRLTB1=True Then 4310 Else 4320.

Beginning at a start state 742, the computer 102 moves to state 744 and prompts the patient for the missing medical condition data. Moving to state 746, the computer 102 repeats the information provided at state 744 and asks the patient if the repeated information is correct. Moving to a decision state 748, the patient responds by indicating whether the repeated information is correct. If the data is not correct, the computer 102 proceeds to state 750 to determine if the patient would like to attempt the data entry step again. If so, the computer 102 loops back to state 744 and prompts the patient for the data again. If not, the computer 102 returns at state 754 to the evaluation process (FIG. 10b).

If the newly-entered data is correct, as determined at state 748, the computer 102 advances to state 752 and installs the condition label (L).and the data value in the symbol table for the patient. The computer 102 then returns at state 754 to the evaluation process 254.

XV. Physical Self Examination

Figure 19:
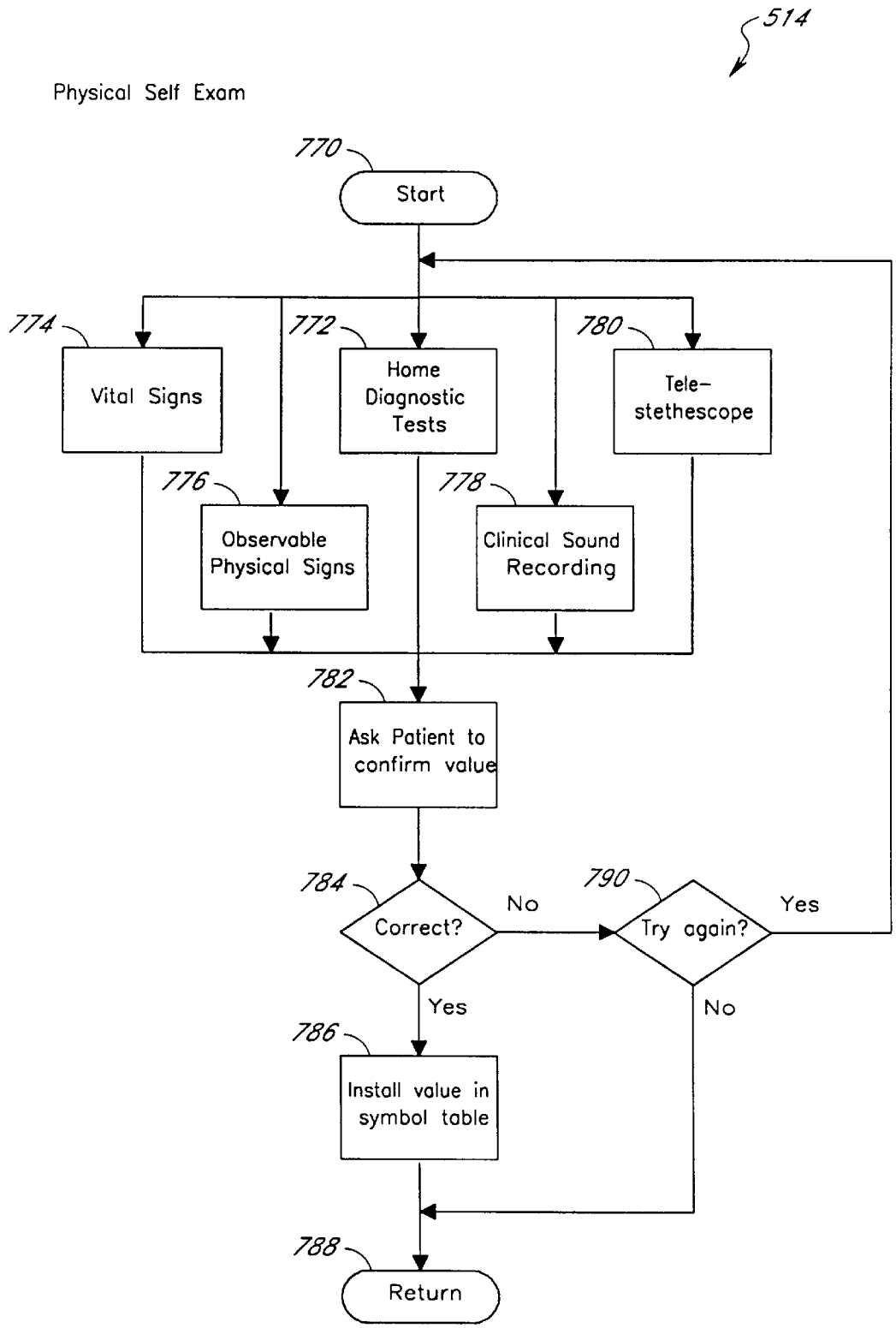
FIG. 19 is a flow diagram of the physical self examination function 514 defined in FIG. 10b.

Referring to FIG. 19, the Physical Self Examination function 514 defined in FIG. 10b will be described. A physical examination can actually be done by the patient under the direction of the MDATA system 100. The MDATA system 100 is designed to function primarily based upon responses to carefully crafted questions, i.e., history, and physical findings elicited from the patient. There are times, however, when the addition of certain laboratory tests can increase the accuracy of the diagnosis as well as help determine the appropriate treatment recommendations. For this reason, a MDATA system Home Diagnostic and Treatment Kit is available for use by patients. If the patient has the Home Diagnostic and Treatment Kit, including visual field cards, Snelling chart, and possibly the MDATA system's "telestethoscope" to assess intracranial or carotid bruits, this information will be used in the diagnostic process as well.

The MDATA system 100 is also able to play tones of different frequencies and intensities to emulate audiometric testing for hearing acuity. This allows, for example, the MDATA system 100 to detect the unilateral decrease in hearing caused by an acoustic neuroma.

Beginning at a start state 770, the computer 102 branches to one or more physical self examination procedures depending on the current problem and what equipment if any is available for use by the patient. These procedures include:

home diagnostic tests 772, vital signs 774, observable physical signs 776, clinical sound recording 778, and telestethoscope 780.

A variety of home diagnostic tests 772 are available for use by the patient. New advances in biotechnology, including a new generation of urine dipsticks such as a "Multistix 8 SG" produced by Ames and monoclonal antibody tests such as "ICON® STREP B" produced by Hybritech®, allow an entire spectrum of laboratory tests to be performed at home by the patient under the direction of the MDATA system. For example, urine dipsticks can be used to check for blood, nitrites, leukocytes, or leukocyte esterase indicating cystitis or a bladder infection.

In order to use much of the monoclonal antibody technology, however, a small amount of blood must be obtained by using a fingertip lancet. This is already successfully being done by diabetics at home who use a glucometer to measure their blood sugar after pricking their finger to get a small sample of blood.

The MDATA system Home Diagnostic and Treatment Kit also contains equipment to allow the patient, or someone else, to measure the patient's vital signs 774. A blood pressure cuff and thermometer are included with instructions for their use as well as instructions to measure pulse and respiratory rate.

The patient may be directed by the system 100 to observe various physical signs 776. For example, a headache patient will be asked to palpate their temporal artery area, and to look at themselves in the mirror to identify the ptosis and tearing of a cluster headache or to identify the steamy cornea that may occur with acute narrow angle glaucoma. As an example of how the MDATA system Home diagnostic and Treatment Kit could be helpful, consider a woman who (using the MDATA system's urine pregnancy test based on ICON® II HCG ImmunoConcentration™ Assay, produced by Hybritech®) finds out that she is pregnant. This is her first pregnancy. Later, when consulting the system for headache, a urine dipstick indicates protein in her urine and the measurement of her vital signs shows a significant rise in her blood pressure. This is a classic presentation of preeclampsia.

Instead of going to a doctor's office, patients could also use the MDATA system's Home Diagnostic and Treatment Kit to collect samples at home and then send them to a designated lab for analysis as needed. This saves time for the patient and is especially useful if the patient has difficulty in traveling. Costs should also be minimized in this type of laboratory analysis.

The MDATA system 100 records clinically relevant sounds 778 of a patient such as the cough of bronchitis, the seal bark cough of croup or the inspiratory stridor of epiglottitis. These sounds are digitized and stored in the patient's medical record. Then, using the re-enter feature of the system 100, the system can monitor, for example, a patient's cough over time to be sure that the cough is resolving as it should.

The general concept of recording and analyzing a cough is disclosed in the article A microcomputer-based interactive cough sound analysis system, C. William Thorpe, et al., published in Computer Methods and Programs in Biomedicine, 1991. The cough sound analysis system describes the filtering, amplification, recording, and software processing of a cough sound. The MDATA system 100 uses the telephone handset microphone in conjunction with an amplifier to procure the clinical sounds. These sounds are then transmitted to the system 100 where they are filtered, digitized using VP board 122 and recorded to a file in the patient medical history database 268 on the hard drive 152 (FIG. 1).

The MDATA system 100 is building a library of clinical sounds that allows patterns or profiles to be developed that relate the wave form of the clinical sound to the probability of a particular diagnosis. For example, the MDATA system 100 could compare the cough of a patient to the sound library to see if the cough of the patient is similar to those that eventually have been diagnosed as lung cancer.

In addition, the patient's record of the pronunciation of his or her name may be periodically recorded and compared to previous recordings. This allows the MDATA system 100 to potentially detect and evaluate the hoarseness that could be produced by a nodule on the patient's vocal cords.

A "tele-stethoscope" 780 is a device that allows the sounds a physician would hear through a stethoscope to be transmitted over the telephone. The tele-stethoscope 780 is functionally similar to that described in the 1992 Arthur D. Little report entitled "Telecommunications: Can It Help Solve America's Health Care Problems?". The tele-stethoscope 780 permits the MDATA system 100 to greatly expand the spectrum of its sound analyses to include heart murmurs, the bruits of intracranial aneurysms, breathing sounds like the wheezes of asthma and the rales of congestive heart failure, or even the bowel sounds of an intestinal obstruction.

There is more information in clinical sounds than can be represented by a two-dimensional pattern matching model. Transforms, e.g., Fourier, are used to shift different aspects of sounds into domains that can be quantified. The sounds are then pattern matched using an n-dimensional array. Consider a simple two dimensional array where time is represented on the X coordinate and amplitude is measured on the Y coordinate. For example, a cough may be recorded at two times several days apart. In this example, the computer 102 superimposes the waveform from one cough upon the other cough. The non-overlapping parts of the pattern both above and below represent the difference in the domain being measured between the two sounds. The area under these two curves is integrated to obtain the area. The sum of the areas of the two curves represents the difference between the two sounds in the domain being measured. The resultant area is then subjected to one or more sensitivity factors which are discussed hereinbelow. Hence, the more sensitive the system, the sooner it makes a match.

In a similar way, a sound pattern may be considered with time on the X coordinate and frequency on the Y coordinate. The same methodology is used to quantify the differences between the two curves. Thus, in a similar way, all aspects of sound can be measured.

In this pattern matching scheme, different weights are given to the different aspects of the sound depending upon which clinical sound is measured. In most sounds, the amplitude and frequency are the most important aspects. The weight or the relative importance of an aspect is different for each of various clinical sounds, such as heart murmurs, bruits, wheezes, coughs, stridor and so forth.

When value(s) from any of the procedures 772–780 are procured by the system 100, the computer 102 moves to state 782, recites the value and requests the patient to confirm the value. If the patient indicates that the value is correct, as determined at a decision state 784, the computer 102 proceeds to state 786 and installs the value into the symbol table associated with the current patient. If the value is not correct, as determined at decision state 784, the computer 102 proceeds to state 790 to determine if the patient would like to try providing the value again. If so, the computer 102 loops back to the beginning of the function 514. If the patient does not wish to try again, as determined at state 790, or if state 786 is completed, the computer 102 returns at state 788 to the evaluation process (FIG. 10b).

Figure 20:
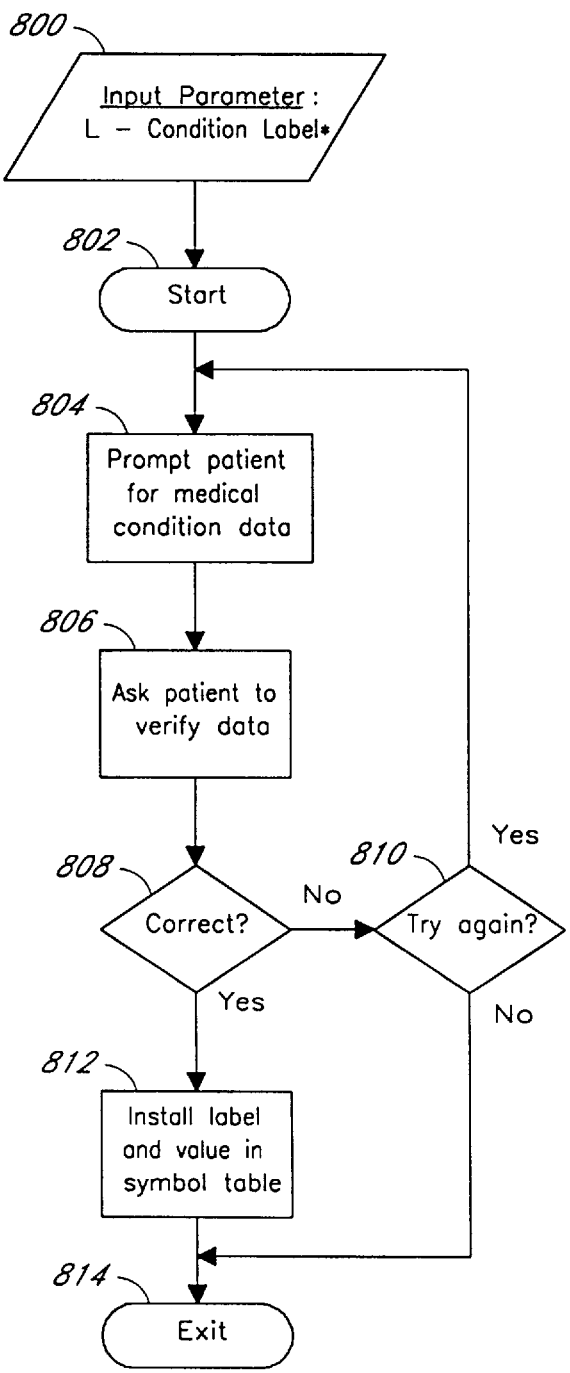
FIG. 20 is a flow diagram of the patient medical condition routine 516 defined in FIG. 10b.

Referring to FIG. 20, the Patient Medical Condition Routine 516 defined in FIG. 10b will be described. In the course of executing a particular medical algorithm in the evaluation process 254 (as shown at state 506), the computer 102 may request additional medical condition information of the patient. This information reflects the current condition of the patient, which is in contrast to the information requested by the past medical history routine 512 (FIG. 18) for past history information. The states 800 through 814 of the routine 516 are essentially the same as states 740 through 754 of routine 512, except that in routine 512 the condition label (L) denotes a value for which a past medical history question is to be asked during the evaluation process, while in routine 516 the condition label denotes a new value desired by the algorithm. Therefore, states 800–814 are not further described herein.

XVI. Symptom Severity Analysis

Figure 21:
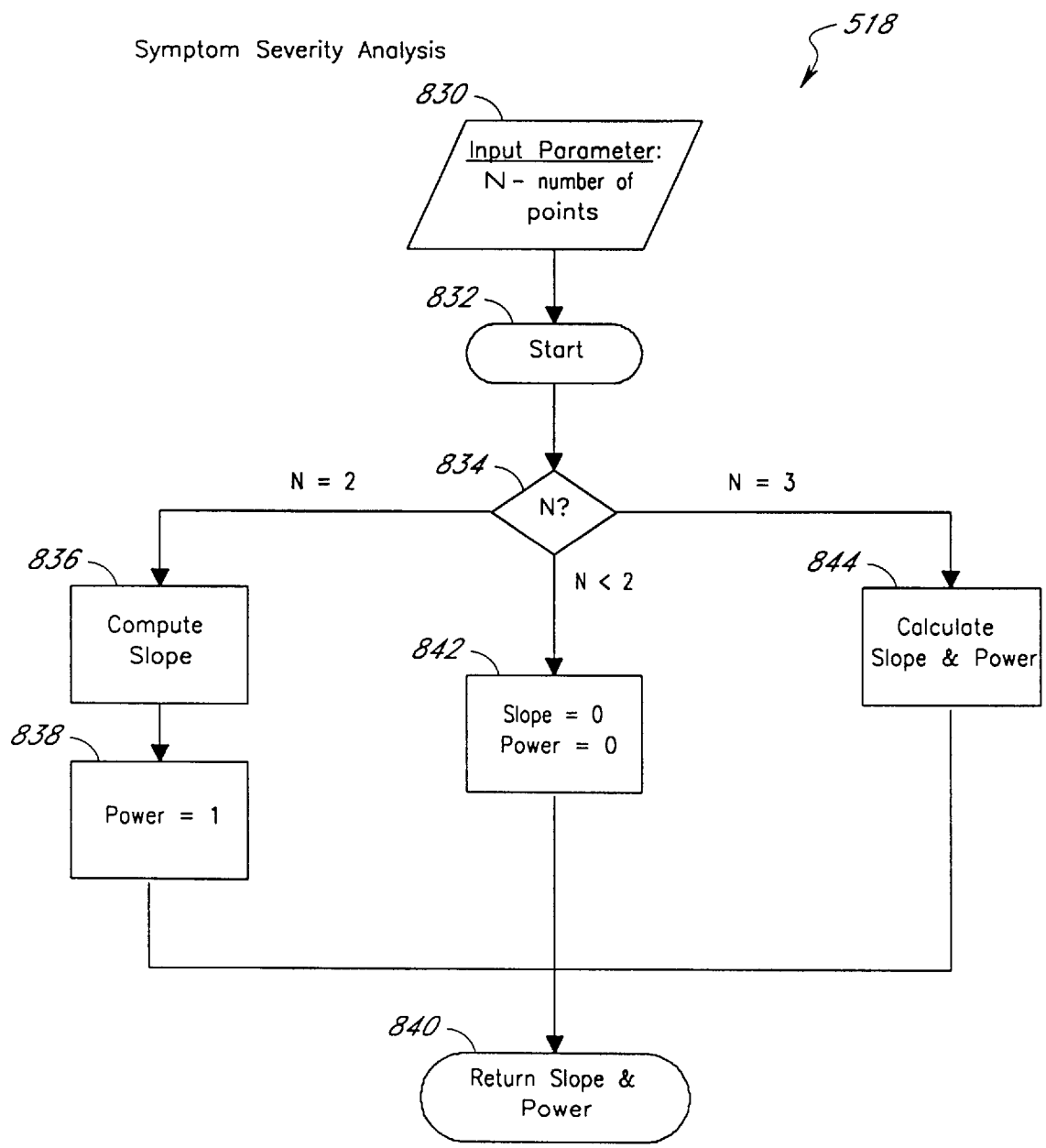
FIG. 21 is a flow diagram of the symptom severity analysis function 518 defined in FIG. 10b.

Referring now to FIGS. 10a, 10b, and 21, the symptom severity analysis function 518 defined in FIG. 10b will be described. A review and further description of the re-enter feature, which is associated with symptom severity analysis, is also provided here.

An important feature of the MDATA system 100 is its ability to follow or monitor a patient over time. If the MDATA system 100 is in the process of diagnosing a patient's complaint but is not certain what action should be taken (states 520–522 of FIG. 10b), system 100 may ask the patient to re-enter the system at a designated time, usually within a few hours.

When the patient calls the MDATA system at the designated time, the system takes the patient through the initial problem screening questions (state 483 of FIG. 10a) in order to exclude those problems that require immediate medical attention. The system detects that the patient is a re-enter case (state 490 of FIG. 10a), and then determines the re-entry point in the evaluation process based upon the patient's previous interaction with the system (state 492 of FIG. 10a). For example, if the MDATA system established a diagnosis of migraine, that is, if both the probability of migraine and the probability of confirmation of migraine reached threshold values, the patient would not repeat the diagnostic process, which is the usual case.

Occasionally, however, a patient for whom a diagnosis has not been established will be asked to re-enter the system 100. This patient is again asked the diagnostic screening questions, in addition to the initial screening questions (state 306 of FIG. 7a) and problem screening questions (state 483 of FIG. 10a). If the MDATA system 100 is not able to establish a diagnosis for a re-enter patient, he or she is referred to a physician for further evaluation.

In addition to the re-enter feature, the MDATA system 100 has the capability to call patients back in order to monitor their progress. The same trending methodologies are used regardless of who initiates the call, i.e., the system or the patient. Using this capability, the MDATA system 100 can provide regular or periodic monitoring of elderly patients in their homes as well as inform patients when a new therapy becomes available.

Many problems for which the MDATA system 100 offers advice have absolute thresholds for the initial quantization of the severity of a symptom. For example, chest pain that is described by a patient as being 10 on a 10-scale of severity, would reach the problem-specific initial symptom-severity threshold and would mandate a consultation with a physician.

Interestingly, with headache, an initial severity characterized by the patient as 10 on a 10-scale would not, in itself, necessarily require an immediate consultation with a physician. If, in addition, the headache came on suddenly and, as was mentioned earlier, was described as the worst headache of the patient's life, the MDATA system 100 would consider this to be suggestive enough of a subarachnoid hemorrhage to advise an immediate consultation with a physician.

Continuing in the headache example, after a re-enter patient with an established diagnosis is asked the initial and problem screening questions, the MDATA system 100 again assesses the severity of the patient's headache. Reassessing the severity of the headache, by having the patient re-enter the system, establishes two points of reference. The system 100 is now able to analyze any changes in the level of severity as well as calculate the rate of change in severity over time.

The symptom severity analysis function 518 has a Number of Points (N) as an input parameter as indicated at state 830. Number of Points refers to the points of reference established during the initial consultation for a particular problem and during subsequent re-enter consultation(s). Beginning at a start state 832, the computer determines the value of (N), i.e., the number of reference points, at a decision state 834. If it is determined that N=2, the computer 102 moves to state 836 to compute the slope of a line connecting the two reference points using standard mathematical techniques. Proceeding to state 838, a variable named Power is set to be one because only two reference points are used at state 836. The computer 102 returns at state 840, with output parameters Slope and Power as determined by function 518, to the evaluation process (FIG. 10*b*).

Using the returned Slope and Power parameters in the evaluation process 254, if the MDATA system 100 determines that the severity of the headache, for example, is increasing too rapidly, that is, if a slope of the line connecting two points on a graph of the severity reaches a set threshold, system 100 will make an appropriate recommendation.

If the MDATA system 100 finds that the severity of the headache is staying the same or is getting worse but is doing so at a relatively slow rate, it may ask the patient to re-enter the system a second time (i.e., for a third consultation), usually within a shorter period of time. The third consultation gives the MDATA system 100 three points of reference from which to trend the severity of the headache. Thus, when the function 518 is called by the evaluation process, the value of (N) is three, as determined at state 834, and the computer 102 branches to state 844. At state 844, the computer 102 determines the slope and power of a line connecting the three reference points. The presently preferred embodiment uses the well-known Runge-Kutta method, which is a numerical approximation technique for solving differential equations. Other embodiments may use other well-known, standard curve fitting functions at state 844.

If the system 100 determines that yet one or more additional consultations, i.e., beyond three consultations, are desired, e.g., to establish a trend with certainty, it will again request the patient to re-enter the system at a later time. In this situation, the three most recent reference points are used in the calculation at state 844.

The system 100 then performs a "sequential symptom-severity slope analysis" to determine if the symptom is getting worse too rapidly as follows. The slopes of the lines connecting the first and second point, the second and third point, and then the first and third point are calculated. If any of these reach a problem-specific threshold, the appropriate recommendation is given.

If the sequential symptom-severity slope analysis does not reveal the need to seek medical attention, then the MDATA system 100, in addition to calculating the rate of change in the severity of the symptom with respect to time (the slope analysis), now calculates the rate of change of the rapidity with which the headache is getting worse. This is the first derivative.

Figure 25:
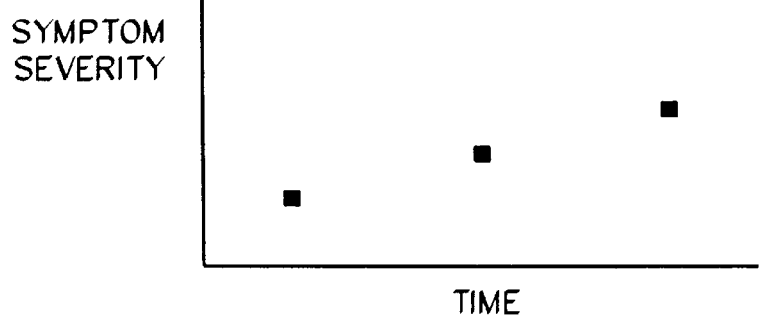
FIG. 25 is Table 4, an exemplary plot of symptom severity versus time.

Table 4 (FIG. 25) illustrates this relationship below. Time maps onto the "X" axis and the symptom's severity maps onto the "Y" axis.

Note that a line connecting these three points forms a gently sloping straight line. The MDATA system 100 using this data determines that, although the symptom is getting worse, it is doing so in an arithmetical or linear way. That is, although the severity of the symptom is increasing, the symptom's rate of change is not increasing.

Figure 26:
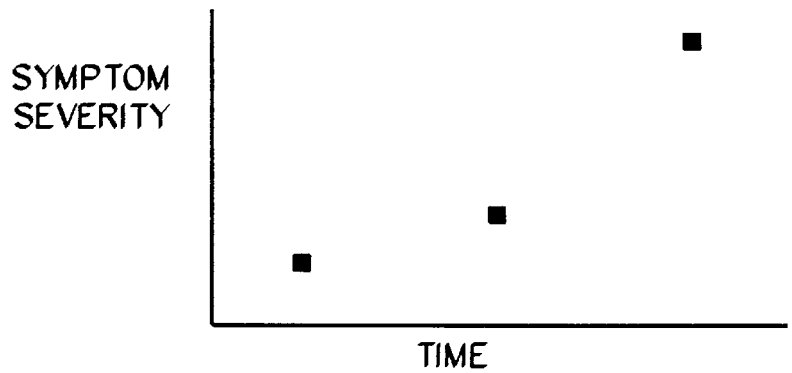
FIG. 26 is Table 5, another exemplary plot of symptom severity versus time.

In contrast, a line connecting the three points on the graph of Table 5 (FIG. 26) forms a sharply upturned curve.

The MDATA system 100 using the data of Table 5 determines that, not only is the symptom rapidly getting worse, but more significantly, the rate at which the symptom is getting worse is also increasing. In the MDATA system 100, this analysis is termed an "exponential symptom-severity filter." All patients who re-enter the system a second time are subjected to this analysis.

It is important to note that the severity of a problem, e.g., a headache, is not necessarily related to the seriousness of the underlying cause. The MDATA system 100 is programmed such that when any symptom gets rapidly worse, medical intervention is frequently advised as necessary. This concept is valid for many symptoms.

Returning to the symptom severity analysis function 518 (FIG. 21), if the function 518 is called with N=0, or N=1, the computer branches to state 842. At state 842, the Slope and Power parameters are set to zero, and the computer 102 returns these parameters at state 840 to the evaluation process (FIG. 10*b*). The values set at state 842 essentially flag an error condition that is acted on by the evaluation process 254.

XVII. Treatment Table

Figure 22:
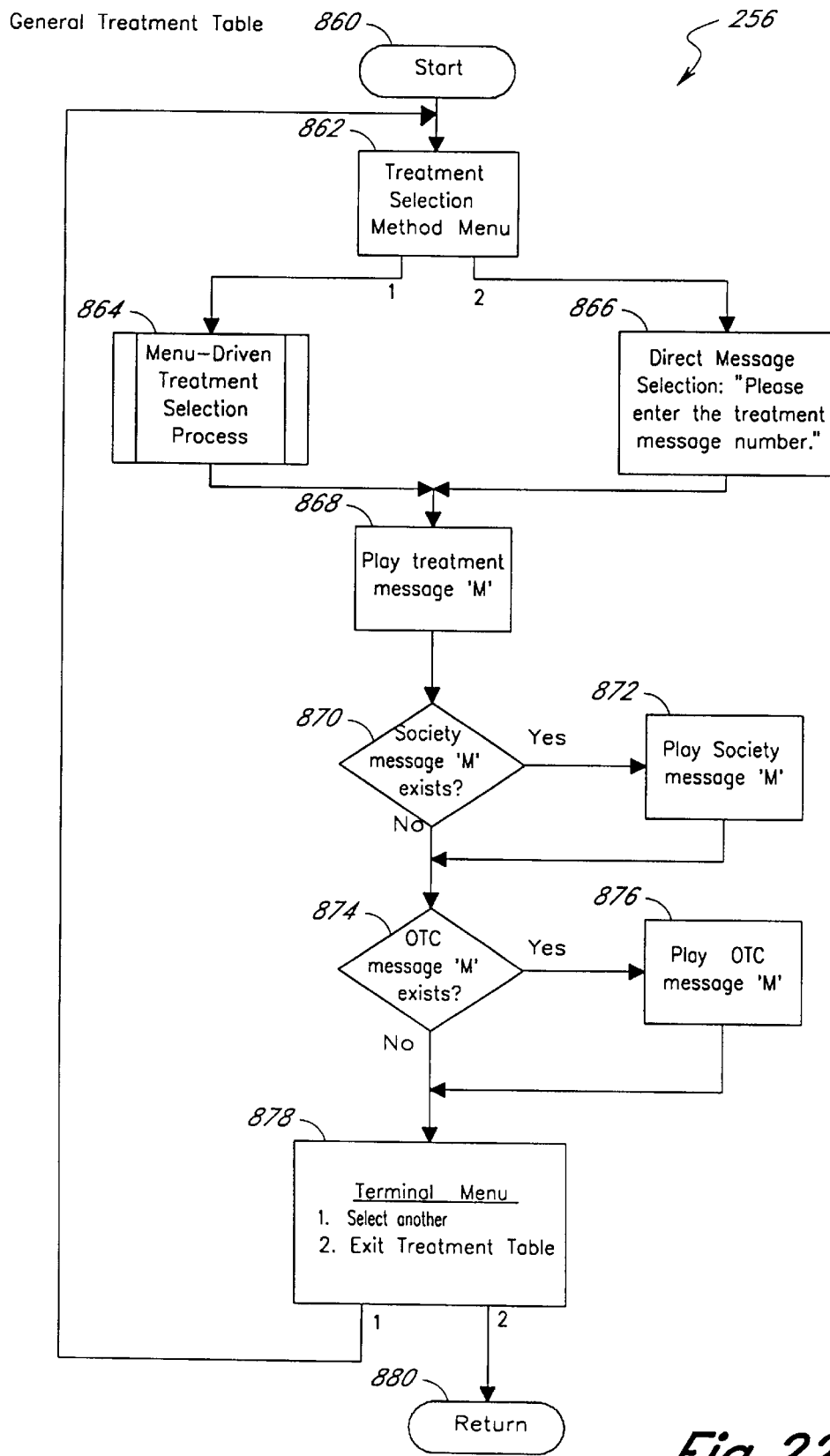
FIG. 22 is a flow diagram of the treatment table process 256 defined in FIG. 7d.

Referring to FIG. 22, the Treatment Table process 256 defined in FIG. 7*d* will be described. The MDATA system 100 is modularized in its approach to diagnosis and treatment. In medicine, diagnosis simply means figuring out what is causing the problem, and treatment refers to what action should be taken once the cause of the problem is known.

Diagnosis is composed of history, physical examination, imaging studies, and laboratory tests. Again, history is by far the most important factor in making the diagnosis. In fact, in medical school, students are taught that if they don't have a good idea of the diagnosis by the end of the history, they are doing something wrong.

The treatment side of medicine is conceptually different from diagnosis in that, while the basic principles of making the diagnosis remain the same, treatment is continually changing. Treatment is fundamentally a "look-up" table with the diagnosis, age and sex on the left and the most current treatment on the right as shown in Table 6. Or, treatment can be thought of like the cubbyholes or boxes of a post office. Each individual box holds the treatment for a given disease. The information given is age and sex specific. The contents of the box are constantly changing, but the location of the box does not. For example, what is thought to be the best antibiotic to treat meningitis in a two-year-old child could literally change from week to week as more antibiotics are developed and approved or more controlled studies are published.

TABLE 6

Simplified TREATMENT TABLE Example

| Diagnosis | Treatment |
|---|---|
| meningitis in a two-year old child | antibiotic of choice as of current date |

The MDATA system 100 maintains a treatment table that can be updated instantaneously to provide the most current treatment recommendations.

The treatment table can be directly accessed by patients who already know their diagnosis. For example, asthma patients can consult the system as often as they wish to see what the absolute latest treatment is for their condition. In fact, links are maintained between the treatment table and the patient medical history files 268. In this way, when a new treatment is introduced for any of the ICD■9■CM codes listed in the MDATA system 100, patients can be contacted and asked to either call the system 100 back at their convenience or have the MDATA system 100 fax or mail the information to them. The MDATA system 100 can also notify patients' doctors when a new treatment is identified.

The concept of using a table is also helpful with regard to two aspects of the diagnostic process that often do change: the imaging modality of choice (like X-ray, Computerized Tomography (CT), Magnetic Resonance Imaging (MRI)), and the laboratory test(s) of choice. Therefore, the MDATA system 100 also maintains a table for imaging modality of choice as well as laboratory test(s) of choice in the work-up or diagnosis of a particular complaint. By modularizing these aspects of the diagnosis, as new imaging techniques, like Positron Emission Tomography (PET) scanning, and new laboratory tests, like recombinant DNA technology, are discovered, only the tables have to be altered, not the medical algorithms themselves.

The treatment table will be further described in a general way as process 256 in FIG. 22. The treatment table process 256 begins at start state 860 and proceeds to state 862 wherein the computer prompts the caller to choose a treatment selection method:

i. Treatment selected from layered menus, or
ii. Treatment selected via direct entry of a catalog number.

The first selection method entails the use of the menu driven treatment selection process 864 which will be described hereinbelow in conjunction with FIG. 23. The second selection method at state 866 uses a treatment table catalog message number. This catalog is part of the patient information package, a section of which appears in Table 7.

The treatment table catalog is organized by anatomic area and diagnosis, and when applicable, by age and gender. After the patient selects a catalog number, the computer 102 stores the selection in a memory variable 'M'. As an alternate selection method, the system 100 allows the patient to directly enter the ICD■9■CM code for their problem. In this case, the computer 102 will look-up the ICD■9■CM code in an internal cross-reference table to identify the catalog number, and set the memory variable 'M' to this catalog number.

TABLE 7

Portion of Treatment Table Catalog

| NEUROLOGY Diagnosis | Message |
|---|---|
| Epilepsy | 1101 |
| Meningitis | |
| 2 years old & younger | 1201 |
| over 2 years old | 1202 |
| Depression | |
| Male | |
| Under age 50 | 1301 |
| 50 years and older | 1303 |
| Female | |
| Under age 50 | 1302 |
| 50 years and older | 1304 |

Once the value of the memory variable 'M' is established by process 864 or state 866, the computer 102 moves to state 868 and plays treatment message 'M' to the patient. At the conclusion of treatment message playback, the computer 102 moves to a decision state 870.

At state 870 the computer 102 checks for existence of society message 'M'. The society message category contains information about organizations that assist patients with a particular disease. If the society message 'M' does not exist, the computer 102 moves to a decision state 874.

Otherwise, the computer 102 will move to state 872 wherein it plays society message 'M' to the patient. At the end of the society message 'M', the computer moves to state 874.

At state 874, the computer 102 checks for the existence of an over-the-counter (OTC) message 'M'. The OTC message category contains information about generally available over-the-counter medications and home treatment for a particular diagnosis. If the OTC message 'M' does not exist, the computer moves to state 878. Otherwise, the computer 102 moves to state 876 wherein it play OTC message 'M' to the patient. At the end of the OTC message 'M', the computer 102 moves to state 878.

At state 878 the computer 102 plays a terminal menu to the patient which allows the patient to either select another treatment, or to exit from the treatment table process 256. If the patient wishes to hear another treatment message, the computer 102 moves back to the treatment selection method menu state 862. If the patient wishes to exit the treatment table process 256, the system moves to state 880, wherein the treatment table process 256 terminates and returns to the top level flow (FIG. 7d) at state 344.

An example of the treatment, society and OTC messages for epilepsy are given in Table 8. Note that since the OTC message is empty, the computer 102 would skip over the OTC message playback and proceed directly to the terminal menu.

TABLE 8

Treatment Table Messages for Epilepsy

Treatment Message

As of 12/20/93, according to Emergency Medicine:
Concepts and Clinical Practice, Third Edition, by Drs. Rosen,
Barkin, et. al., pages 1800 and 1801, the initial treatment
of generalized tonic-clonic seizures, i.e. grand mal
seizures, is as follows:
After efforts to discover and treat acutely correctable
causes like hypoglycemia, the following pharmacologic agents
are indicated:
1    Intravenous administration of lorazepam, with a
    loading dose of 0.1 mg/kg and an infusion rate not
    to exceed 2 mg/min.
Which is usually followed by:
2.   Intravenous administration of phenytoin, with a
    loading dose of 15 to 18 mg/kg and an infusion
    rate not to exceed 0.75 mg/kg per minute.
If lorazepam is not effective, and in those individuals
allergic to phenytoin:
3.   Intravenous administration of phenobarbital, with
    a loading dose of 8 to 20 mg/kg and an infusion
    rate not to exceed 0.75 mg/kg per minute.
If the above is not successful:
4.   A neuromuscular blocking agent like pancuronium,
    with an intravenous dose of 0.03 to 0.1 mg/kg.
5.   Intravenous administration of paraldehyde, with a
    loading dose of 0.1 to 0.15 ml/kg, diluted with
    saline to a 4% to 6% solution and slowly infused
    over 1 hour.

Society Message

"For further information on epilepsy, contact:
Epilepsy Foundation of America
1828 L Street, N.W., Suite 406
Washington, D.C. 20036
(202) 293-2930

In addition to the national headquarters, there are 100 local chapters. The San Diego chapter can be contacted at (619) 296-0161."

OTC Message

None.

Figure 23:
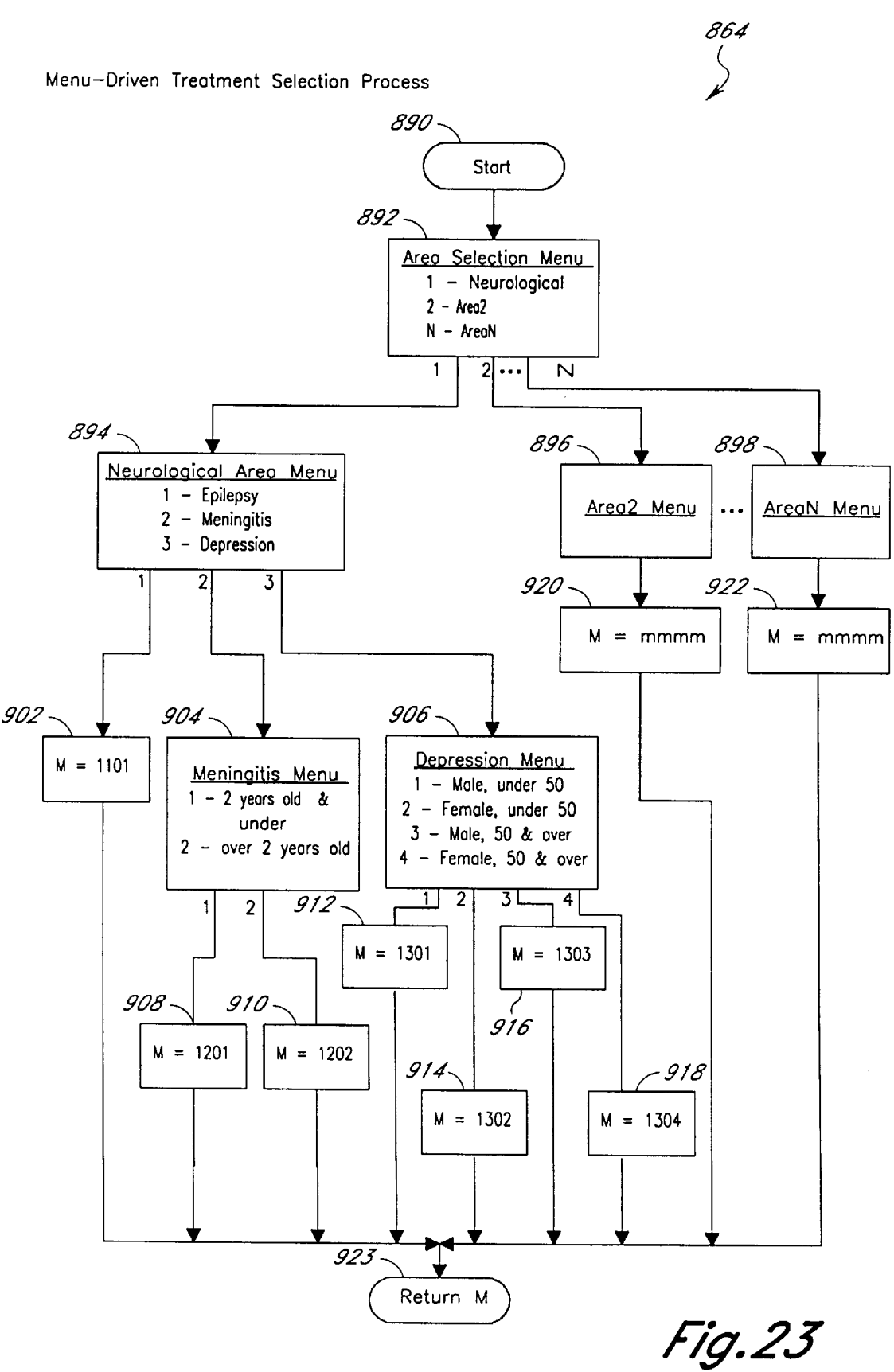
FIG. 23 is a flow diagram of the menu-driven treatment selection process 864 defined in FIG. 22.

Referring now to FIG. 23, the menu-drive treatment selection process 864 defined in FIG. 22 will be described.

The menu-driven treatment selection process 864 begins with start state 890 and proceeds to state 892 wherein the computer 102 recites an area menu to the patient and requests selection of one area. The complete menu is not shown in state 892. The areas are arranged by anatomic system. For example, if a patient has epilepsy, the patient can simply select this from the anatomic system menu for the neurological system.

Based on the patient's selection, the computer 102 branches to a selection area menu state, such as neurological area menu state 894, wherein the computer 102 recites a list of diagnoses to the patient and requests selection of a diagnosis. In some cases the diagnosis is further subdivided by gender, age or both gender and age. At state 904, for example, for a diagnosis of meningitis, the computer 102 would prompt the patient to select from a secondary menu between a treatment for a child two years old or younger and a treatment for somebody over two years old. Then, based on the patient's selection, the computer 102 sets a memory variable 'M' to the value of the selected diagnosis message number at state 908 or 910. State 906 is another example secondary level menu which has four choices based on gender and age. These four choices are associated with four states, 912, 914, 916, 918, wherein the computer 102 sets the memory variable 'M' to the value of the diagnosis message number that was selected at state 906. After the catalog number has been stored in memory variable 'M', the computer 102 moves to return state 923 wherein the menu-driven treatment selection process terminates and returns control to the treatment table process 256.

Area2 menu 896 and AreaN menu 898 are indicative of menus similar to menu 894 but for different anatomic systems. Menu 896 and 898 may have secondary menus, similar to menus 904 and 906 under menu 894. Then, states 920 and 922 are indicative of the computer 102 setting memory variable 'M' to the value of the diagnosis message number selected from the parent menu 896 or 898, respectively.

XVIII. The MDATA System Paradigm

The MDATA system paradigm is based on several fundamental principles. They are as follows:

Centralization of medical information

Accessibility of medical information

Modularity of medical information

Modifiability of the system.

As mentioned earlier, one of the purposes of the MDATA system 100 is to bring together highly qualified medical experts, encode their knowledge in a central location, and make this information available to everyone.

Although the issue of accessibility has been discussed several times, it is important to understand its significance. Accessibility in the MDATA system 100 refers both to the way in which the medical information can be retrieved from the system 100 by non-medically trained personnel as well as to the need for people everywhere to easily and promptly obtain medical information. By using the already established worldwide telecommunications network, the MDATA system 100 can provide universal and nearly instantaneous access to high quality, 100%-consistent medical advice.

In the MDATA system 100, the concepts of modularity and modifiability are inextricably intertwined. Modularity is the key to the MDATA system's ability to provide patients with the most current medical information available. The MDATA system's modular design and object oriented techniques allow the individual components of the system to be modified or updated without generating a ripple effect on other information in the system 100.

In contrast, the print media suffers from an inability to quickly adapt to changing information. Once a book or journal is published, it cannot be modified until its next publishing date. The MDATA system 100, however, can be modified within hours of a new discovery in medicine. Easy modifiability is another way in which the MDATA system 100 is qualitatively different from previously published algorithms.

Once the medical algorithms for the MDATA system 100 are written and programmed, they can then be continuously updated and refined as advances in medicine are made. Unfortunately, physicians today are simply not able to keep up with the explosion of new medical information and technology. This ability to nearly instantaneously modify the MDATA system 100 is a powerful feature of the system.

It is presently possible for a computer to search the world's medical literature daily. Any articles pertaining to a particular topic can automatically be requested and the information used to update the system.

In addition, the MDATA system 100 is currently using optical character recognition technology to digitize its medical database. Then, using indexing techniques, the MDATA system 100 is able to search for and retrieve any information desired. For example, the system can search for the character string "headache" and retrieve any amount of surrounding text or graphic information. This information is then collected, collated, printed and referred to the physician(s) maintaining the headache algorithm. This process will become easier as more of the world's medical literature is digitized.

Global Factors—Sensitivity and Selectivity

Another way in which the MDATA system is modifiable is in its use of global sensitivity/selectivity factors. As with every decision, there is always a balance to be achieved between risk and benefit, and so with the MDATA system 100. One of the questions the MDATA system 100 tries to answer is whether the patient needs to be seen immediately by a physician. This leads to this discussion about sensitivity and selectivity.

Sensitivity and selectivity are statistical terms that refer to how accurately a decision can be made. In this case, sensitivity refers to the number of patients which the MDATA system 100 did not think needed to be seen by a physician but that actually did.

If the program were to be so sensitive that no disease process that eventually required meaningful physician intervention would be treated at home (no false negatives), then every single complaint would necessitate a visit to the doctor, which is a useless system. On the other hand, too selective a system (no false positives) i.e., no unnecessary visits to the doctor's office, would necessitate that an attempt be made at home treatment for every complaint, which is a useless and dangerous system.

So again, a balance must be reached between these two ends of the spectrum. To achieve this, the sensitivity/selectivity ratio of the entire MDATA system 100 can be changed by setting or tuning a plurality of sensitivity factors. These sensitivity factors affect the following functions: meta thresholds, reenter horizon threshold, frequency of call back, symptom-severity filters, sequential slope filters, exponential symptom-severity filters, and probabilities of diagnoses in the treatment table. In addition, as in the headache example, the scoring of the screening questions already weighted is modulated or modified by the sensitivity factors.

Figure 27:
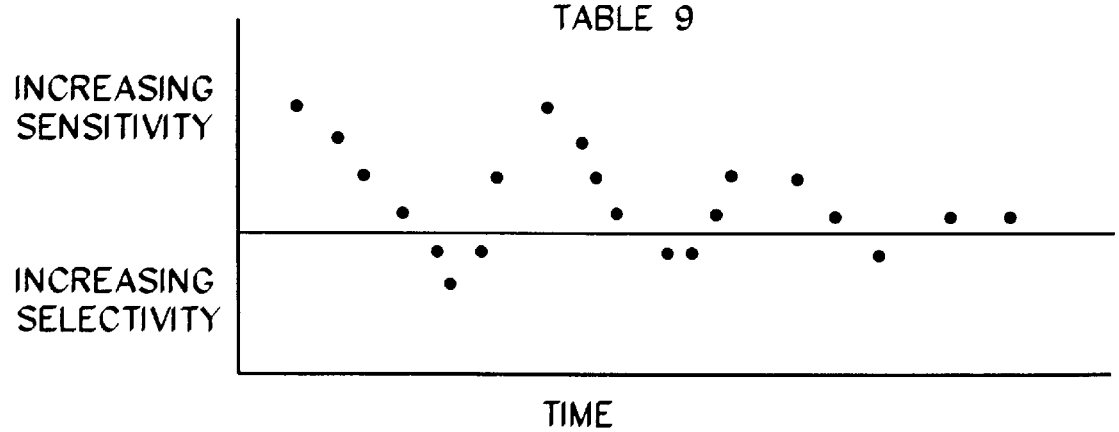
FIG. 27 is Table 9, a plot of sensitivity and selectivity versus time.

Experience from the regionalization of trauma centers in this country shows an interesting trend over time with respect to sensitivity and selectivity. It has been shown that the inverse relationship between sensitivity and selectivity, when plotted over time, yields a sinusoidal wave form in which the amplitude of the wave form gradually decreases with time as the system is "fined tuned" as shown in Table 9 (FIG. 27).

The MDATA system's sensitivity factors are designed to do just that, i.e., fine tune the system over time to find the right balance between sensitivity and selectivity.

In addition to the use of global factors, the MDATA system 100 maintains what are termed "emergency filter response sets." When a patient replies "yes" to any of the problem screening questions, the recommendation or message that follows is called an emergency filter response or "EFR." The EFR sets are modularized so that the system can customize the message that the patient hears. This allows the system 100 to match the EFR sets to the desired level of sensitivity or selectivity as well as provide information specific to an HMO or Managed Care Plan.

System Sensitivity Factors

There are ten sensitivity factors that affect threshold determination in the MDATA system 100:

S1=system-wide (usually established by the system administrator and affects the entire MDATA system)
S2=the anatomic system of the body involved (e.g., nervous system in headache example)
S3=cause (e.g., infection causes meningitis)
S4=problem specific (established by the algorithm author at the beginning of an algorithm)
S5=question specific (within a particular algorithm)
S6=organizational specific (e.g., HMO, hospital)
S7=patient specific
S8=a reserved sensitivity factor for later use
S9=a reserved sensitivity factor for later use
S10=a reserved sensitivity factor for later use Initially, the sensitivity factors have a value of 1.0. The sensitivity factor's value is usually inversely proportional to sensitivity; i.e., if the value is decreased, sensitivity increases.

The sensitivity factors are applied to the threshold constant value in the relational expression component of an IF-Then or If-Then-Else statement of a medical algorithm. For example, let's assume that the system 100 is in the meningitis algorithm and that a temperature greater than 102 degrees will trigger a recommendation to go to a hospital. An example of a threshold calculation without sensitivity factors follows:

If temp>102 then X else Y where X denotes the recommendation to go to the hospital and Y denotes a different branch point. Following is the same example, but including sensitivity factors:

If temp>(102*S1*S2*S3*S4*S5*S6*S7*S8*S9*S10) then X else Y

The use of the sensitivity factors permits anticipation of change. Tuning the initial product of the sensitivity factors from "1.00" to "0.95" would decrease the temperature at which the system recommends a trip to the hospital. Each threshold calculation or other use of the sensitivity factors may use any number of (e.g., two factors) and any combination of the factors. Additionally, any combination of factors may be modified from the initial 1.0 value in any particular threshold calculation.

Age criteria is also modified by use of the sensitivity factors. For example: If Age >45 * S1 * S4 then X else Y.

Examples of areas the system 100 could be tuned follow:

Anatomic system (e.g., cardiovascular)—the system is missing too many heart attacks;

Cause (infection)—the system is missing too many injuries (trauma);

Problem specific (e.g., headache)—the headache algorithm is missing too many cases of meningitis or subarachnoid bleeds;

Question specific (each question in an algorithm can be modified)—this would change the "weight" of a question in a series of weighted questions like the migraine screening questions;

Patient specific—one patient might want to be VERY careful while another might say, "in general I don't go to the doctor until I'm really sure something is wrong with me";

Organizational (e.g., Kaiser patients)—Kaiser hospital management may say that the system is missing too many cases of meningitis and may request to be more careful with their patients (send them in with a lower temperature).

The sensitivity factors affect the following system 100 functions:

(a) Re-enter Feature—the sensitivity factors affect the re-enter horizon, i.e., the amount of time after which the system 100 considers a repetition of the same complaint to be a new problem. If sensitivity increases, the re-enter horizon becomes sooner.

(b) Meta Function—the sensitivity factors affect the matching and time density ratio thresholds. By reducing the values of the system-wide and problem sensitivity factors, e.g., from 1.0 to 0.9, the matching threshold and the time density ratio are decreased:

Example 1 Without Sensitivity factors:
Meta("NHDA", "***", "********", 06/01/93, 12/31/93) If MC>=3 then 100 else 101

Example 1 With Sensitivity factors:
Meta ("NHDA", "***", "********", 06/01/93, 12/31/93) If MC>=(3 * S1 * S4) then 100 else 101

Example 2 Without Sensitivity factors:
Meta("***","*","********", 06/01/93, 12/31/93) If TDR>=2.0 then 200 else 201

Example 2 With Sensitivity factors:
Meta("***", "*", "*******", 06/01/93, 12/31/93) If TDR>=(2.0 * S1 * S4) then 200 else 201

Thus, there is no necessity to change the algorithms themselves. In other words, the factors can be modified rather than changing the algorithms.

(c) Problem Questions—To take the headache example previously used, the sum of the scores of the screening and confirmation questions (and sometimes the questions themselves) is multiplied by the sensitivity factors. The questions are also weighted, of course, depending upon how important each question is to the diagnosis. The sum of the weighted scores is compared against the threshold value that will result in either making the diagnosis of say migraine (in response to the migraine screening questions) or confirming the diagnosis of migraine in response to the migraine confirmation questions.

Thus, if we wanted to increase the sensitivity of diagnosing subarachnoid hemorrhage, we would not have to write another algorithm, but rather, simply multiply the screening and confirmation scores by the sensitivity factors.

For example, if the threshold for the MDATA system 100 to make a diagnosis of subarachnoid hemorrhage based on the sum of the weighted subarachnoid screening questions threshold is set at, say 75%, then that percentage of the sensitivity variable would make this diagnosis with a smaller score and, thus, pick up more cases. Thus, individual diagnoses within an algorithm can be "tuned" independently, and in some cases, this even applies to the individual questions themselves.

(d) Symptom Severity and Symptom Severity Trend Analysis—the sensitivity factors alter the absolute value, the first, second and third slope thresholds. With increased sensitivity, a more gently sloping line triggers an earlier medical evaluation. In the algorithm, when the system 100 makes use of any quantitatable parameter to make a decision, all of these are joined, influenced or multiplied by the sensitivity factors. As a very simple example, if the MDATA system 100 would normally make a recommendation, partly based on the age of the patient (e.g., if you are male and you are over 50 and . . . ), the decision can be triggered if the patient is 49 or 48 and so on.

(e) Home Diagnostic and Treatment Kit—if the patient has a MDATA system treatment kit or a blood pressure cuff, the level at which a fever or blood pressure effects a decision can be changed.

(f) Mental Status Examination—the mental status examination can be modified at a system, or problem (algorithm) level.

(g) Clinical Sound Library—the pattern matching process (as in the clinical sound library) is quantifiable by modifying the sensitivity factors.

XIX. Video Imaging Of the Patient

There are four main types of video imaging: static black and white, static color, video black and white and video color. Each of these main types is now discussed.

Images as basic as static black and white images can provide useful information to the system 100. Static black and white imaging is used with neural net pattern matching. This process permits analyzing for example, facial features to aid in the detection of certain diseases, such as the characteristic facies of Cushing's syndrome or the exophthalmos of Graves disease.

Color static imaging allows color frequency analysis to detect diseases that are not as readily detected with static black and white imaging, such as cyanosis of respiratory failure or the scleral icterus of hepatitis. Color thus provides an incremental benefit in the level of disease detection.

Real time black and white video imaging allows for the evaluation of physical signs such as pupillary responses, extra ocular muscle function, lid lag, and nystagmus. Cranial nerve function can be remotely evaluated, along with, for example, the distinction between central and peripheral VII nerve function.

Color video imaging, especially using fiber optics, adds much more capability in the evaluation of a patient's condition. For example, color video imaging is very useful in evaluating capillary refill or monitoring the response of a patient with cyanosis to supplemental oxygen. Another embodiment of the system 100 may employ inexpensive laser sources to perform real time holographic imaging.

XX. Benefits of the MDATA System

It is rare when the humanitarian and entrepreneurial interests of a venture overlap. The confluence of purpose that exists in the MDATA system is striking. It is a "win-win" proposition from every perspective.

Not only will the MDATA system 100 substantially reduce the overwhelming costs of our current health care system, but for the first time in history, every person can have access to high quality, 100%-consistent and affordable medical advice and information. No matter from what perspective one views the MDATA system 100, its benefits are substantial.

The health care consumer obviously gains the most. Now, whenever he or she has a medical problem, or any member of their family, an immediate consultation can be obtained. The knowledge that the best health care information and medical advice is only a telephone call away can assuage the anxiety of everyone from new mothers to elderly patients confined to their homes.

By endorsing the MDATA system 100, federal, state and local governments could discharge their obligation to provide a universal and affordable level of health care for all of their citizens. In addition, the MDATA system 100 helps care for patients who cannot pay, thus relieving primary care physicians of the necessity to provide care without reimbursement. For the first time, Health Maintenance Organizations and Managed Care Plans will be able to effectively screen patients by telephone in order to ensure that patients are best matched with the services they need.

Specialists can use their talents, not on the repetition of familiar rituals, but will be free to concentrate on those more challenging problems that cannot easily be resolved by the MDATA system 100. They will also benefit from an increased number of patient referrals as well as having a well-constructed patient history when a consultation is sought.

Physicians themselves can access the MDATA system 100 in order to stay informed about new information and technological advances in the medical field. This is particularly true with the treatment, imaging, and laboratory test databases.

Medical information is a continually renewable resource because it is not consumed in its dissemination. The opportunity exists, through the MDATA system 100, for the United States to provide much needed medical information to the world and, at the same time, bring capital into this country. In the process, this country could maintain its leadership in innovation, technology, and software development.

The United States and the world are facing a health care crisis so monumental that it is difficult to comprehend. There are diseases that threaten our very survival as a species. All of us know the apprehension and bewilderment we feel when an illness strikes. When this occurs, we need answers to specific medical questions, answers that are is absolutely up-to-date, instantly available, and affordable.

The key is information: information about prevention, early detection of disease, and about its most efficient treatment. The MDATA system 100 can provide this information through the simple use of the telephone, to nearly every inhabitant of the planet. In addition, the MDATA system 100 converts and explains complicated medical terminology and concepts into language easily understood by everyone.

People do not have to be ill to consult the MDATA system 100, just curious. Patients do not have to schedule appointments, they can simply pick up the telephone. Although many patients will later be seen by a physician, the MDATA system 100 can provide immediate help for everyone. The MDATA system 100 at once establishes egalitarian access to health care information. Although many patients in this country receive state-of-the art medical care, there is a large segment of the population that is deprived of one the most basic health care and medical information. The MDATA system 100 begins to close this enormous gap.

The MDATA system 100 begins to effect a restructuring of the health care delivery system in which both health care consumers and providers participate in the improvement of the system itself. The MDATA system 100 and its patients will be in partnership to provide the most current, economical, and concise treatment available. The upside potential is unlimited. Whether one believes health care is a right or a privilege, there can be no doubt that it is fundamentally necessary. Whether one believes we have a civic responsibility or a moral obligation to care for one another, it must be done. The fundamental simplicity of the structure of the MDATA system 100 belies its power as a highly useful tool in the delivery of health care.

XXI. Optional System Configuration

A second embodiment of the MDATA system entails a major shift of how the questions and responses are delivered to the patient. Rather than the use of a telephone, the voice processing and voice response technology, the system software is published via media such as floppy disks, CD ROM, or PCMCIA cards for use on a patient's personal computer. This second embodiment is referred to as the screen version or the (Stand-Alone) SA-MDATA system. The computer could be, for example, a desktop computer, a laptop or notebook computer, or a handheld, pen-driven computer. The system questions are displayed on a display screen that is part of the computer or is connected to the computer. The patient uses a keyboard or a pointing/writing device connected to the computer to respond to the questions. The patient files are maintained and updated within the computer or on removable storage devices. The diagnosis, advice, and treatments can be displayed on the screen and also printed in hardcopy form on a printer (if available). New versions of the SA-MDATA system are either mailed to subscribers are available via modem. These new versions may include updates of the treatment table for new treatments. Another embodiment of the SA-MDATA system may include using specialized receiver devices that receive encoded FM signals on a demand basis when an event (a new treatment) triggers the device, such as described in U.S. Pat. No. 5,030,948.

A unique and separate authoring language (called File output or FO) was used to develop the medical algorithms used in the screen version embodiment of the system 100. Through the use of FO, the contents of text files are presented online to users, and then the users respond to questions and directions issued by the text files.

FO is designed as a typical, generalized authoring language, in which commands are embedded into text files (herein called FO files) to perform specific screen and keyboard functions. FO files are in effect programs written in the FO "language" that communicate (via FO) with the user online.

FO adds no text of its own. In fact, FO does not need to know what text file content it is executing. The programmer or author of a FO file is in complete control of the text content and the sequence in which it is presented. Using the various commands described in the Authoring Language Syntax document listed in the Microfiche Appendix, the author can display text, format the screen, ask the user questions, input responses from the user, select different text files for execution, and generally control and direct the entire session.

This version of FO is intended as a development version that gives the user much freedom at the keyboard. The user can interrupt a presentation and edit the FO file being presented. The assumption here is that the user is in fact the author or an alpha tester charged with verifying and correcting file content.

A FO file is any standard sequential ASCII text file with variable-length lines terminating with a Carriage Return (ASCII 13). Any line with a period in column one is treated as a command. A line without a leading period is treated as a print command.

The FO program processes a FO file by reading it one line at a time into memory. If the line is a text line, it is printed and the next line is loaded. If the line is a command line, the command is executed. If the command involves a wait on the user (such as a .M command), FO continues loading the FO file behind the scenes until it has been completely loaded. In this manner, FO executes the FO file as it is loading it. Once loaded, the FO file remains entirely in memory.

The system software for the screen version embodiment is written in Borland Turbo Pascal version 3.0. A second version of the system software for the screen version embodiment of the system 100 is written in Microsoft G. W. Basic and is run in interpretive mode. The Microfiche Appendix contains the following for the screen version:

Authoring Language Syntax Document;
Pascal Source Code;
System Functions; and
An Exemplary Medical Algorithm (Headache).

In yet other embodiments, other databases/files or algorithms can be used. The general system, method and procedures would remain the same. For example, a specialty field such as sports medicine could be added to the system.

The MDATA system 100 described herein finds application in many environments, and is readily adaptable for use therein. For example, the system finds use in any application that is step-oriented and can be algorithmically described. For example, the system could give car diagnostic services over the phone to a caller. Then, when the car is brought to a service facility for repairs (treatment), the caller will be informed and have a good idea of what the problem is and probable repairs will be. Accordingly, the claims are to be interpreted to encompass these and other applications of the invention within their scope and are not to be limited to the embodiments described herein.

XXII. Summary of Advantages of the Present Invention

One of the main problems of the health care crisis is the limited access to health care information when it is needed. The MDATA system provides up-to-date medical information and advice that is instantly available twenty-four hours a day. The advice that is given is 100% consistent.

The quality of the advice is much better if a physician can stop, research, and anticipate all possible causes of a problem and then systematically go about dealing with all of these possible causes. In medical practice, a physician just does this from memory.

No humans are necessary to actually give the medical advice. The MDATA system is automated which helps to bring down the cost of health care.

An exact record of the questions asked and the answers given is stored in the patient's database. The MDATA system time-and-date stamps the responses to the questions (as transaction records) so that an exact reconstruction of the patient's interview(s) can be generated for use by a physician or other health care professional. The system also keeps a record of what version of an algorithm has been consulted as well as the sensitivity factor set for that consultation. At the conclusion of the interaction, the MDATA system can tell the patient how long the consultation has taken and what charges have been incurred, if any.

When possible, the MDATA system 100 takes into account the past medical history of the patient, especially those pieces of information learned from past consultations with the MDATA system 100, before advice is given. In addition, the advice given is different depending upon the age and sex of the patient. The "meta" functions provide another advantage by allowing the MDATA system 100 to evaluate a problem in the context of the patient's prior consultations with the system.

While the above detailed description has shown, described and pointed out the fundamental novel features of the invention as applied to various embodiments, it will be understood that various omissions and substitutions and changes in the form and details of the device illustrated may be made by those skilled in the art, without departing from the spirit of the invention.

What is claimed is:

1. A method of automating medical diagnosis and treatment advice, operating in a computer system, comprising:

providing a representation of connected nodes corresponding to a set of diagnostic steps for a selected medical problem;

providing a set of action lists associated with each node;

providing a script for each one of selected nodes, each script requesting information or providing medical advice;

translating the node representation into a node table and a plurality of list files;

processing the list files and a plurality of records in the node table to generate patient questions;

presenting the patient questions to a patient;

receiving answers from the patient; and generating medical advice based on the answers to the patient questions and the diagnostic steps for a selected medical problem.

2. The method defined in claim 1, additionally comprising developing the set of diagnostic steps for a selected medical problem.

3. The method defined in claim 1, wherein the set of action lists include a play list, a next list and a work list.

4. The method defined in claim 1, additionally comprising obtaining and storing a patient's past medical history.

5. The method defined in claim 1, wherein the processing utilizes an automatic speech recognition system to receive patient answers.

6. The method defined in claim 1, wherein the processing utilizes a keyboard to receive patient answers.

7. The method defined in claim 1, wherein the processing utilizes a dual tone multiple frequency (DTMF) signal processing system to receive patient answers.

8. The method defined in claim 1, wherein the processing utilizes a speech playback system to transmit patient questions.

9. The method defined in claim 1, wherein the processing utilizes a visual display to transmit patient questions.

10. A method of providing medical information to any one of a plurality of patients, operating in a medical diagnostic and treatment advice system comprising an algorithm processor executing in a computer, comprising:

providing a representation corresponding to a set of steps directed to diagnosing a selected medical problem;

translating the representation into one of a plurality of medical complaint algorithms;

selectively executing one of the plurality of medical complaint algorithms;

determining medical advice particular to a medical condition through communication with the computer; and providing the medical advice particular to the medical condition to an output of the computer.

11. The method defined in claim 10, additionally comprising performing an evaluation process by the algorithm processor, wherein the evaluation process comprises the plurality of medical complaint algorithms.

12. The method defined in claim 11, additionally comprising:

creating a patient medical history database having a past medical history file for each patient; and accessing the patient medical history database during the evaluation process.

13. The method defined in claim 10, additionally comprising providing the set of steps directed to diagnosing a selected medical problem.

14. The method defined in claim 10, additionally comprising generating a diagnosis during execution of one of the medical complaint algorithms.

15. The method defined in claim 14, additionally comprising:

storing a treatment table in the computer;

selectively accessing the treatment table based on the diagnosis; and communicating a selected treatment to the patient.

16. The method defined in claim 10, additionally comprising obtaining and storing a patient's past medical history.

17. The method defined in claim 16, additionally comprising protecting security of a medical history of the patient.

18. The method defined in claim 17, wherein protecting the security includes assigning a unique patient identification number to each patient using the system.

19. The method defined in claim 17, wherein protecting the security includes providing access to an assistant on behalf of the patient.

20. The method defined in claim 10, wherein the representation comprises a set of connected nodes.

21. A method of providing medical information to a patient, operating in a medical diagnostic and treatment advice system comprising an algorithm processor executing in a computer, wherein an input and an output device connect to the computer, comprising:

providing a representation of connected nodes corresponding to a set of diagnostic steps for a selected medical problem;

translating the node representation into a node table and a plurality of list files thereby generating a medical complaint algorithm;

processing the list files and a plurality of records in the node table on the algorithm processor to generate patient questions;

transmitting medical information via the output device;

receiving medical information via the input device;

scoring at least a portion of the received medical information;

repeating the transmitting, receiving and scoring a plurality of times;

combining each of the scores obtained from the scoring to create a combined score;

comparing the combined score with a threshold; and diagnosing the medical condition associated with the executed medical complaint algorithm if the combined score reaches or passes through the threshold.

22. The method defined in claim 21, additionally comprising communicating medical advice to the patient via the output device.

23. The method defined in claim 22, wherein the medical advice comprises the diagnosed medical condition and a score.

24. The method defined in claim 22, wherein the medical advice comprises a treatment associated with the diagnosed medical condition.

25. The method defined in claim 21, additionally comprising providing the set of steps directed to diagnosing a selected medical problem.

* * * * *